(12) United States Patent
Yoon et al.

(10) Patent No.: US 11,220,543 B2
(45) Date of Patent: Jan. 11, 2022

(54) ANTIBODY BINDING SPECIFICALLY TO CD66C AND USE THEREOF

(71) Applicant: DINONA, Seoul (KR)

(72) Inventors: Sangsoon Yoon, Seoul (KR); Kwon Pyo Hong, Cheongju-si (KR); Soseul Kim, Seoul (KR); Gil Yong Ji, Seoul (KR); Young Hoon Lim, Nonsan-si (KR)

(73) Assignee: DINONA, Seoul (KR)

( * ) Notice: Subject to any disclaimer, the term of this patent is extended or adjusted under 35 U.S.C. 154(b) by 173 days.

(21) Appl. No.: 16/346,259

(22) PCT Filed: Nov. 14, 2017

(86) PCT No.: PCT/KR2017/012891
§ 371 (c)(1),
(2) Date: Apr. 30, 2019

(87) PCT Pub. No.: WO2018/088877
PCT Pub. Date: May 17, 2018

(65) Prior Publication Data
US 2019/0263905 A1      Aug. 29, 2019

(30) Foreign Application Priority Data

Nov. 14, 2016   (KR) .......................... 10-2016-0151359

(51) Int. Cl.
| | |
|---|---|
| *C07K 16/28* | (2006.01) |
| *A61K 39/395* | (2006.01) |
| *A61P 35/00* | (2006.01) |
| *A61K 45/06* | (2006.01) |
| *C07K 16/30* | (2006.01) |
| *G01N 33/574* | (2006.01) |
| *A61K 39/00* | (2006.01) |

(52) U.S. Cl.
CPC .... *C07K 16/2803* (2013.01); *A61K 39/39558* (2013.01); *A61K 45/06* (2013.01); *A61P 35/00* (2018.01); *C07K 16/2818* (2013.01); *C07K 16/2827* (2013.01); *C07K 16/30* (2013.01); *G01N 33/574* (2013.01); *A61K 2039/505* (2013.01); *A61K 2039/507* (2013.01); *C07K 2317/24* (2013.01); *C07K 2317/73* (2013.01)

(58) Field of Classification Search
None
See application file for complete search history.

(56) References Cited

U.S. PATENT DOCUMENTS

| | | | | |
|---|---|---|---|---|
| 8,404,812 B2 * | 3/2013 | Song | ................ | C07K 14/70503 530/387.1 |
| 10,472,418 B2 * | 11/2019 | Hong | ................. | C07K 16/2803 |
| 2006/0088521 A1 | 4/2006 | Mahadevan | | |
| 2011/0212095 A1 | 9/2011 | Song et al. | | |
| 2012/0148592 A1 * | 6/2012 | Imai | ........................ | A61P 1/02 424/139.1 |
| 2013/0095033 A1 | 4/2013 | Chang et al. | | |
| 2014/0099254 A1 | 4/2014 | Chang et al. | | |

FOREIGN PATENT DOCUMENTS

| | | |
|---|---|---|
| JP | 2015-518826 | 7/2015 |
| KR | 10-2011-0098593 | 9/2011 |
| KR | 10-2016-0031167 | 3/2016 |
| KR | 10-2016-0108310 | 9/2016 |
| WO | 2016-150899 | 9/2016 |
| WO | 2017-209318 | 12/2017 |

OTHER PUBLICATIONS

Strickland et al (Journal of Pathology, 2009, 218:380-390).*
Blumenthal et al (Cancer Research, 2005, 65:8809-8817).*
Segal et al (Journal of Clinical Oncology, 32, No. 15¬suppl (May 20, 2014), abstract 3002).*
Kristiina Nordfors et al., "The Tumour-associated carbonic anhydrases CA II, CA IX and CA XII in a group of medulloblastomas and supratentorial primitive neuroectodermal tumours: an association of CA IX with poor prognois", BMC cancer, vol. 10, 2010.
Ulmasov, B., (2000). Purification and kinetic analysis of recombinant CA XII, a membrane carbonic anhydrase overexpressed in certain cancers.Proc Natl Acad Sci USA 97, 14212-14217.
Sherie L. Morrison et al., "Chimeric human antibody molecules: Mouse antigen-binding domains with human constant region domains", Proc. Nati. Acad. Sci. USA, vol. 81, pp. 6851-6855, 1984.
Sherie L. Morrison et al., "Genetically Engineered Antibody Molecules", Advances in Immunology, vol. 44, 1988.
Martine Verhoeyen et al., "Reshaping Human Antibodies: Grafting an Antilysozyme Activity", Science, vol. 239, pp. 1534-1536, 1988.
Eduardo A. Padlan, "A Possible Procedure for Reducing the Immunogenicity of Antibody Variable Domains While Preserving Their LIGA~D-Binding Properties", Molecular Immunology, vol. 28, No. 4/5, pp. 489-498, 1991.
Eduardo A. Padlan, "Anatomy of the Antibody Molecule", Molecular Immunology, vol. 31, No. 3, pp. 169-217, 1994.
EPO, Extended European Search Report of EP 17869760.3 dated Sep. 23, 2020.
Yunqiang Zhang et al., "CEACAM6 promotes tumor migration, invasion, and metastasis in gastric cancer", Acta Biochim Biophys Sin (2014) vol. 46, pp. 283-290, Feb. 3, 2014.

(Continued)

*Primary Examiner* — Laura B Goddard
(74) *Attorney, Agent, or Firm* — Lex IP Meister, PLLC

(57) ABSTRACT

The present invention relates to an anti-CD66c antibody and its use for treating cancer, and more particularly, it is possible to induce T-cell activation or humoral immune response using an antibody specifically recognizing CD66c. A nucleic acid molecule encoding the antibody or antigen-binding fragment thereof, a vector comprising the nucleic acid molecule, a host cell and the antibody or antigen-binding fragment thereof is used for alleviation, prevention, treatment or diagnosis of CD66c-related disease.

13 Claims, 38 Drawing Sheets
(16 of 38 Drawing Sheet(s) Filed in Color)
Specification includes a Sequence Listing.

(56) References Cited

OTHER PUBLICATIONS

Rosalyn D. Blumenthal et al., "Inhibition of Adhesion, Invasion, and Metastasis by Antibodies Targeting CEACAM6 (NCA-90) and CEACAM5 (Carcinoembryonic Antigen)", Cancer Res (2005) vol. 65, No. 19, pp. 8809-8817, Oct. 1, 2005.

\* cited by examiner

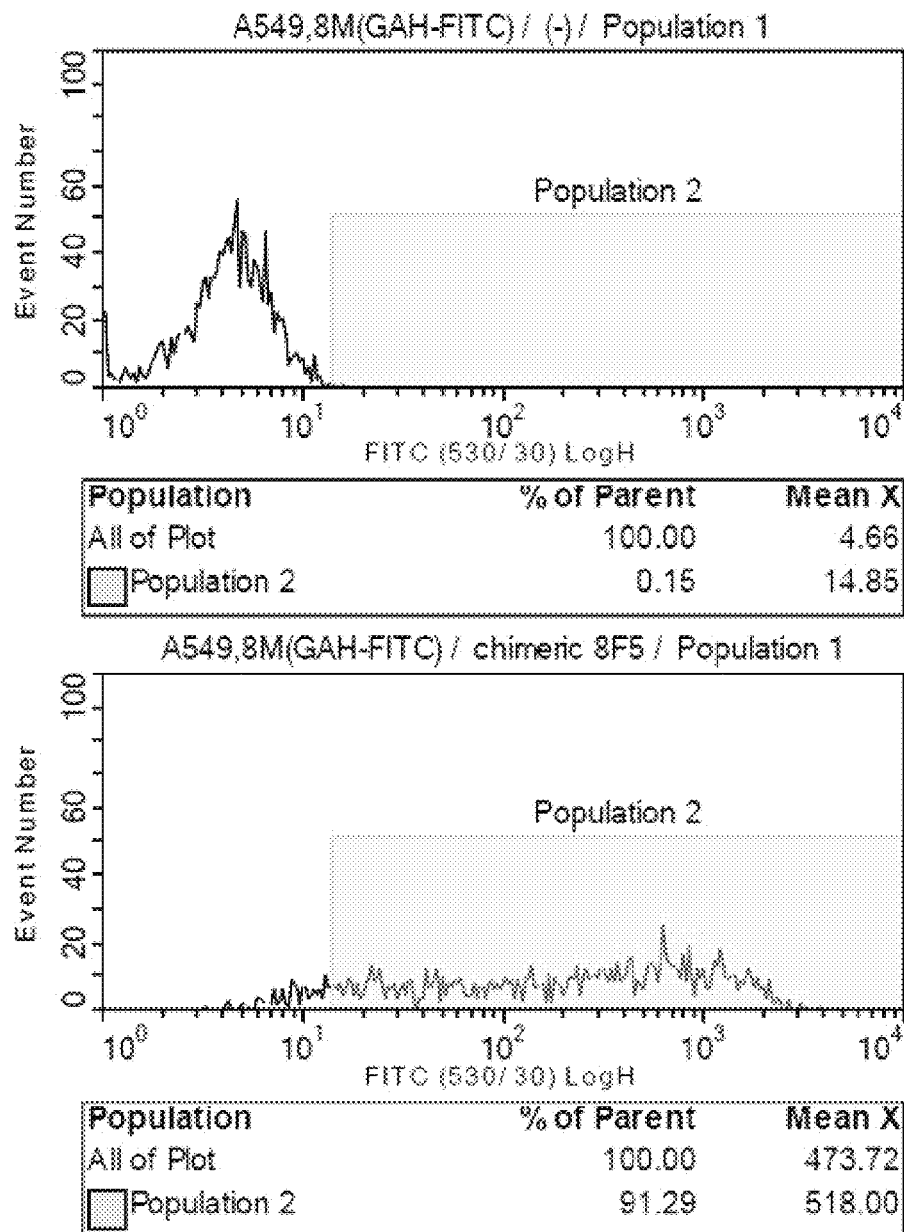
[Fig. 1]

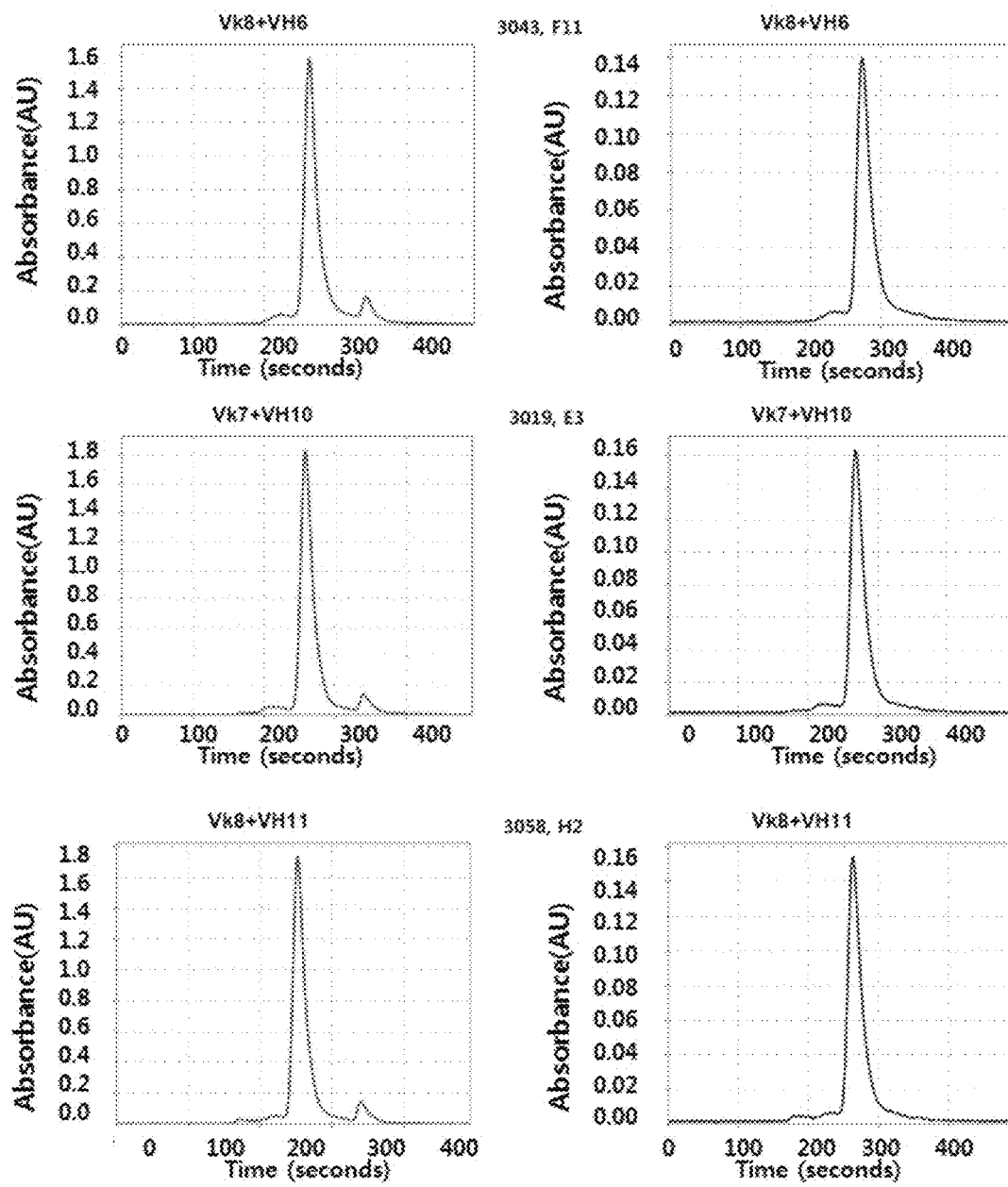
[Fig. 2a]

[Fig. 2b]
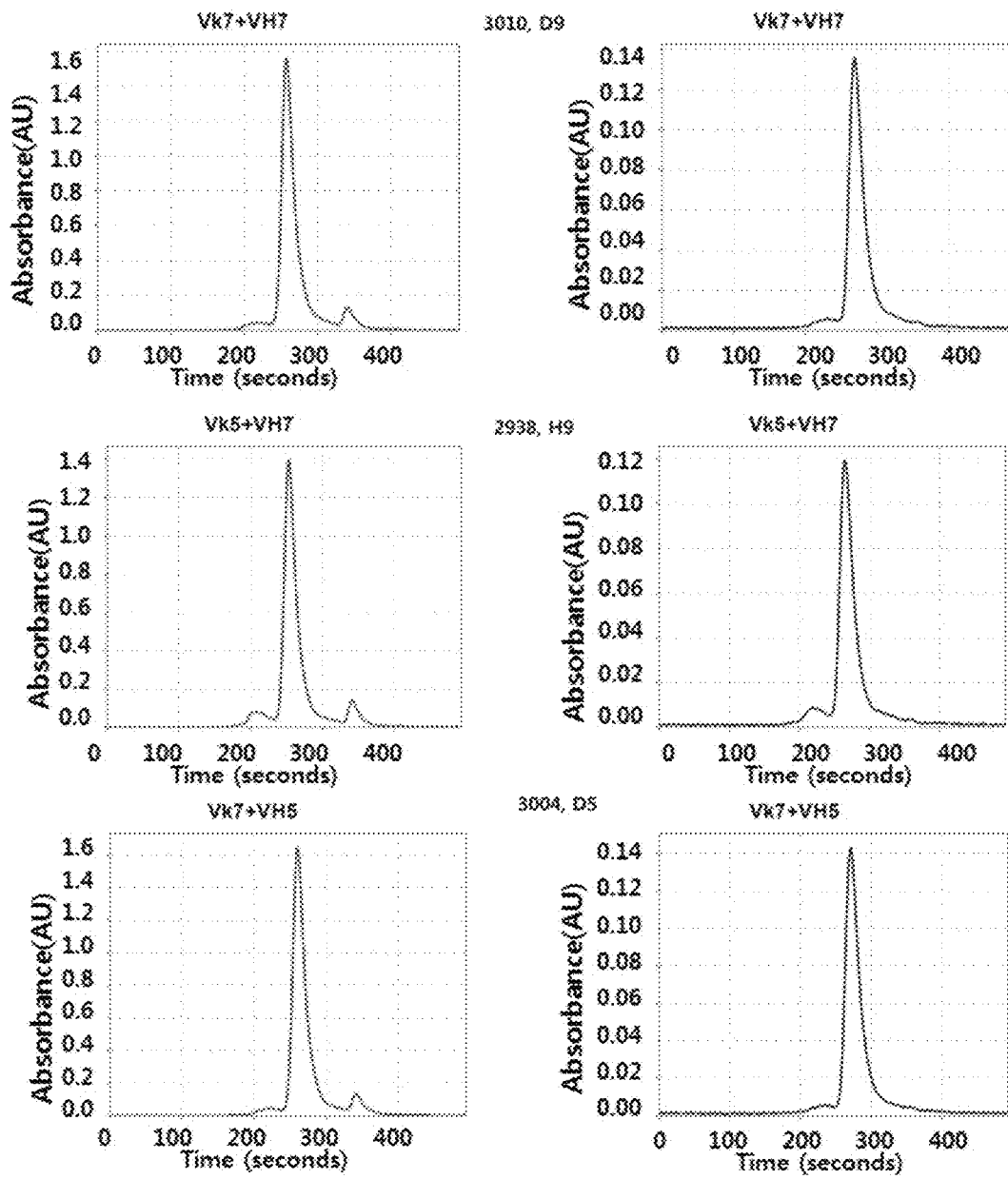

[Fig. 2c]
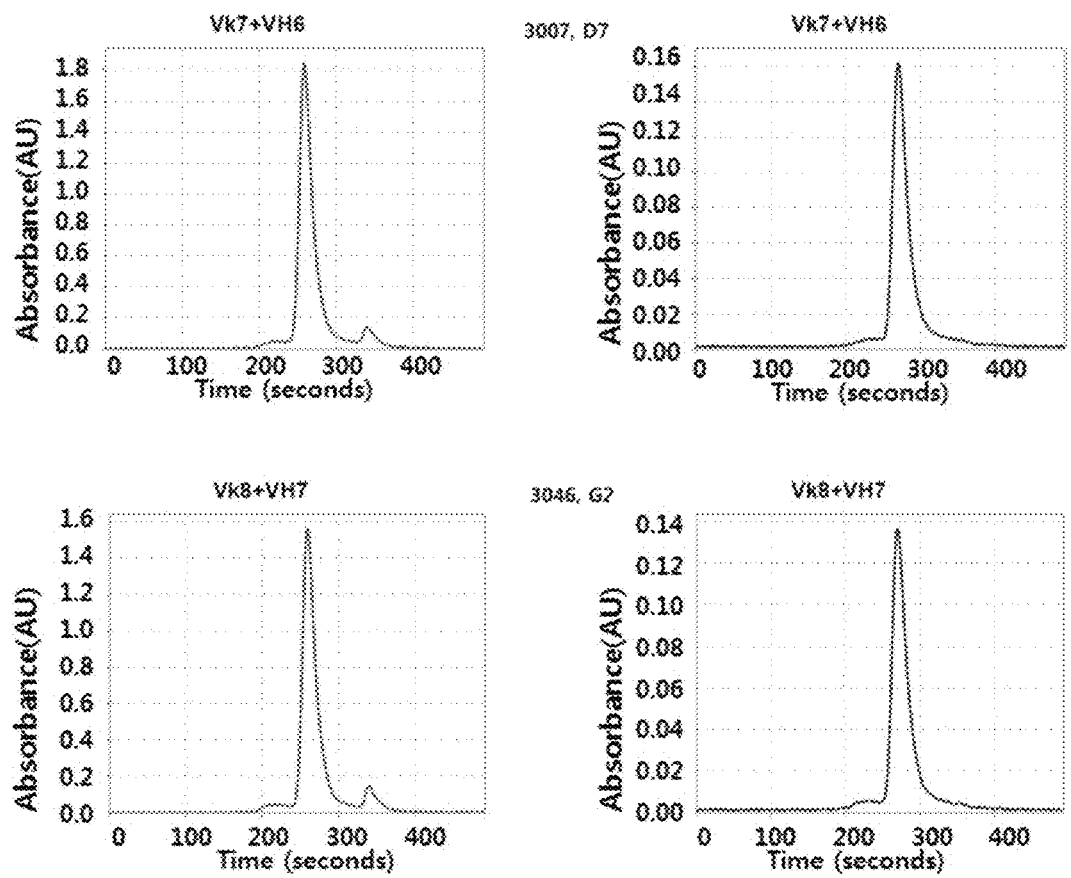

[Fig. 3a]
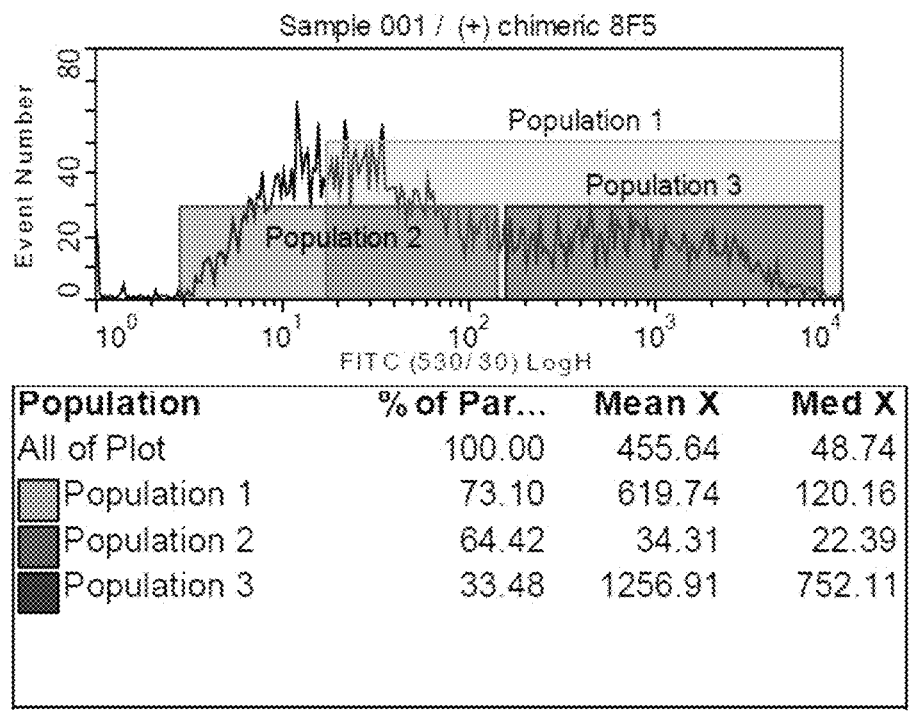
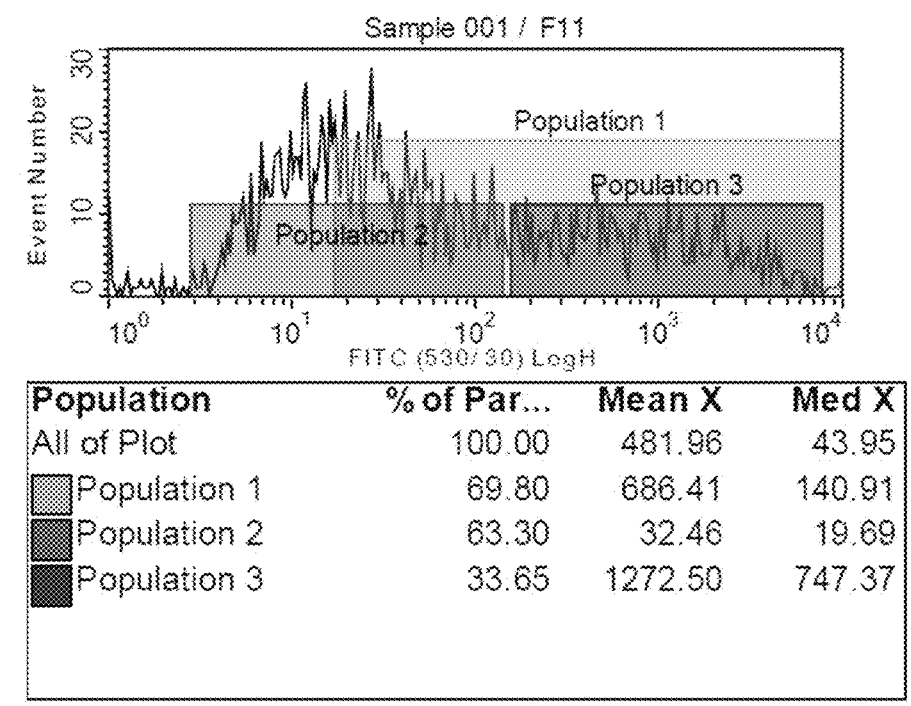

【Fig. 3b】
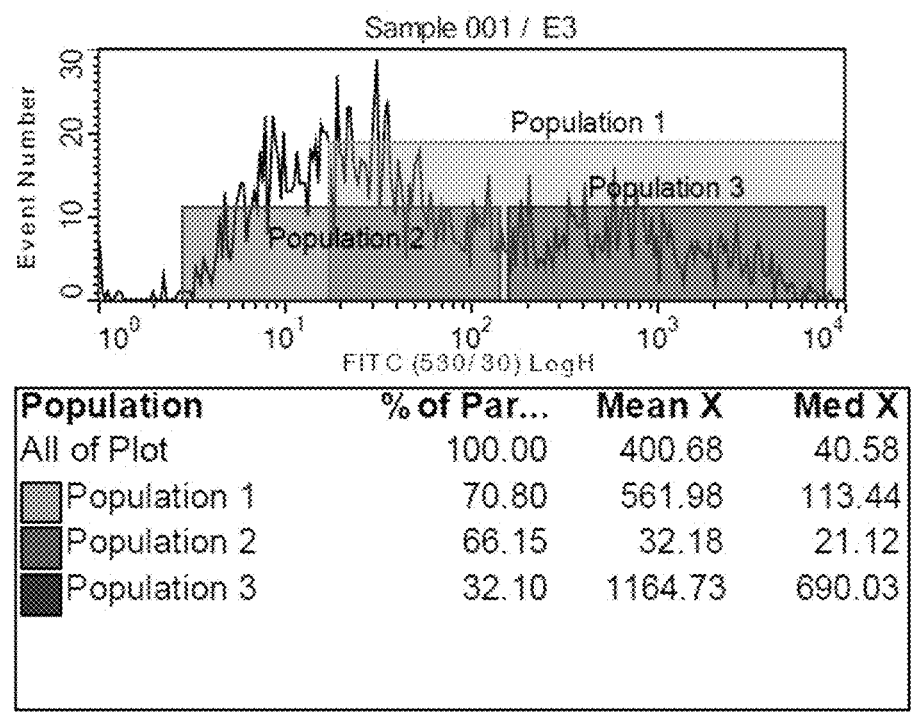
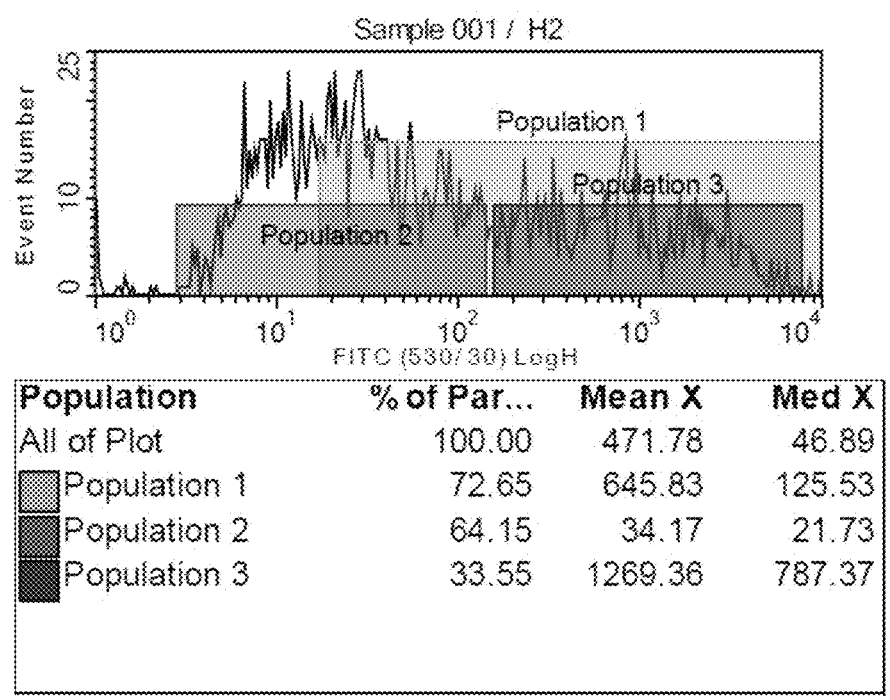

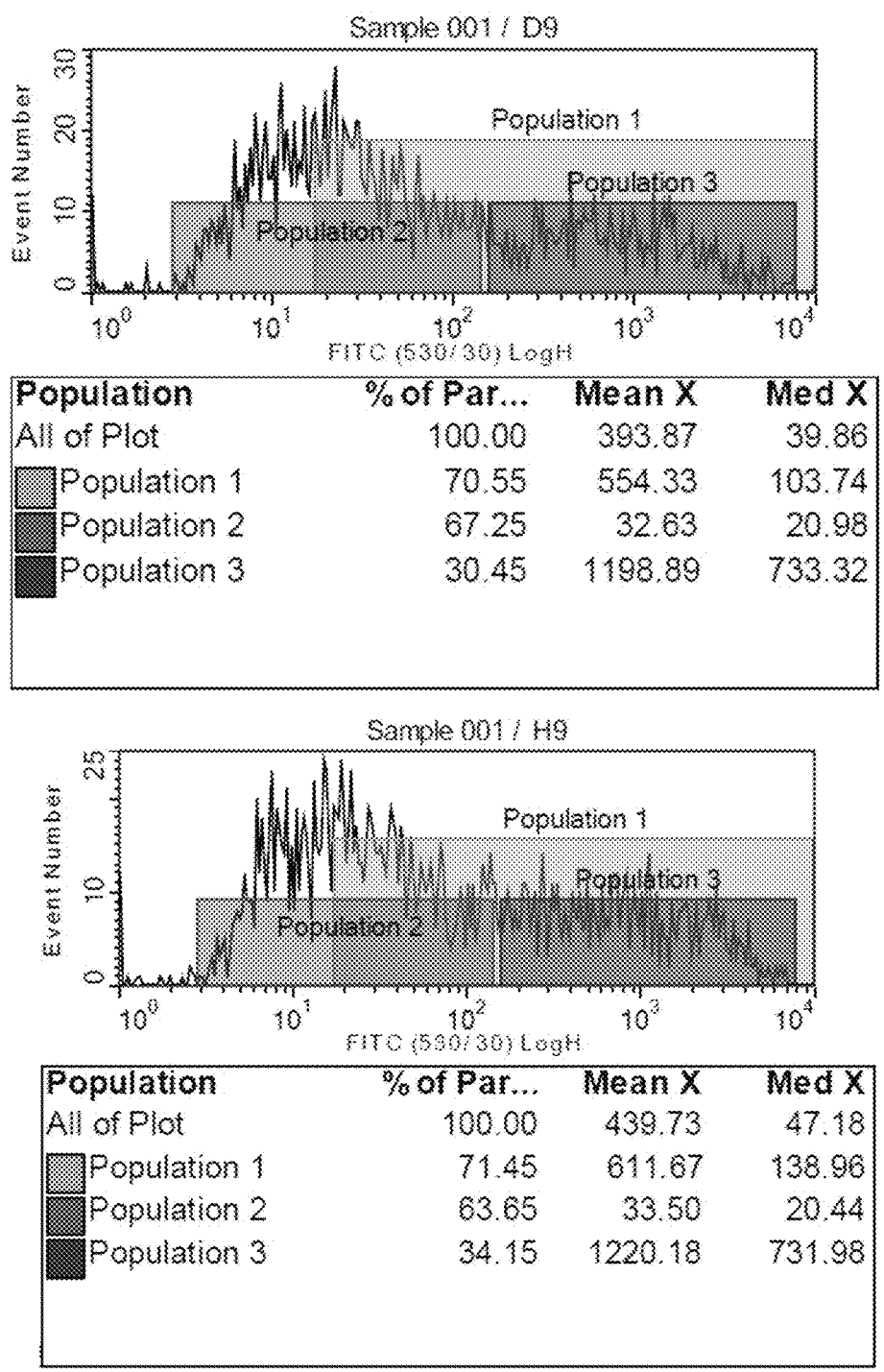
[Fig. 3c]

[Fig. 3d]
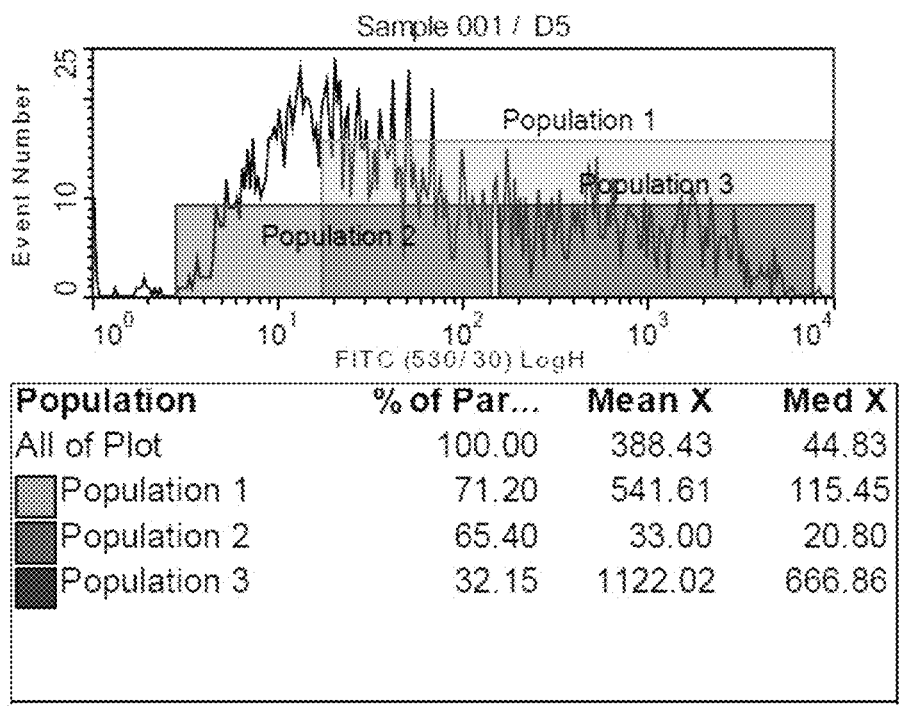
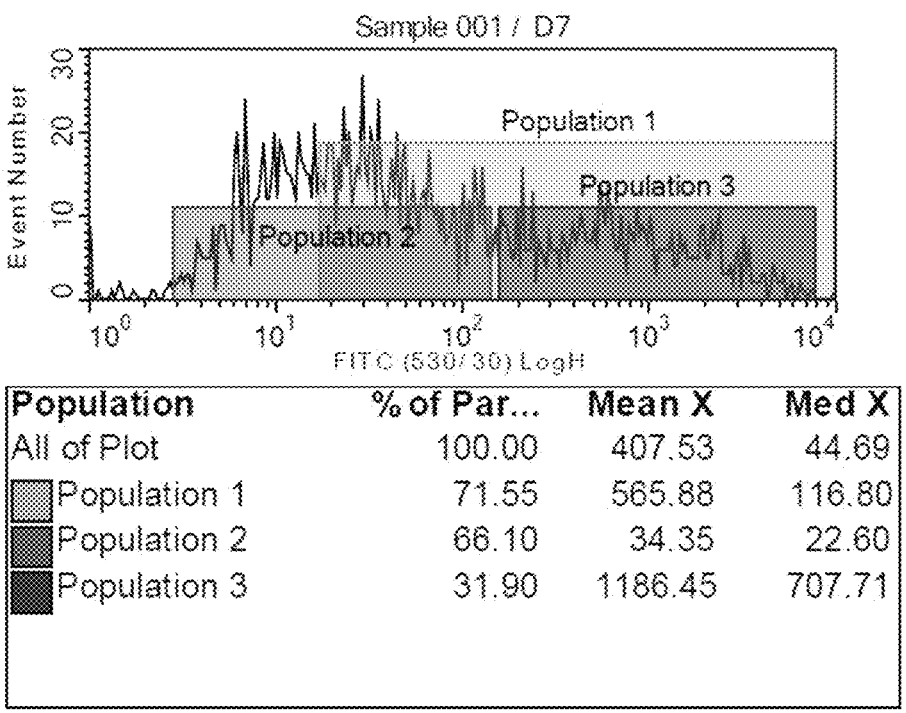

[Fig. 3e]
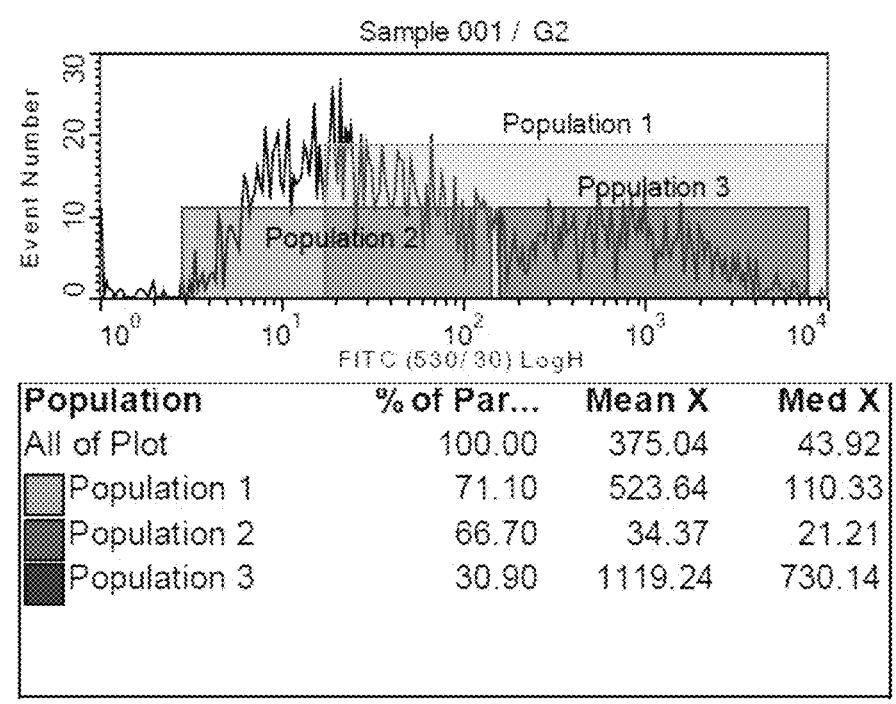

[Fig. 4a]
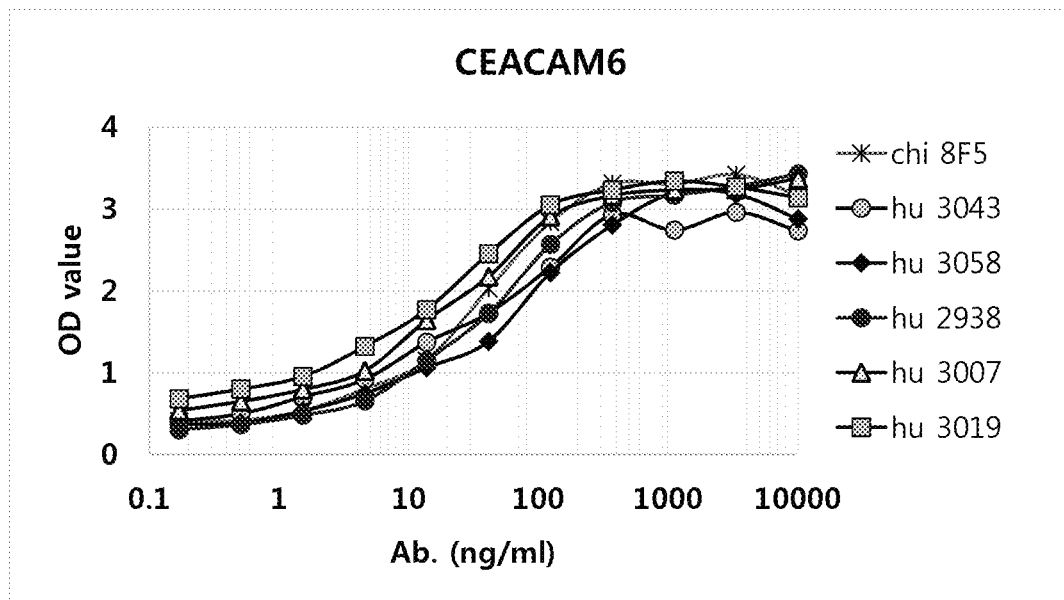
[Fig. 4b]
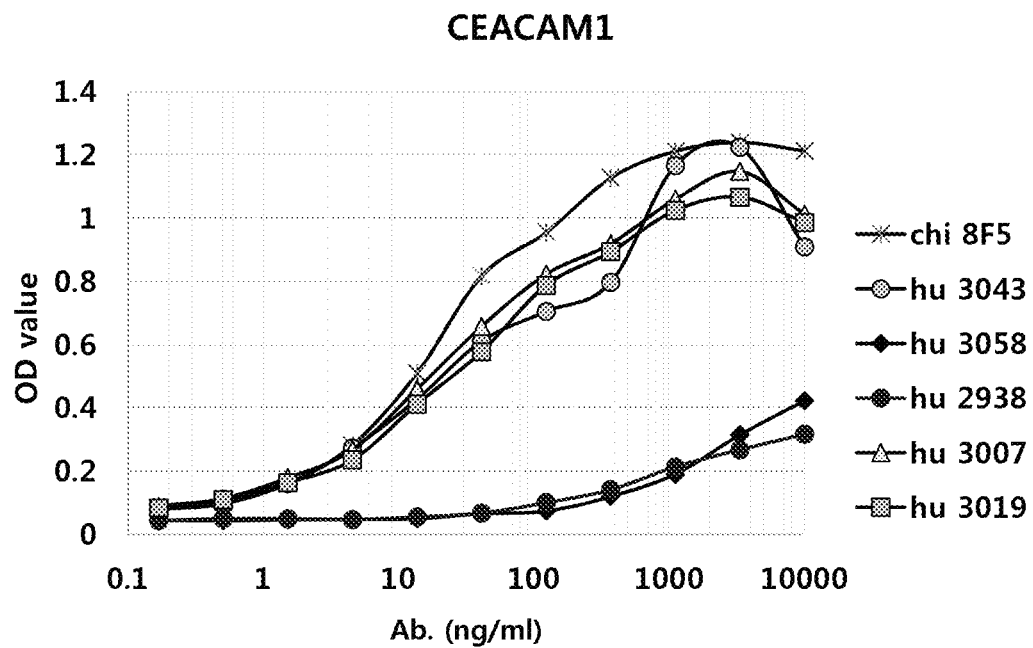

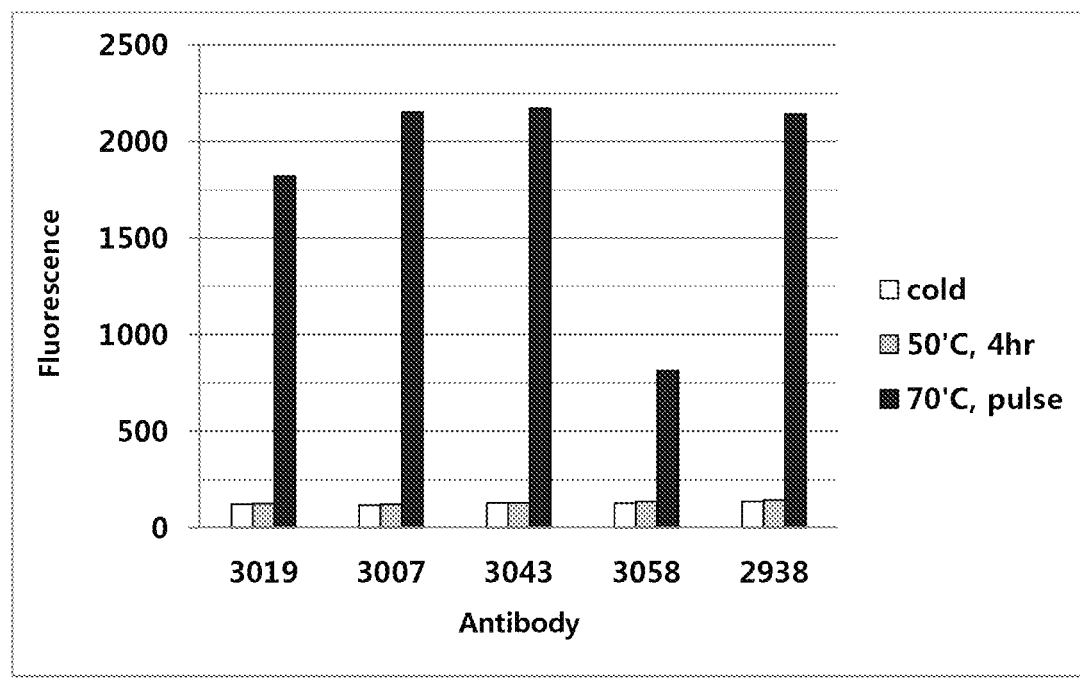
[Fig. 5a]

[Fig. 5b]
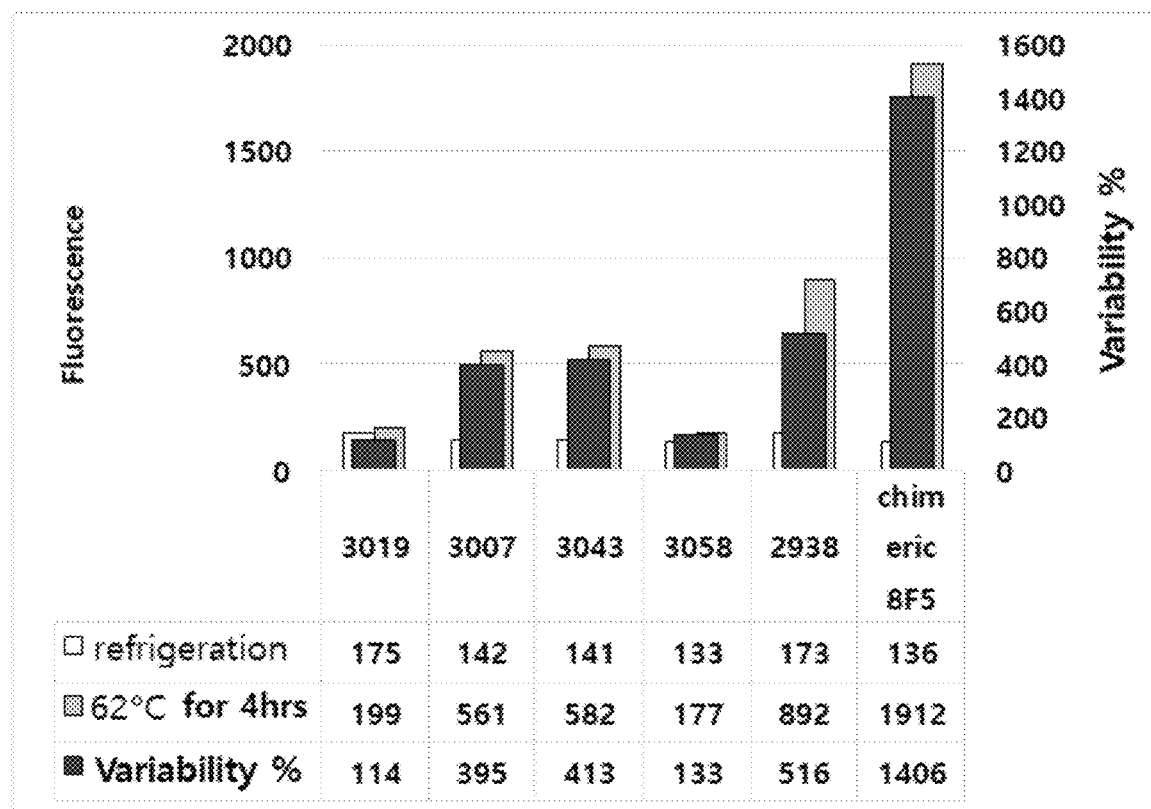

[Fig. 6a]
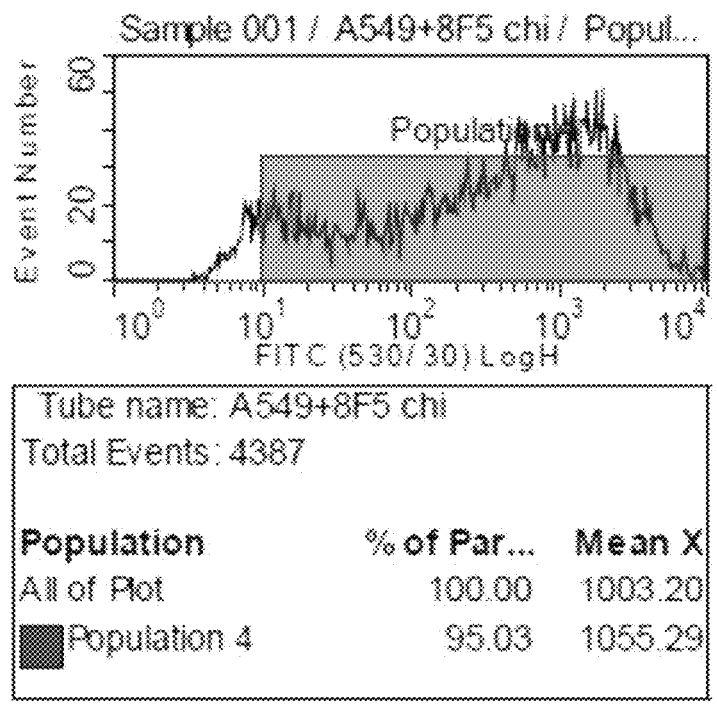
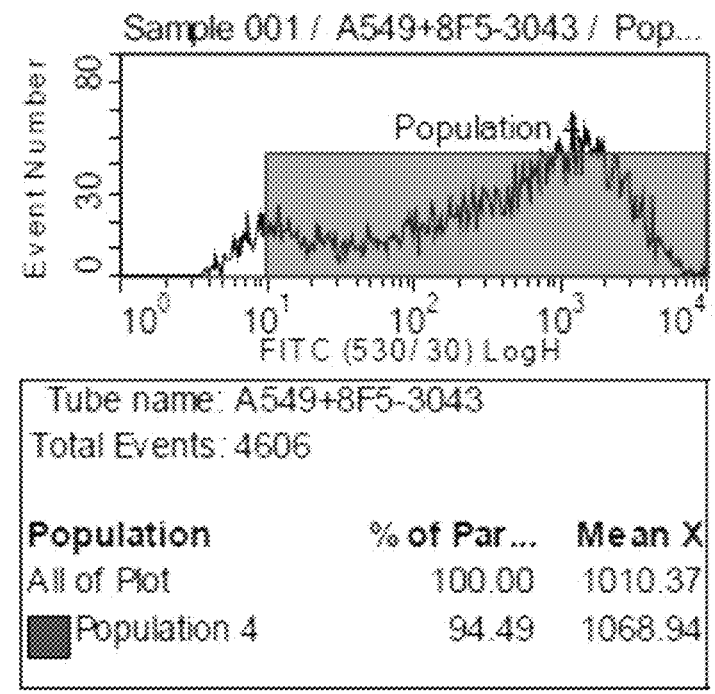

[Fig. 6b]
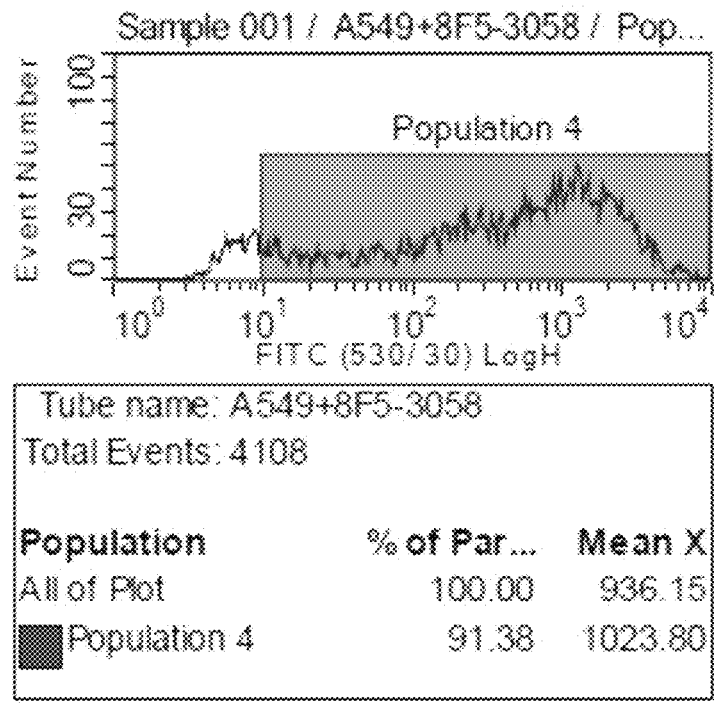
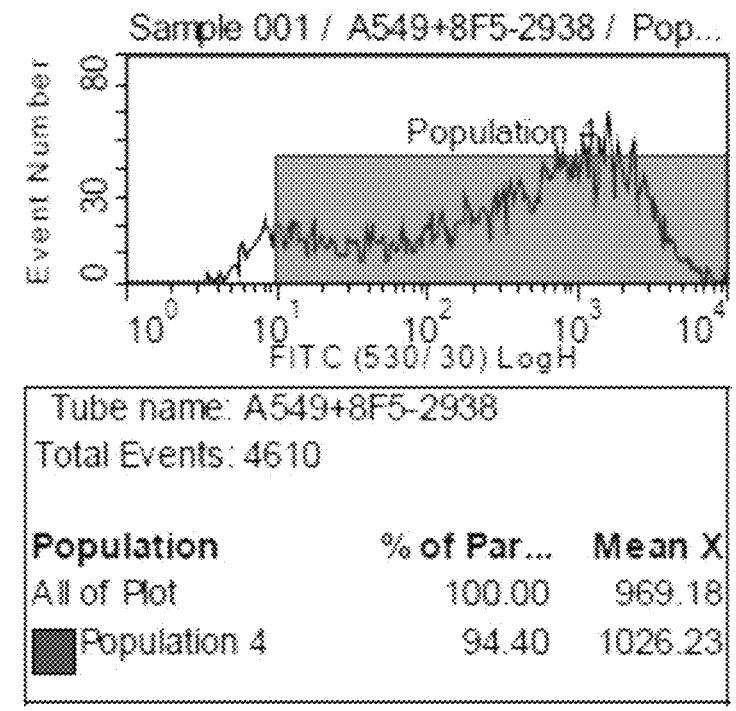

[Fig. 6c]
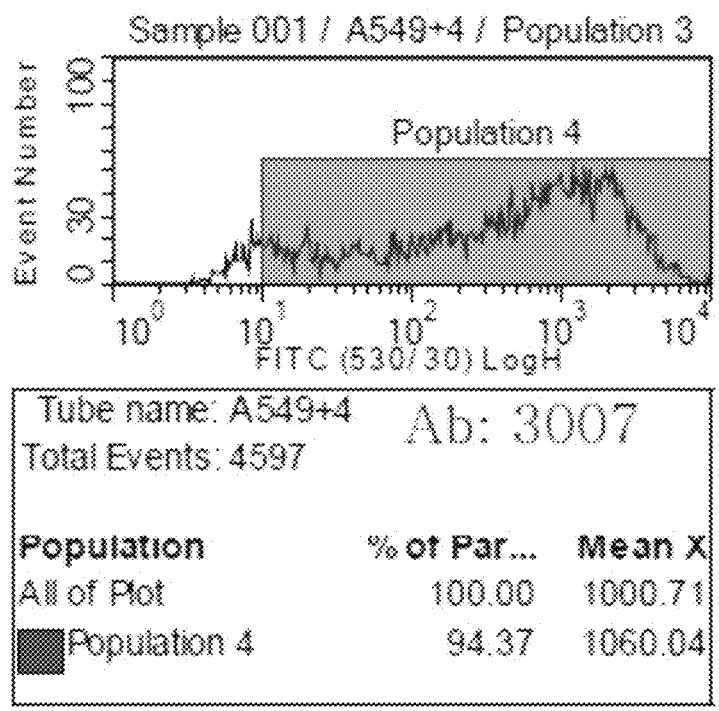
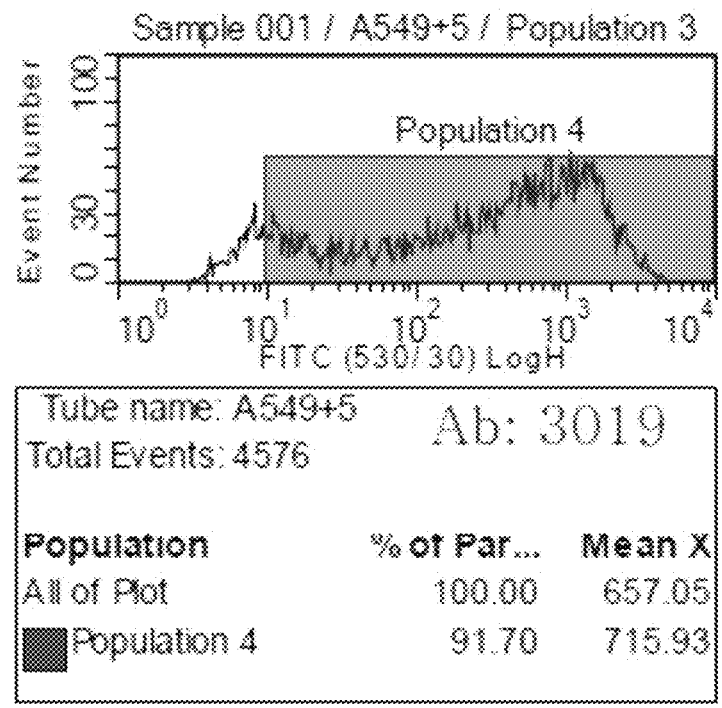

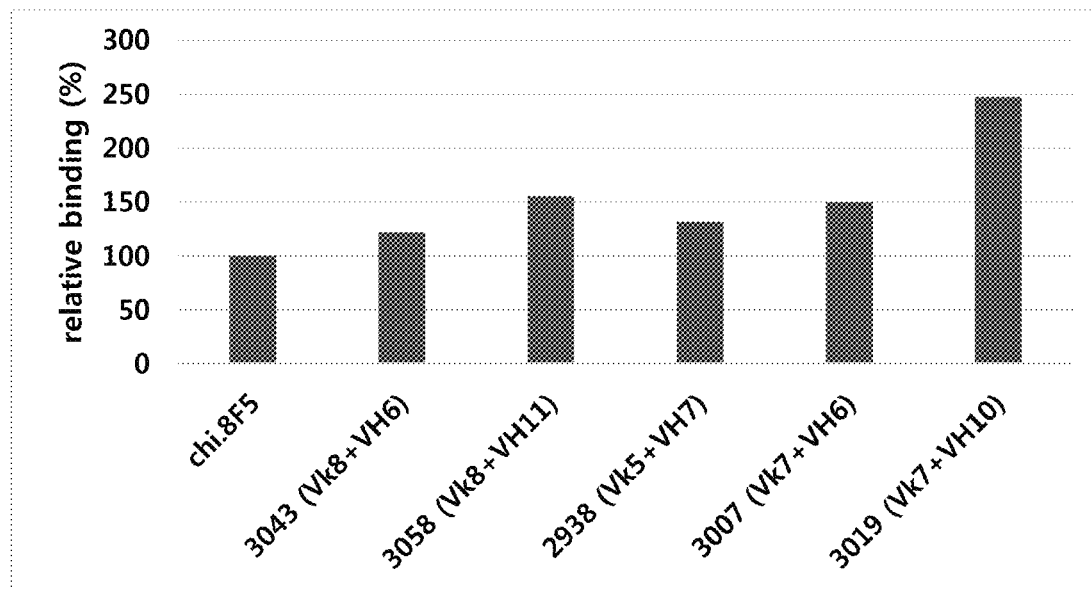
[Fig. 6d]

[Fig. 7a]
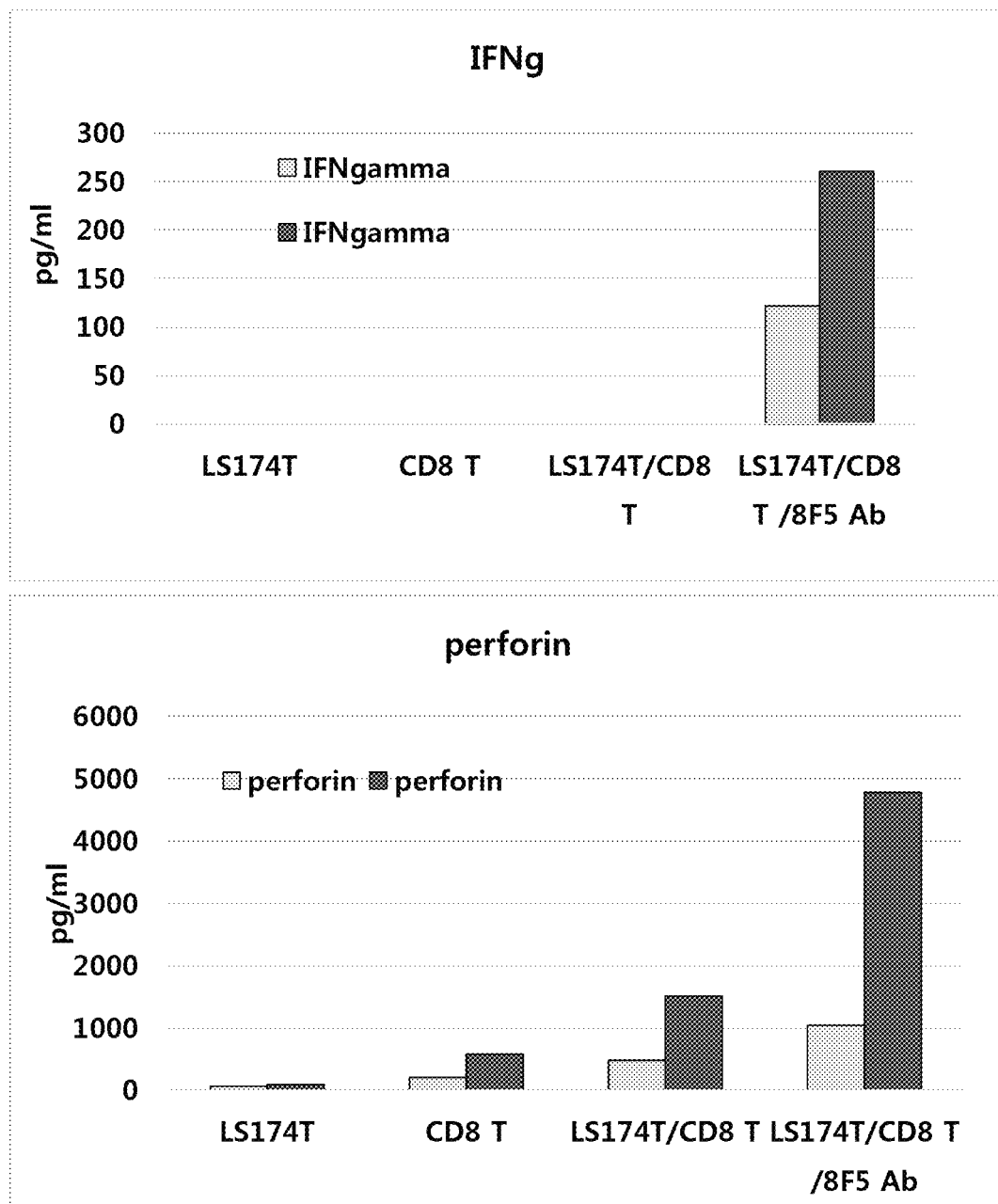

[Fig. 7b]
LS174T
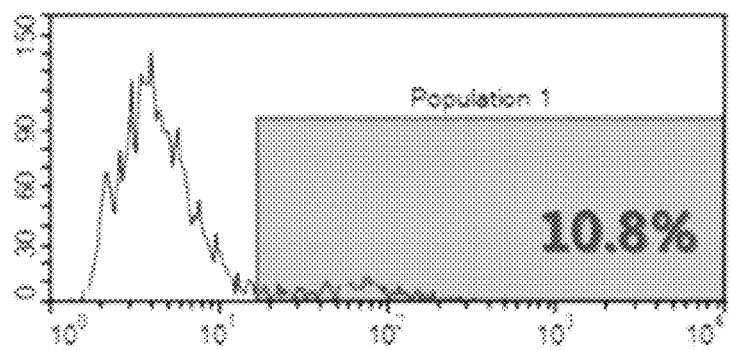
CD8 T / LS174T
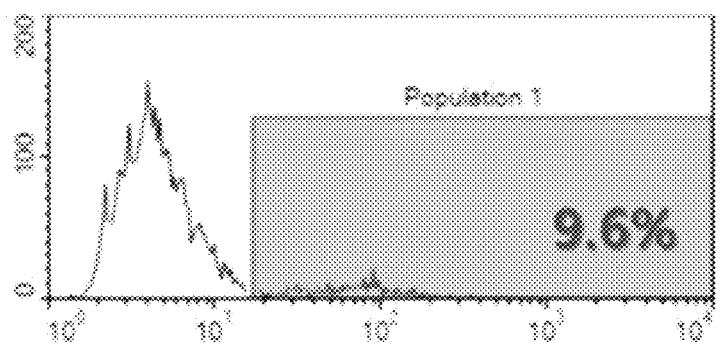
CD8 T / LS174T / 8F5 Ab
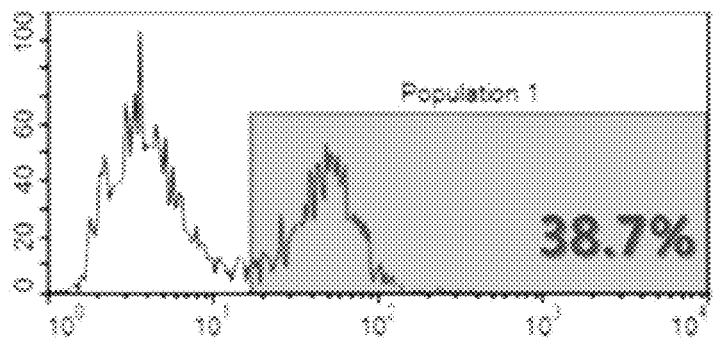

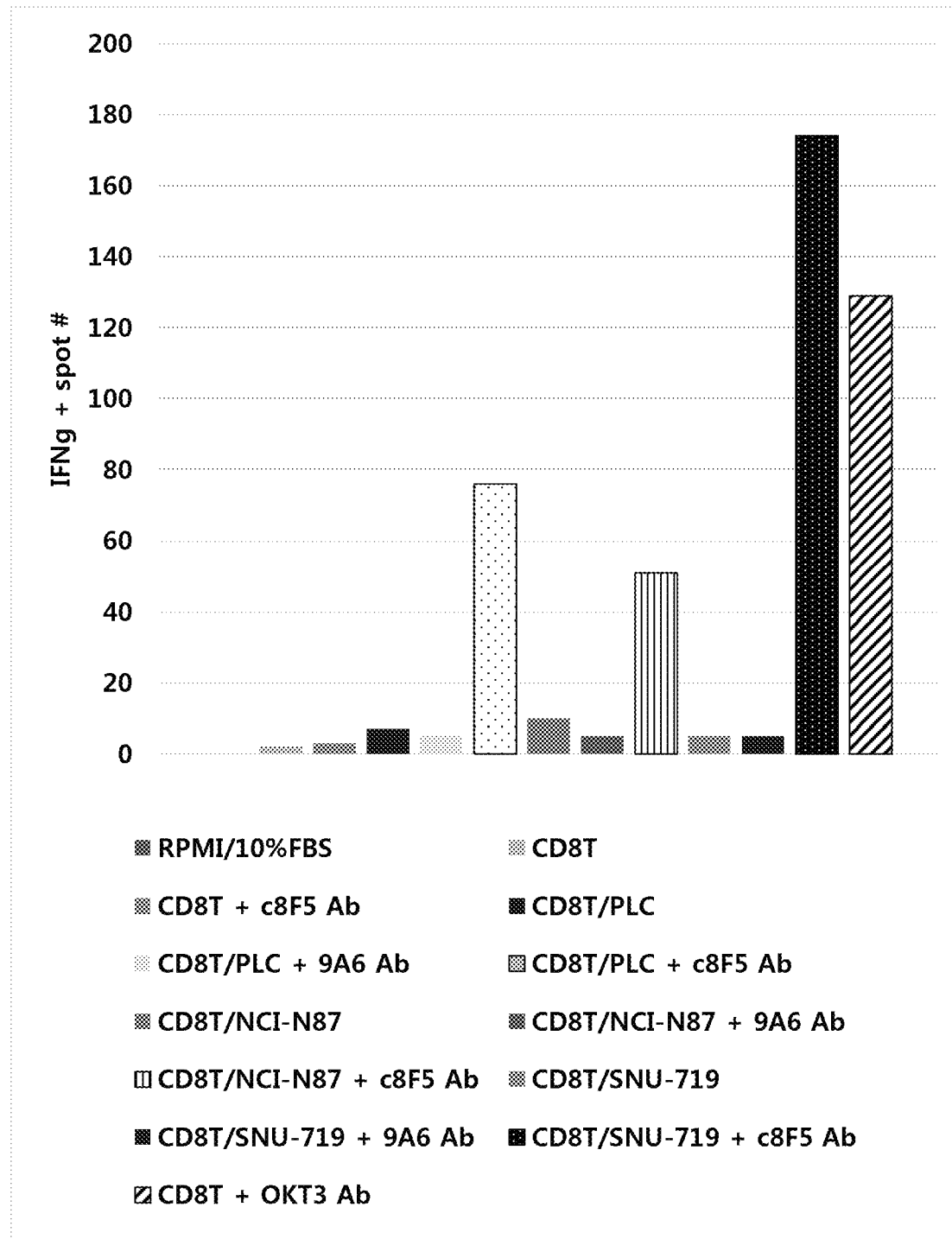
[Fig. 8]

[Fig. 9a]
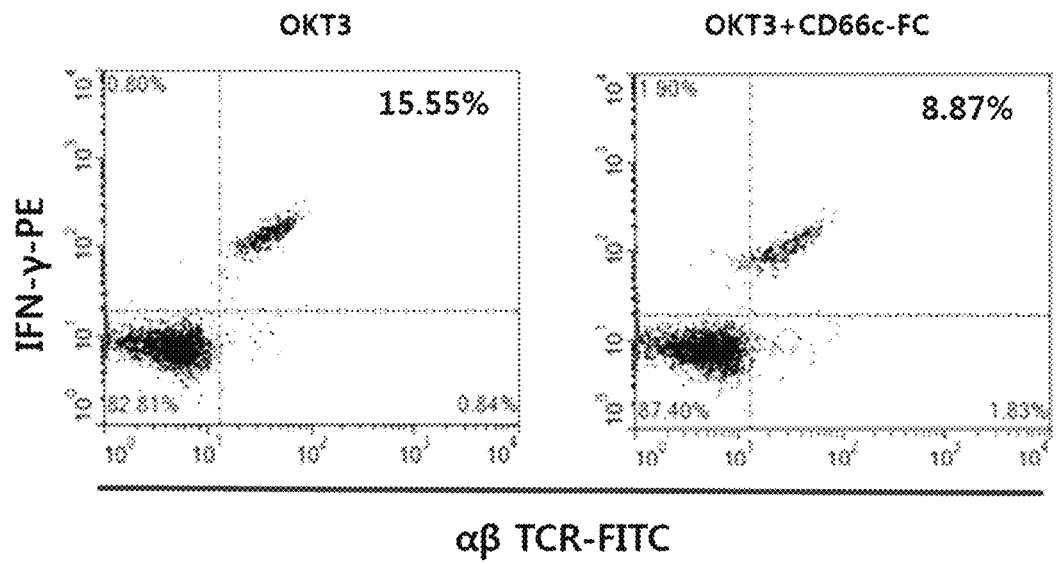
[Fig. 9b]
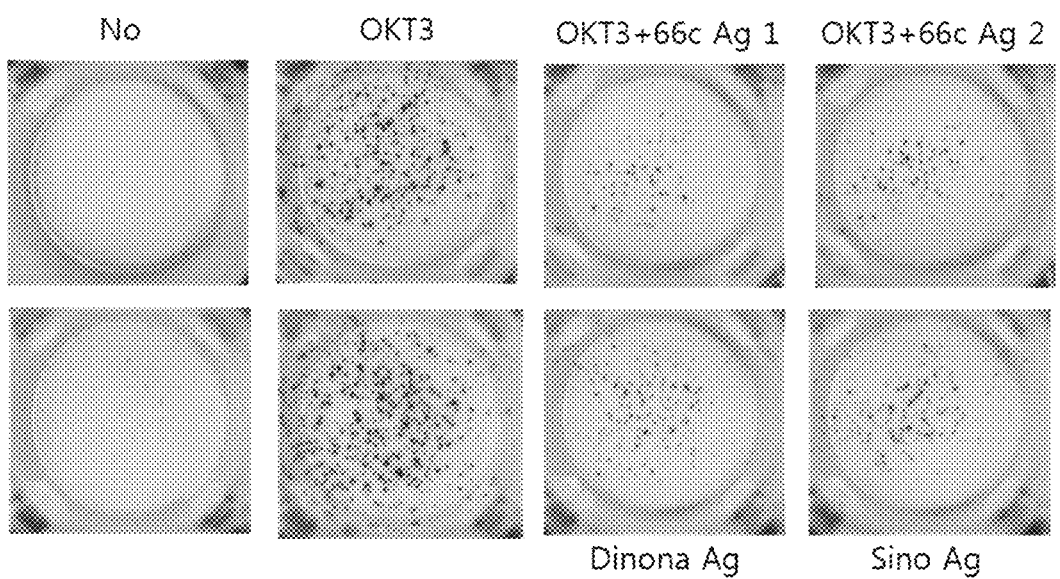

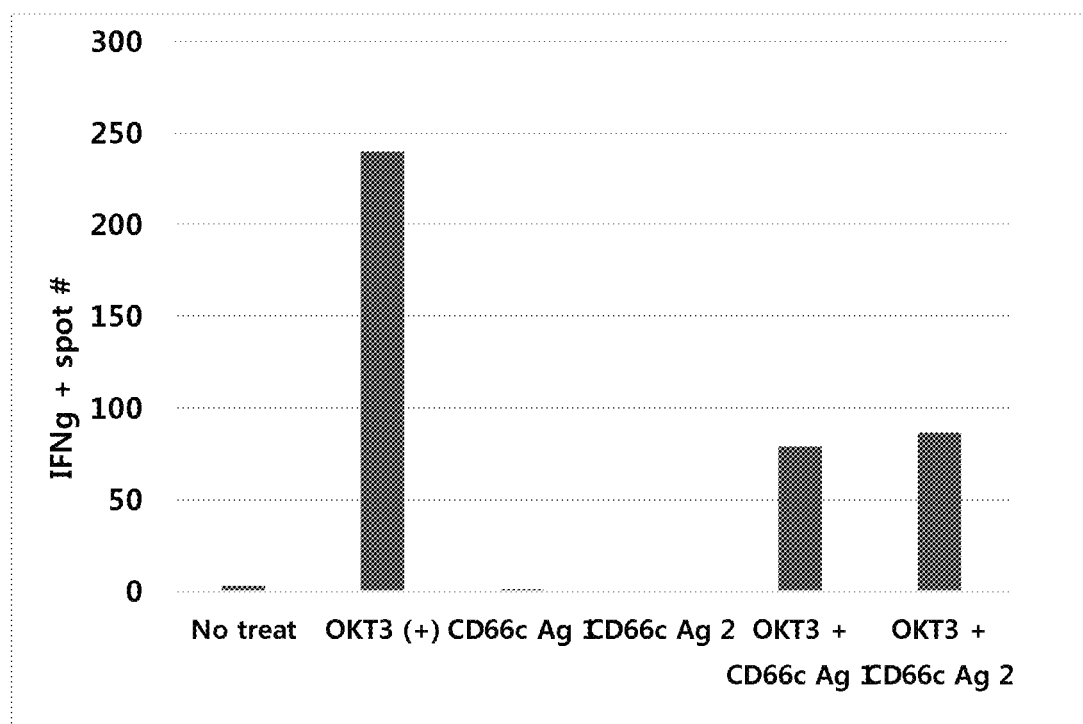
[Fig. 9c]

[Fig. 10a]
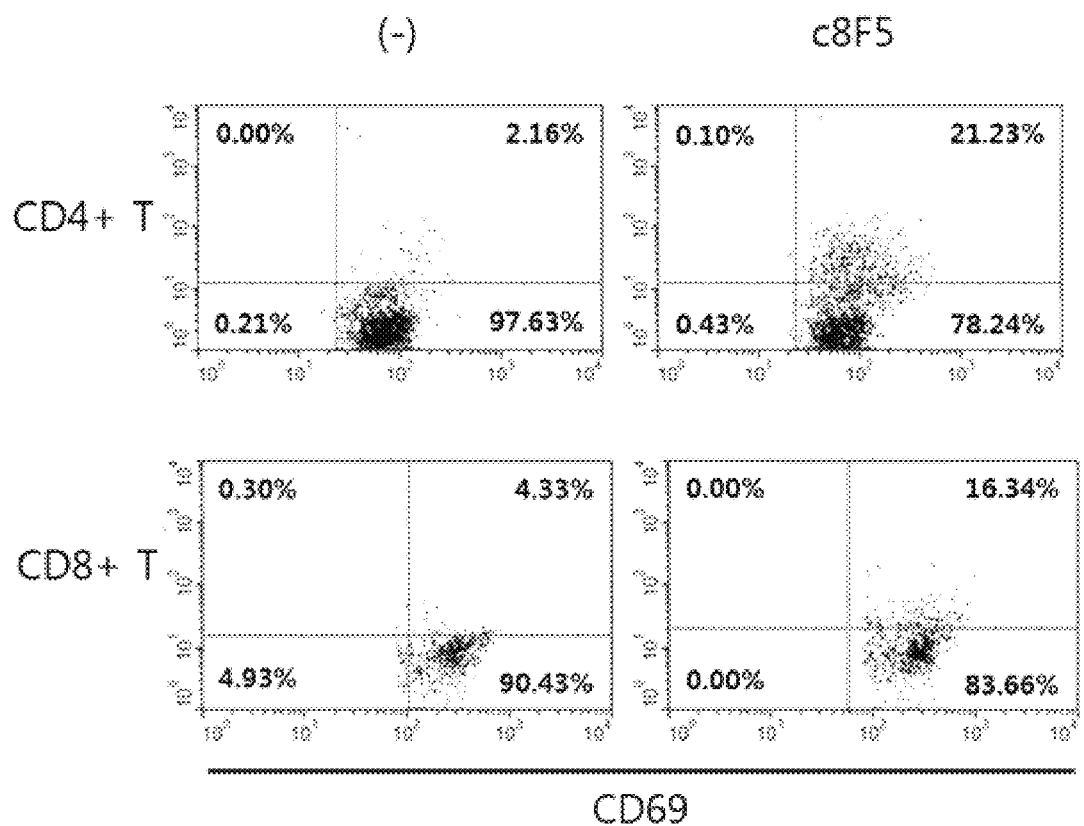

[Fig. 10b]
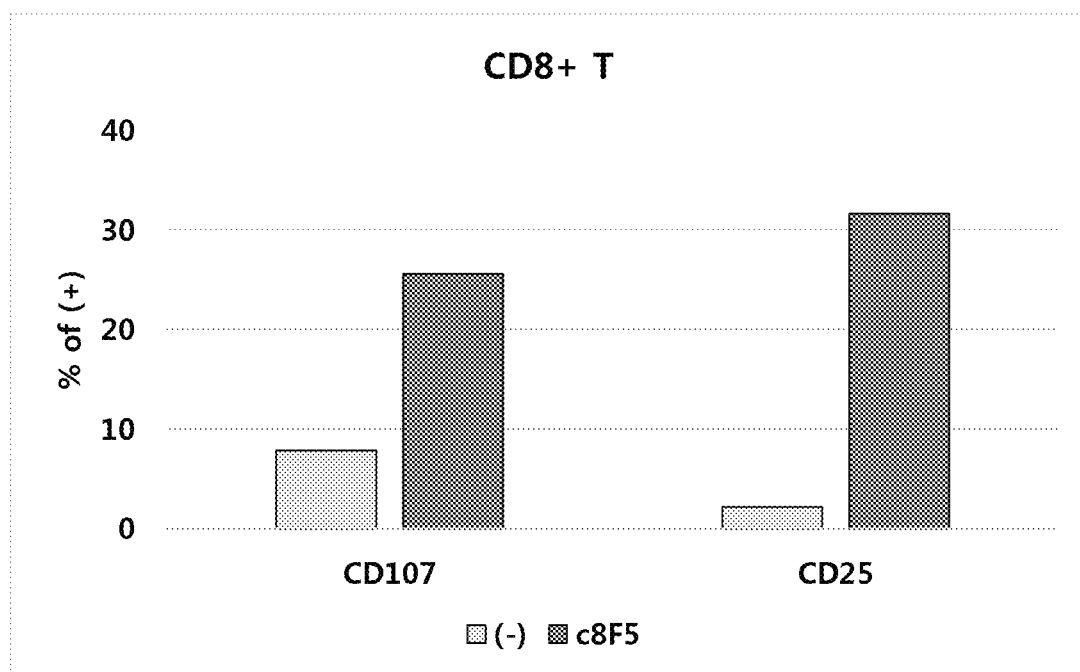

[Fig. 11a]
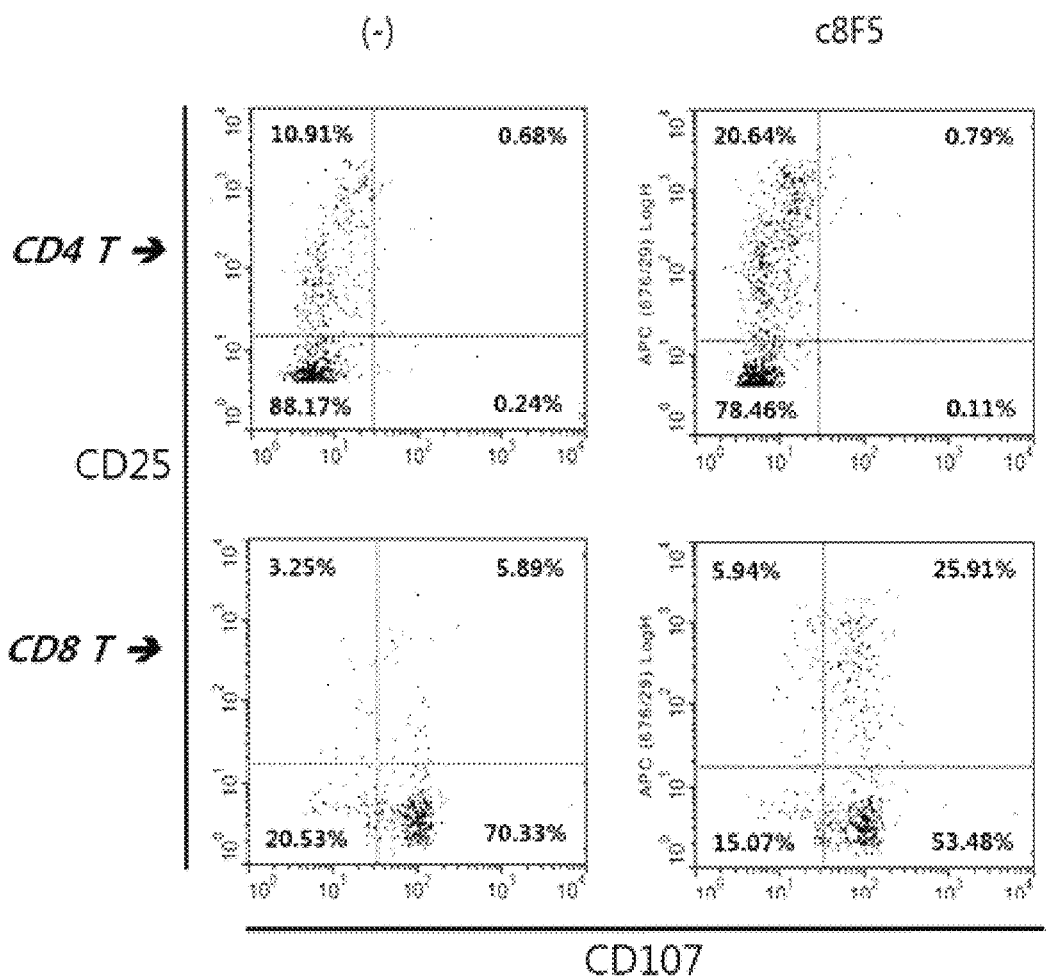

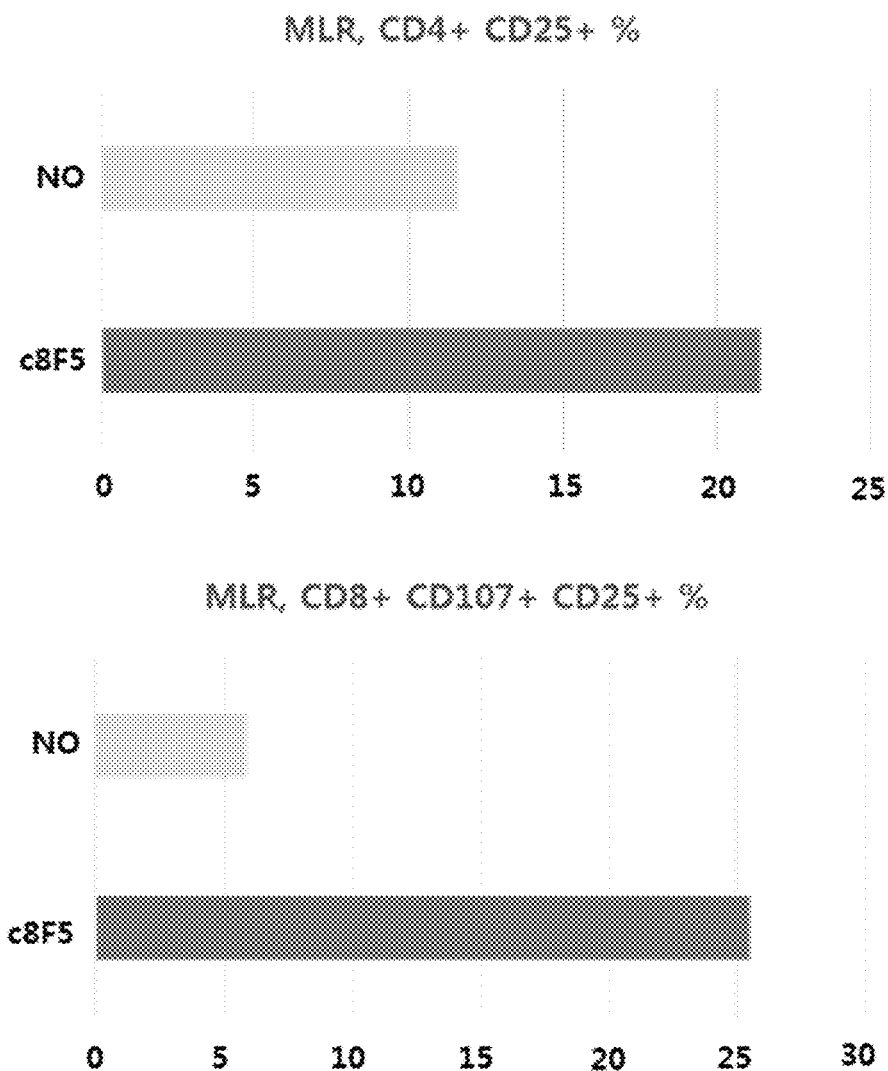
[Fig. 11b]

[Fig. 12a]
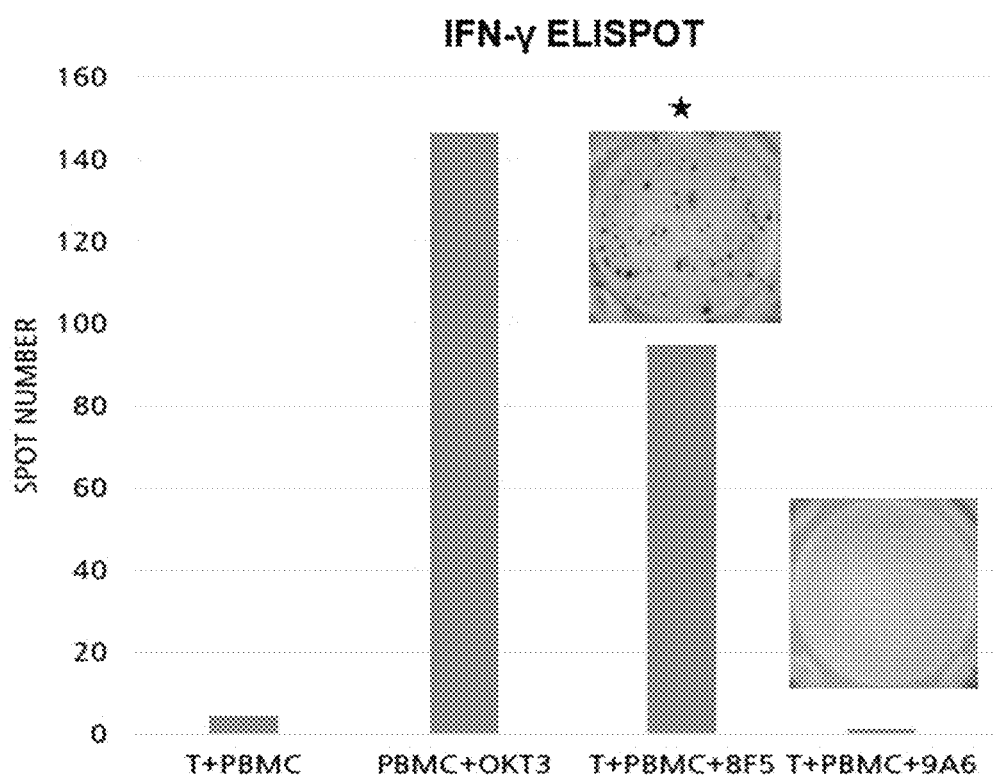

[Fig. 12b]
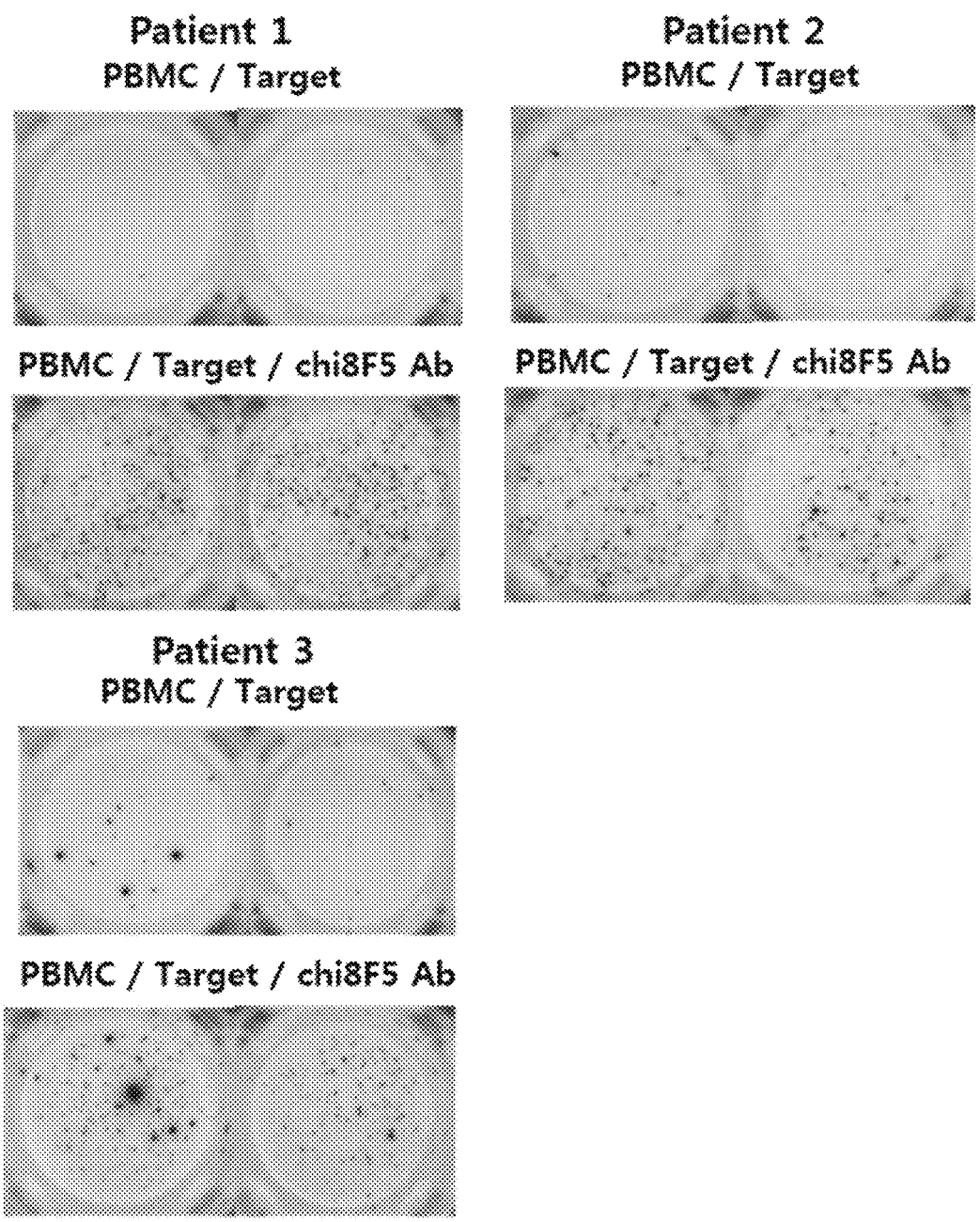

[Fig. 12c]
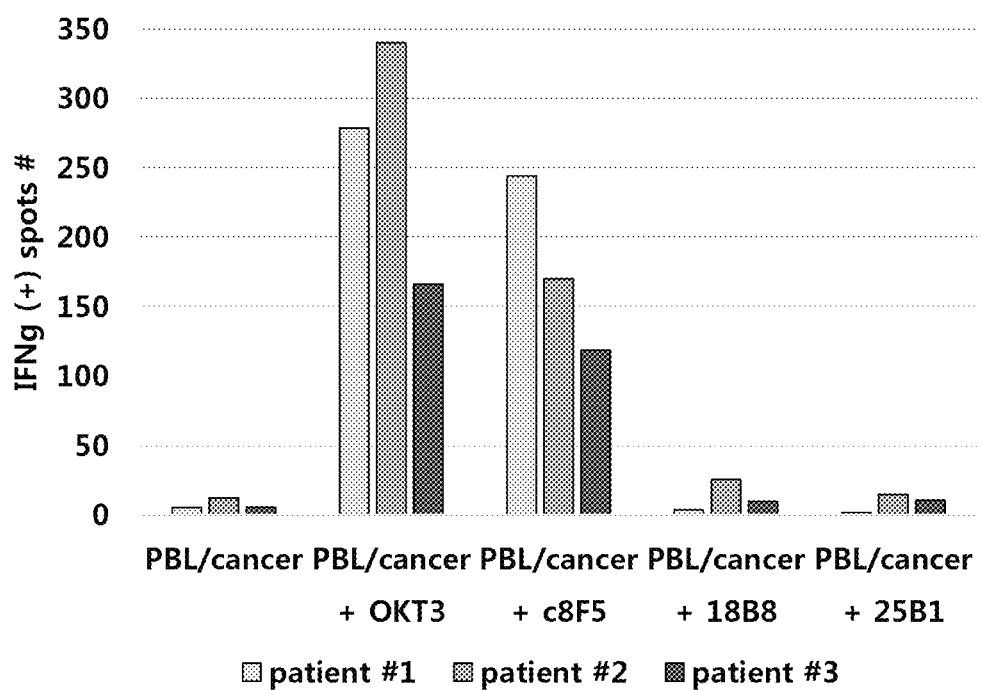

[Fig. 13a]
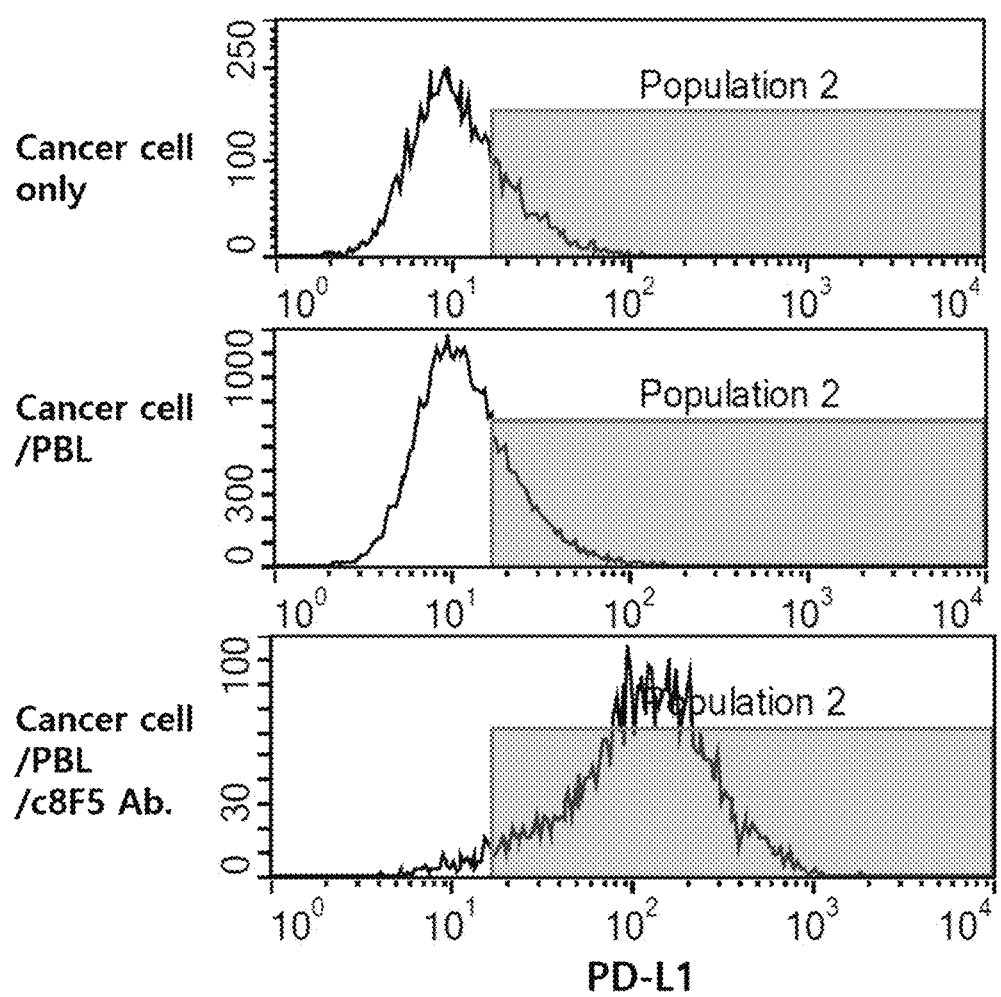

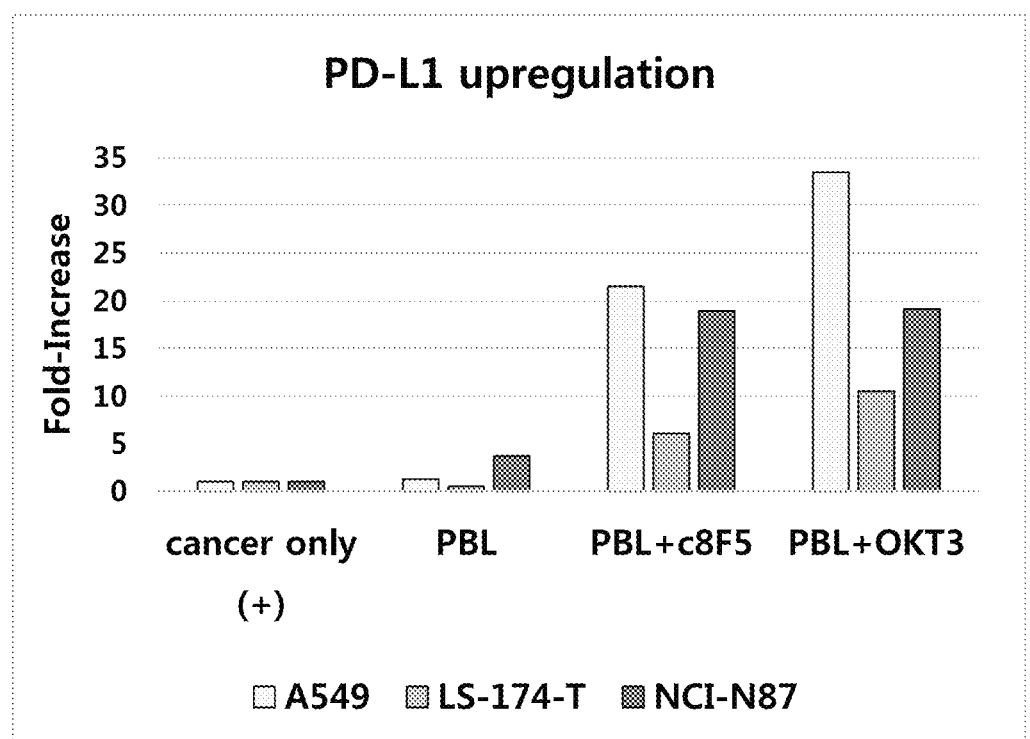
[Fig. 13b]

[Fig. 14a]
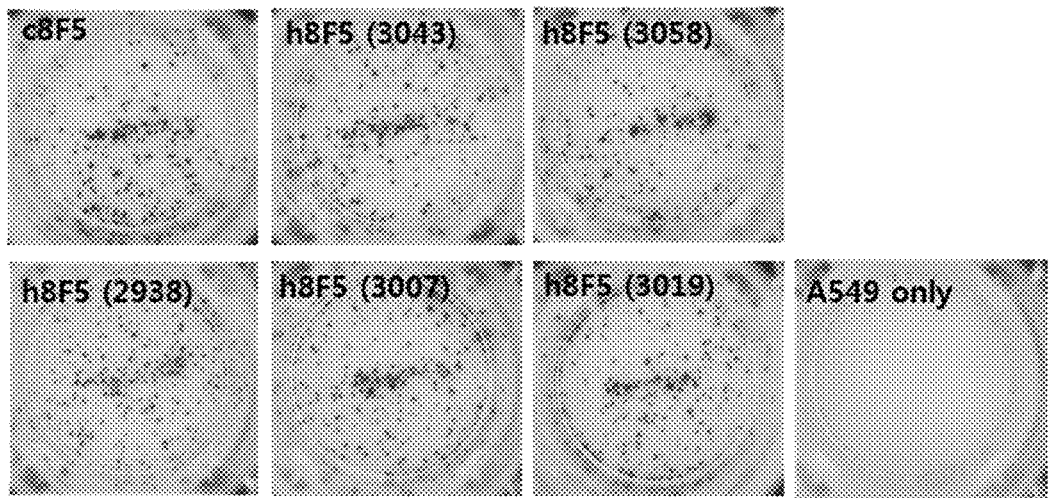
[Fig. 14b]
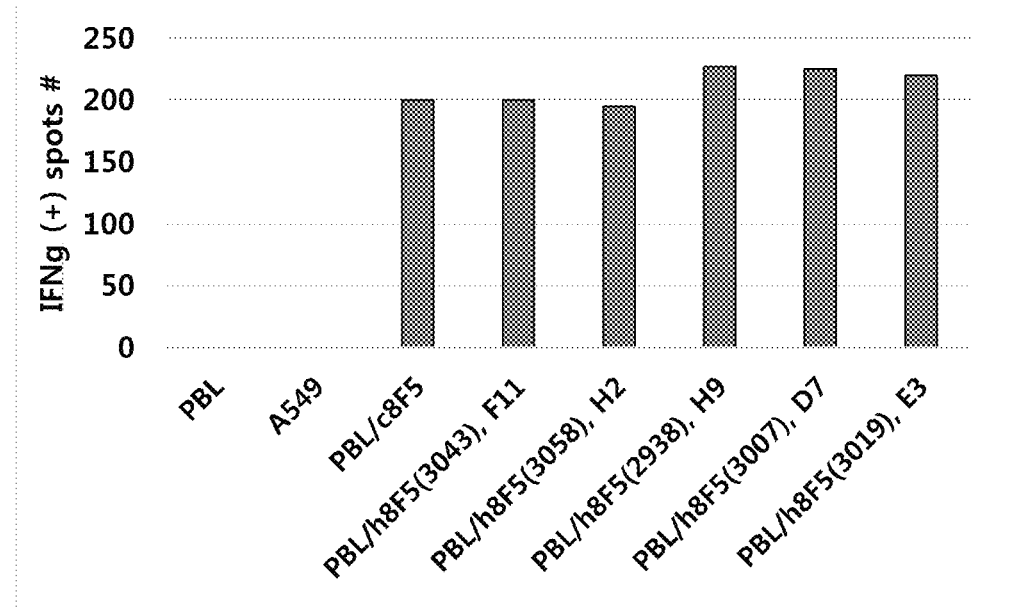

[Fig. 15a]
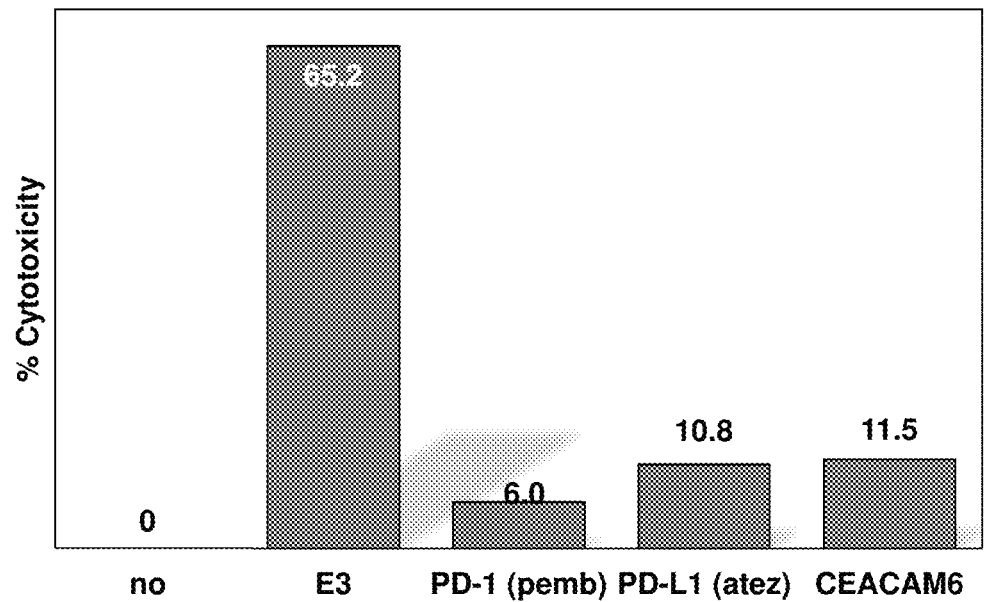
[Fig. 15b]
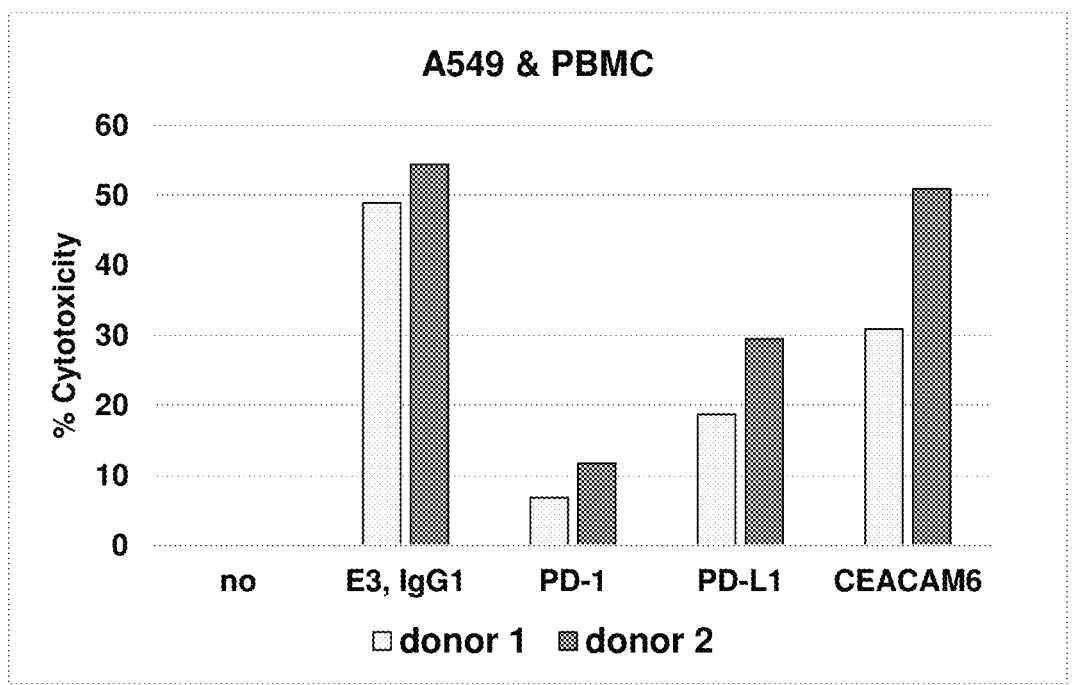

[Fig. 16a]
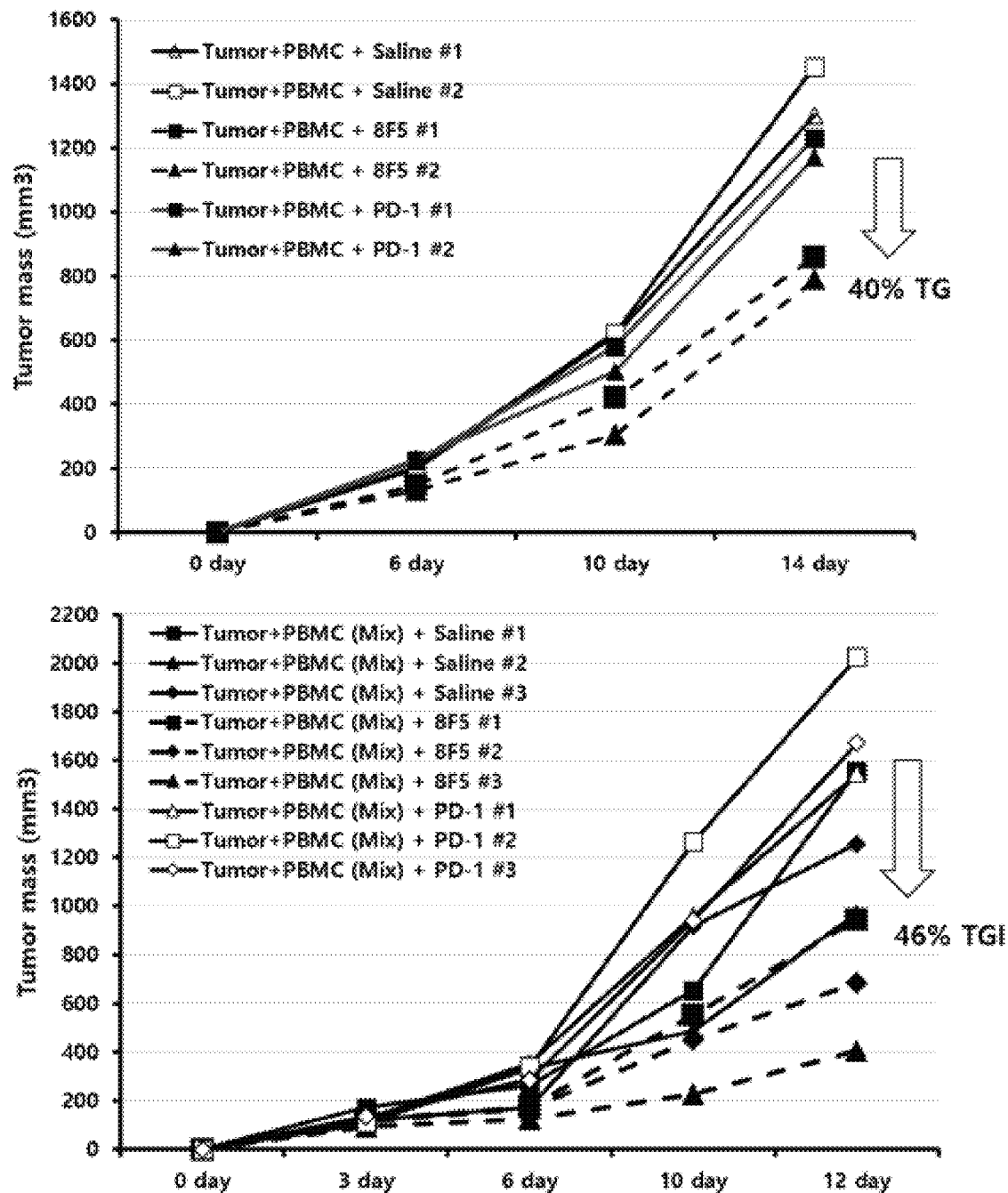

[Fig. 16b]
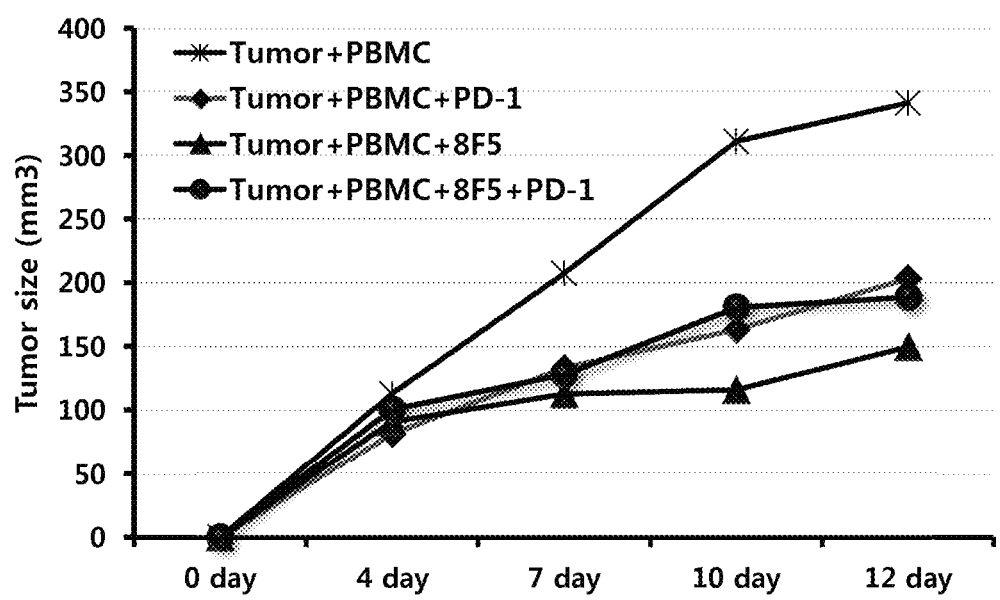

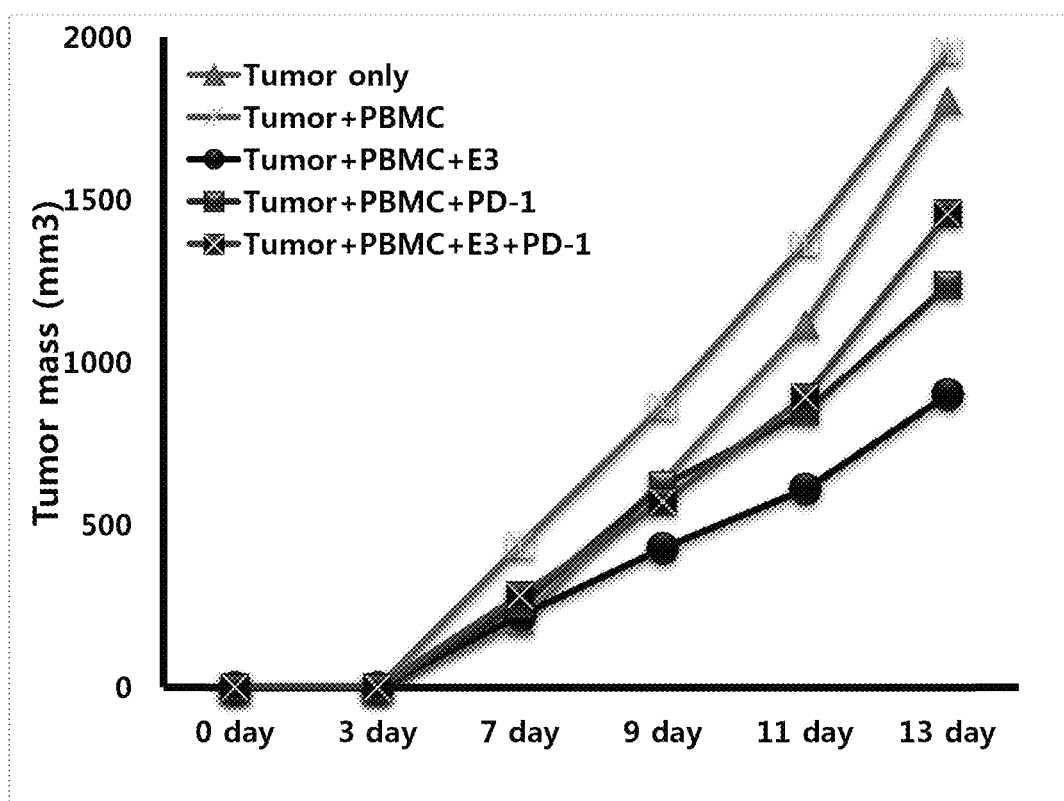
[Fig. 16c]

[Fig. 16d]
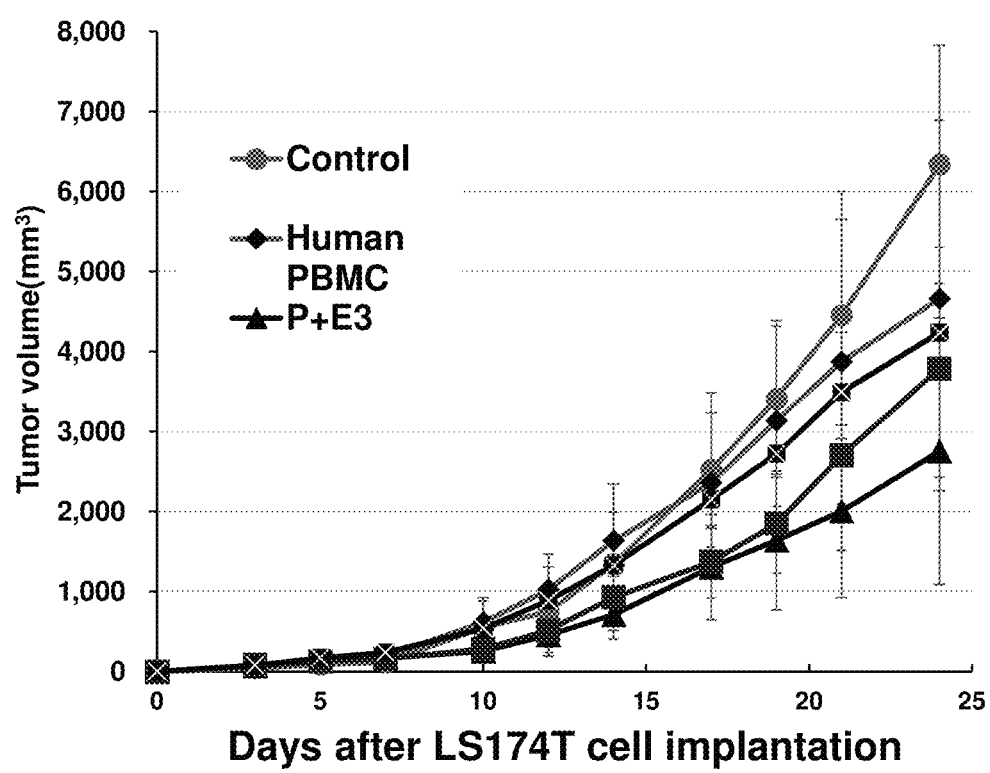

【Fig. 16e】
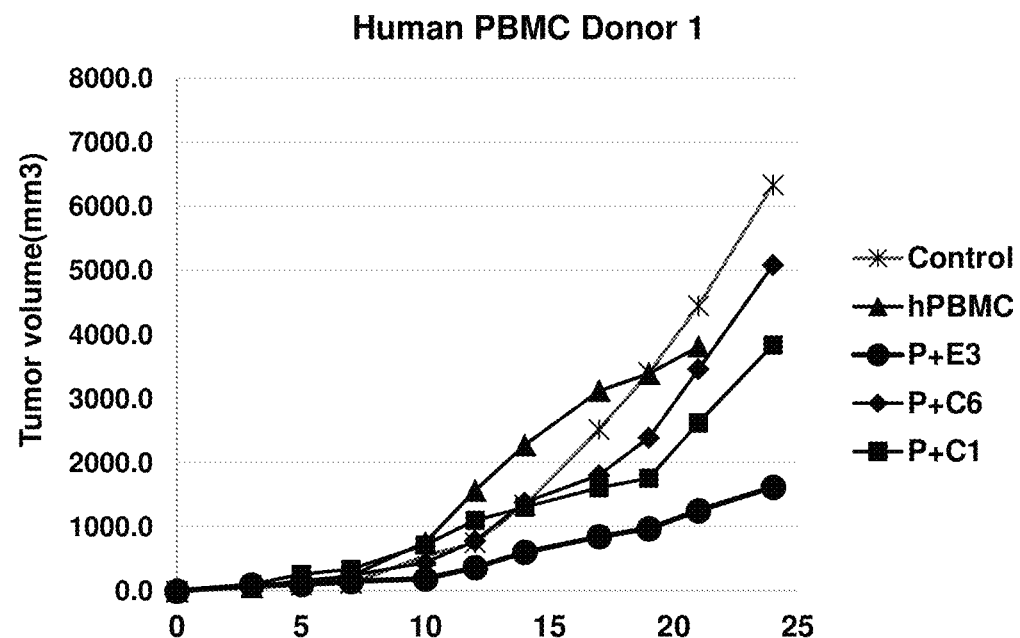
【Fig. 16f】
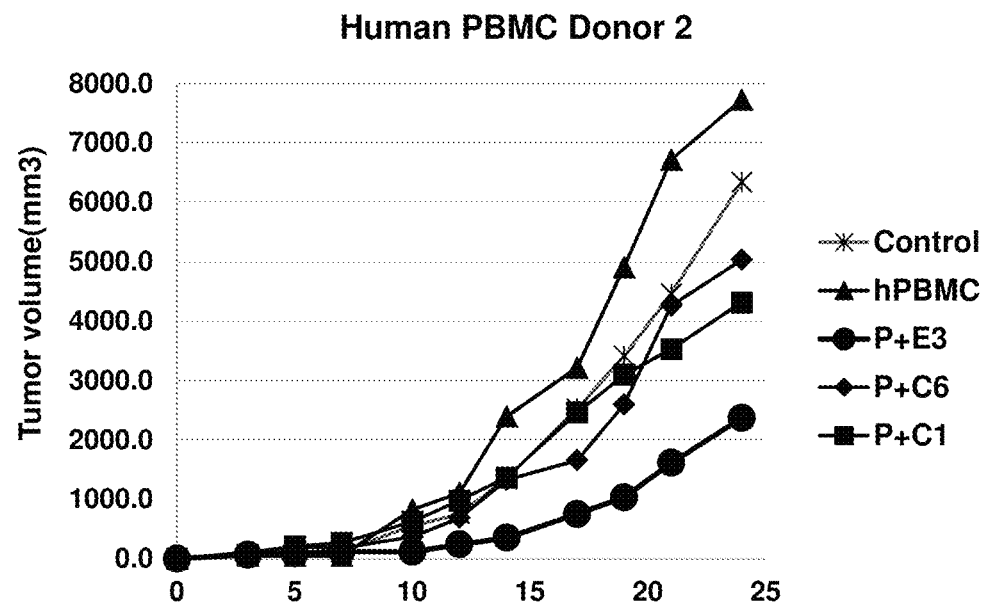

[Fig. 16g]
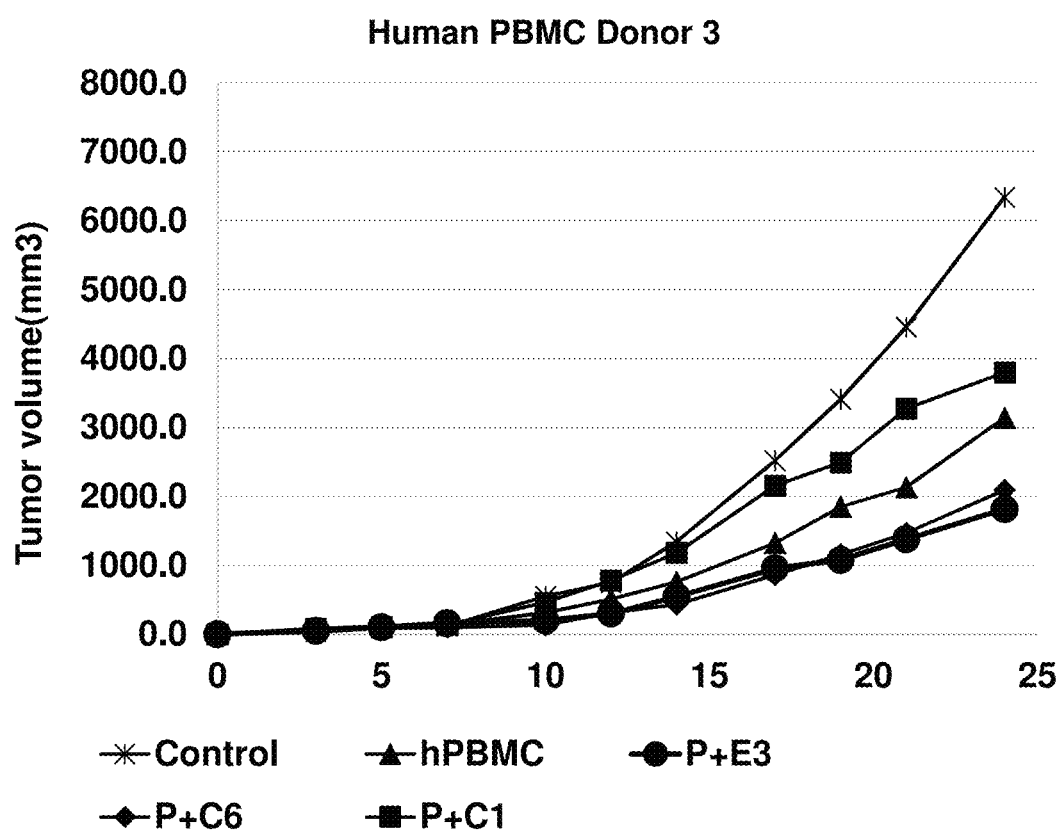

SEQUENCE LISTING

<160> NUMBER OF SEQ ID NOS: 73

<210> SEQ ID NO 1
<211> LENGTH: 12
<212> TYPE: PRT
<213> ORGANISM: Artificial Sequence
<220> FEATURE:
<223> OTHER INFORMATION: CDR-H1 of mouse or chimeric anti-CD66c antibody

<400> SEQUENCE: 1

Ala Ser Gly Tyr Ser Phe Thr Asp Tyr Thr Met Asn
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDR-H2 of mouse or chimeric anti-CD66c antibody

<400> SEQUENCE: 2

Leu Ile Asn Pro Phe His Gly Gly Thr Val Ser Asn Gln Arg Phe Lys
1               5                   10                  15

Val

<210> SEQ ID NO 3
<211> LENGTH: 14
<212> TYPE: PRT
<213> ORGANISM: Artificial Sequence
<220> FEATURE:
<223> OTHER INFORMATION: CDR-H3 of mouse or chimeric anti-CD66c antibody

<400> SEQUENCE: 3

Val Arg Gly Asp Pro Val Arg His Tyr Tyr Ala Leu Ala Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CDR-L1 of mouse or chimeric anti-CD66c antibody

<400> SEQUENCE: 4

Gly Ala Ser Glu Asn Val Tyr Gly Thr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDR-L2 of mouse or chimeric anti-CD66c antibody

<400> SEQUENCE: 5

Gly Ala Thr Asn Leu Ala Asp
1               5

<210> SEQ ID NO 6
<211> LENGTH: 15
<212> TYPE: PRT
<213> ORGANISM: Artificial Sequence
<220> FEATURE:
<223> OTHER INFORMATION: CDR-L3 of mouse or chimeric anti-CD66c antibody

<400> SEQUENCE: 6

Val Ala Thr Tyr Tyr Cys Gln Asn Val Leu Ser Ala Pro Tyr Thr
1               5                   10                  15

<210> SEQ ID NO 7
<211> LENGTH: 121
<212> TYPE: PRT
<213> ORGANISM: Artificial Sequence
<220> FEATURE:
<223> OTHER INFORMATION: Heavy chain variable region of mouse or
      chimeric anti-CD66c antibody

<400> SEQUENCE: 7

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Asp Tyr
            20                  25                  30

Thr Met Asn Trp Val Lys Gln Ser His Gly Lys Asn Leu Glu Trp Ile
        35                  40                  45

Gly Leu Ile Asn Pro Phe His Gly Gly Thr Val Ser Asn Gln Arg Phe
    50                  55                  60

Lys Val Lys Ala Thr Leu Thr Val Asp Val Ser Ser Asn Thr Ala Tyr

```
                65                  70                  75                  80
Met Glu Leu Leu Ser Leu Thr Ser Asp Asp Ser Ala Val Tyr Tyr Cys
                        85                  90                  95

Val Arg Gly Asp Pro Val Arg His Tyr Tyr Ala Leu Ala Tyr Trp Gly
                100                 105                 110

Gln Gly Thr Ser Val Thr Val Ser Ser
        115                 120
```

<210> SEQ ID NO 8
<211> LENGTH: 107
<212> TYPE: PRT
<213> ORGANISM: Artificial Sequence
<220> FEATURE:
<223> OTHER INFORMATION: Light chain variable region of mouse or
      chimeric anti-CD66c antibody

<400> SEQUENCE: 8

```
Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Val Tyr Gly Thr
                20                  25                  30

Leu Asn Trp Tyr Gln Arg Lys Gln Gly Lys Ser Pro Gln Leu Leu Ile
            35                  40                  45

Tyr Gly Ala Thr Asn Leu Ala Asp Gly Met Ser Ser Arg Phe Ser Gly
        50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ser Ala Pro Tyr
                85                  90                  95

Thr Phe Gly Gly Gly Thr Lys Leu Glu Ile Ile
            100                 105
```

<210> SEQ ID NO 9
<211> LENGTH: 12
<212> TYPE: PRT
<213> ORGANISM: Artificial Sequence
<220> FEATURE:
<223> OTHER INFORMATION: CDR-H1 of humanized anti-CD66c antibody

<400> SEQUENCE: 9

```
Ala Ser Gly Tyr Ser Phe Thr Asp Tyr Thr Met His
1               5                   10
```

<210> SEQ ID NO 10
<211> LENGTH: 17
<212> TYPE: PRT
<213> ORGANISM: Artificial Sequence
<220> FEATURE:
<223> OTHER INFORMATION: CDR-H2 of humanized anti-CD66c antibody

<400> SEQUENCE: 10

```
Leu Ile Asn Pro Phe Gly Gly Ser Thr Ser Tyr Ala Gln Lys Phe Lys
1               5                   10                  15

Gly
```

<210> SEQ ID NO 11
<211> LENGTH: 11
<212> TYPE: PRT
<213> ORGANISM: Artificial Sequence
<220> FEATURE:
<223> OTHER INFORMATION: CDR-L1 of humanized anti-CD66c antibody

```
<400> SEQUENCE: 11

Gly Ala Ser Glu Asn Val Tyr Gly Thr Leu Ala
1               5                   10

<210> SEQ ID NO 12
<211> LENGTH: 11
<212> TYPE: PRT
<213> ORGANISM: Artificial Sequence
<220> FEATURE:
<223> OTHER INFORMATION: CDR-L1 of humanized anti-CD66c antibody

<400> SEQUENCE: 12

Arg Ala Ser Glu Asn Val Tyr Gly Thr Leu Asn
1               5                   10

<210> SEQ ID NO 13
<211> LENGTH: 15
<212> TYPE: PRT
<213> ORGANISM: Artificial Sequence
<220> FEATURE:
<223> OTHER INFORMATION: CDR-L3 of humanized anti-CD66c antibody

<400> SEQUENCE: 13

Phe Ala Thr Tyr Tyr Cys Gln Asn Val Leu Ser Ala Pro Tyr Thr
1               5                   10                  15

<210> SEQ ID NO 14
<211> LENGTH: 128
<212> TYPE: PRT
<213> ORGANISM: Artificial Sequence
<220> FEATURE:
<223> OTHER INFORMATION: Heavy chain variable region of humanized anti-
      CD66c antibody (8F5-human-VH5)

<400> SEQUENCE: 14

Phe His Met Ala Asn Val His Gln Val Gln Leu Val Gln Ser Gly Ala
1               5                   10                  15

Glu Val Lys Lys Pro Gly Ala Ser Val Lys Ile Ser Cys Lys Ala Ser
            20                  25                  30

Gly Tyr Ser Phe Thr Asp Tyr Thr Met Asn Trp Val Arg Gln Ala His
        35                  40                  45

Gly Gln Asn Leu Glu Trp Ile Gly Leu Ile Asn Pro Phe His Gly Gly
    50                  55                  60

Thr Val Ser Asn Gln Arg Phe Lys Val Lys Ala Thr Leu Thr Val Asp
65                  70                  75                  80

Val Ser Thr Asn Thr Ala Tyr Met Glu Leu Ser Arg Leu Arg Ser Asp
                85                  90                  95

Asp Thr Ala Val Tyr Tyr Cys Val Arg Gly Asp Pro Val Arg His Tyr
            100                 105                 110

Tyr Ala Leu Ala Tyr Trp Gly Gln Gly Thr Leu Val Thr Val Ser Ser
        115                 120                 125

<210> SEQ ID NO 15
<211> LENGTH: 121
<212> TYPE: PRT
<213> ORGANISM: Artificial Sequence
<220> FEATURE:
<223> OTHER INFORMATION: Heavy chain variable region of humanized anti-
      CD66c antibody (8F5-human-VH6)

<400> SEQUENCE: 15

Gln Val Gln Leu Val Gln Ser Gly Ala Glu Val Lys Lys Pro Gly Ala
1               5                   10                  15
```

```
Ser Met Lys Ile Ser Cys Lys Ala Ser Gly Tyr Ser Phe Thr Asp Tyr
            20                  25                  30

Thr Met Asn Trp Val Lys Gln Ala Pro Gly Gln Asn Leu Glu Trp Ile
        35                  40                  45

Gly Leu Ile Asn Pro Phe His Gly Gly Thr Val Ser Asn Gln Arg Phe
    50                  55                  60

Lys Val Lys Ala Thr Leu Thr Val Asp Val Ser Thr Asn Thr Ala Tyr
65                  70                  75                  80

Met Glu Leu Ser Arg Leu Arg Ser Asp Asp Thr Ala Val Tyr Tyr Cys
                85                  90                  95

Val Arg Gly Asp Pro Val Arg His Tyr Tyr Ala Leu Ala Tyr Trp Gly
            100                 105                 110

Gln Gly Thr Leu Val Thr Val Ser Ser
        115                 120

<210> SEQ ID NO 16
<211> LENGTH: 121
<212> TYPE: PRT
<213> ORGANISM: Artificial Sequence
<220> FEATURE:
<223> OTHER INFORMATION: Heavy chain variable region of humanized anti-
      CD66c antibody (8F5-human-VH7)

<400> SEQUENCE: 16

Gln Val Gln Leu Val Gln Ser Gly Ala Glu Val Lys Lys Pro Gly Ala
1               5                   10                  15

Ser Met Lys Ile Ser Cys Lys Ala Ser Gly Tyr Ser Phe Thr Asp Tyr
            20                  25                  30

Thr Met Asn Trp Val Arg Gln Ala Pro Gly Gln Gly Leu Glu Trp Ile
        35                  40                  45

Gly Leu Ile Asn Pro Phe His Gly Gly Thr Val Ser Asn Gln Arg Phe
    50                  55                  60

Lys Val Lys Ala Thr Leu Thr Val Asp Val Ser Thr Asn Thr Ala Tyr
65                  70                  75                  80

Met Glu Leu Ser Arg Leu Arg Ser Asp Asp Thr Ala Val Tyr Tyr Cys
                85                  90                  95

Val Arg Gly Asp Pro Val Arg His Tyr Tyr Ala Leu Ala Tyr Trp Gly
            100                 105                 110

Gln Gly Thr Leu Val Thr Val Ser Ser
        115                 120

<210> SEQ ID NO 17
<211> LENGTH: 121
<212> TYPE: PRT
<213> ORGANISM: Artificial Sequence
<220> FEATURE:
<223> OTHER INFORMATION: Heavy chain variable region of humanized anti-
      CD66c antibody (8F5-human-VH10)

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Thr Met Asn Trp Val Lys Gln Ala Pro Gly Gln Asn Leu Glu Trp Ile
        35                  40                  45

Gly Leu Ile Asn Pro Phe His Gly Gly Thr Val Ser Asn Gln Arg Phe
    50                  55                  60
```

Lys Val Lys Ala Thr Met Thr Val Asp Val Ser Thr Asn Thr Ala Tyr
65                  70                  75                  80

Met Glu Leu Ser Arg Leu Arg Ser Asp Asp Thr Ala Val Tyr Tyr Cys
            85                  90                  95

Val Arg Gly Asp Pro Val Arg His Tyr Tyr Ala Leu Ala Tyr Trp Gly
            100                 105                 110

Gln Gly Thr Leu Val Thr Val Ser Ser
        115                 120

<210> SEQ ID NO 18
<211> LENGTH: 121
<212> TYPE: PRT
<213> ORGANISM: Artificial Sequence
<220> FEATURE:
<223> OTHER INFORMATION: Heavy chain variable region of humanized anti-
      CD66c antibody (8F5-human-VH11)

<400> SEQUENCE: 18

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Asp Tyr
            20                  25                  30

Thr Met His Trp Val Lys Gln Ala Pro Gly Gln Asn Leu Glu Trp Ile
        35                  40                  45

Gly Leu Ile Asn Pro Phe Gly Gly Ser Thr Ser Tyr Ala Gln Lys Phe
    50                  55                  60

Lys Gly Arg Val Thr Met Thr Arg Asp Thr Ser Thr Asn Thr Ala Tyr
65                  70                  75                  80

Met Glu Leu Ser Arg Leu Arg Ser Asp Asp Thr Ala Val Tyr Tyr Cys
            85                  90                  95

Val Arg Gly Asp Pro Val Arg His Tyr Tyr Ala Leu Ala Tyr Trp Gly
            100                 105                 110

Gln Gly Thr Leu Val Thr Val Ser Ser
        115                 120

<210> SEQ ID NO 19
<211> LENGTH: 107
<212> TYPE: PRT
<213> ORGANISM: Artificial Sequence
<220> FEATURE:
<223> OTHER INFORMATION: Light chain variable region of humanized anti-
      CD66c antibody (8F5-human-VK5)

<400> SEQUENCE: 19

Asp Ile Gln Met Thr Gln Ser Pro Ser Thr Leu Ser Ala Ser Val Gly
1               5                   10                  15

Asp Arg Val Thr Ile Thr Cys Gly Ala Ser Glu Asn Val Tyr Gly Thr
            20                  25                  30

Leu Ala Trp Tyr Gln Arg Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Arg Glu Tyr Thr Leu Thr Ile Ser Ser Leu Gln Pro
65                  70                  75                  80

Asp Asp Phe Ala Thr Tyr Tyr Cys Gln Asn Val Leu Ser Ala Pro Tyr
            85                  90                  95

Thr Phe Gly Gly Gly Thr Lys Leu Glu Ile Lys
            100                 105

```
<210> SEQ ID NO 20
<211> LENGTH: 107
<212> TYPE: PRT
<213> ORGANISM: Artificial Sequence
<220> FEATURE:
<223> OTHER INFORMATION: Light chain variable region of humanized anti-
      CD66c antibody (8F5-human-VK7)

<400> SEQUENCE: 20

Asp Ile Gln Met Thr Gln Ser Pro Ser Thr Leu Ser Ala Ser Val Gly
1               5                   10                  15

Asp Arg Val Thr Ile Thr Cys Gly Ala Ser Glu Asn Val Tyr Gly Thr
            20                  25                  30

Leu Asn Trp Tyr Gln Arg Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Asn Val Leu Ser Ala Pro Tyr
                85                  90                  95

Thr Phe Gly Gly Gly Thr Lys Leu Glu Ile Lys
            100                 105

<210> SEQ ID NO 21
<211> LENGTH: 107
<212> TYPE: PRT
<213> ORGANISM: Artificial Sequence
<220> FEATURE:
<223> OTHER INFORMATION: Light chain variable region of humanized anti-
      CD66c antibody (8F5-human-VK8)

<400> SEQUENCE: 21

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Asn Val Tyr Gly Thr
            20                  25                  30

Leu Asn Trp Tyr Gln Arg Lys Pro Gly Lys Ala Pro Lys Leu Leu Ile
        35                  40                  45

Tyr Gly Ala Thr Asn Leu Ala Asp Gly Met Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Asn Val Leu Ser Ala Pro Tyr
                85                  90                  95

Thr Phe Gly Gly Gly Thr Lys Leu Glu Ile Lys
            100                 105

<210> SEQ ID NO 22
<211> LENGTH: 23
<212> TYPE: PRT
<213> ORGANISM: Artificial Sequence
<220> FEATURE:
<223> OTHER INFORMATION: Framework 1 in Heavy chain variable region of
      chimeric anti-CD66c antibody

<400> SEQUENCE: 22

Glu Val Gln Leu Gln Gln Ser Gly Pro Glu Leu Val Lys Pro Gly Ala
1               5                   10                  15
```

Ser Met Lys Ile Ser Cys Lys
            20

<210> SEQ ID NO 23
<211> LENGTH: 23
<212> TYPE: PRT
<213> ORGANISM: Artificial Sequence
<220> FEATURE:
<223> OTHER INFORMATION: Framework 1 in Heavy chain variable region of
      humanized anti-CD66c antibody (8F5-human-VH5)

<400> SEQUENCE: 23

Gln Val Gln Leu Val Gln Ser Gly Ala Glu Val Lys Lys Pro Gly Ala
1               5                   10                  15

Ser Val Lys Ile Ser Cys Lys
            20

<210> SEQ ID NO 24
<211> LENGTH: 23
<212> TYPE: PRT
<213> ORGANISM: Artificial Sequence
<220> FEATURE:
<223> OTHER INFORMATION: Framework 1 in Heavy chain variable region of
      humanized anti-CD66c antibody (8F5-human-VH6)

<400> SEQUENCE: 24

Gln Val Gln Leu Val Gln Ser Gly Ala Glu Val Lys Lys Pro Gly Ala
1               5                   10                  15

Ser Met Lys Ile Ser Cys Lys
            20

<210> SEQ ID NO 25
<211> LENGTH: 23
<212> TYPE: PRT
<213> ORGANISM: Artificial Sequence
<220> FEATURE:
<223> OTHER INFORMATION: Framework 1 in Heavy chain variable region of
      humanized anti-CD66c antibody (8F5-human-VH7)

<400> SEQUENCE: 25

Gln Val Gln Leu Val Gln Ser Gly Ala Glu Val Lys Lys Pro Gly Ala
1               5                   10                  15

Ser Met Lys Ile Ser Cys Lys
            20

<210> SEQ ID NO 26
<211> LENGTH: 23
<212> TYPE: PRT
<213> ORGANISM: Artificial Sequence
<220> FEATURE:
<223> OTHER INFORMATION: Framework 1 in Heavy chain variable region of
      humanized anti-CD66c antibody (8F5-human-VH10)

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys
            20

<210> SEQ ID NO 27
<211> LENGTH: 23
<212> TYPE: PRT
<213> ORGANISM: Artificial Sequence
<220> FEATURE:
<223> OTHER INFORMATION: Framework 1 in Heavy chain variable region of
      humanized anti-CD66c antibody (8F5-human-VH11)

```
<400> SEQUENCE: 27

Gln Val Gln Leu Val Gln Ser Gly Ala Glu Val Lys Lys Pro Gly Ala
1               5                   10                  15

Ser Val Lys Ile Ser Cys Lys
            20

<210> SEQ ID NO 28
<211> LENGTH: 23
<212> TYPE: PRT
<213> ORGANISM: Artificial Sequence
<220> FEATURE:
<223> OTHER INFORMATION: Framework 1 in Light chain variable region of
      chimeric anti-CD66c antibody

<400> SEQUENCE: 28

Asp Ile Gln Met Thr Gln Ser Pro Ala Ser Leu Ser Ala Ser Val Gly
1               5                   10                  15

Glu Thr Val Thr Ile Thr Cys
            20

<210> SEQ ID NO 29
<211> LENGTH: 23
<212> TYPE: PRT
<213> ORGANISM: Artificial Sequence
<220> FEATURE:
<223> OTHER INFORMATION: Framework 1 in Light chain variable region of
      humanized anti-CD66c antibody (8F5-human-VK5)

<400> SEQUENCE: 29

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 30
<211> LENGTH: 23
<212> TYPE: PRT
<213> ORGANISM: Artificial Sequence
<220> FEATURE:
<223> OTHER INFORMATION: Framework 1 in Light chain variable region of
      humanized anti-CD66c antibody (8F5-human-VK7)

<400> SEQUENCE: 30

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 31
<211> LENGTH: 23
<212> TYPE: PRT
<213> ORGANISM: Artificial Sequence
<220> FEATURE:
<223> OTHER INFORMATION: Framework 1 in Light chain variable region of
      humanized anti-CD66c antibody (8F5-human-VK8)

<400> SEQUENCE: 31

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 32
```

```
<211> LENGTH: 14
<212> TYPE: PRT
<213> ORGANISM: Artificial Sequence
<220> FEATURE:
<223> OTHER INFORMATION: Framework 2 in Heavy chain variable regionof
      chimeric anti-CD66c antibody

<400> SEQUENCE: 32

Trp Val Lys Gln Ser His Gly Lys Asn Leu Glu Trp Ile Gly
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Framework 2 in Heavy chain variable region of
      humanized anti-CD66c antibody (8F5-human-VH5)

<400> SEQUENCE: 33

Trp Val Arg Gln Ala His Gly Gln Asn Leu Glu Trp Ile Gly
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Framework 2 in Heavy chain variable region of
      humanized anti-CD66c antibody (8F5-human-VH6)

<400> SEQUENCE: 34

Trp Val Lys Gln Ala Pro Gly Gln Asn Leu Glu Trp Ile Gly
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Framework 2 in Heavy chain variable region of
      humanized anti-CD66c antibody (8F5-human-VH7)

<400> SEQUENCE: 35

Trp Val Arg Gln Ala Pro Gly Gln Gly Leu Glu Trp Ile Gly
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Framework 2 in Heavy chain variable region of
      humanized anti-CD66c antibody (8F5-human-VH10)

<400> SEQUENCE: 36

Trp Val Lys Gln Ala Pro Gly Gln Asn Leu Glu Trp Ile Gly
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Framework 2 in Heavy chain variable region of
      humanized anti-CD66c antibody (8F5-human-VH11)

<400> SEQUENCE: 37
```

Trp Val Lys Gln Ala Pro Gly Gln Asn Leu Glu Trp Ile Gly
1               5                   10

<210> SEQ ID NO 38
<211> LENGTH: 15
<212> TYPE: PRT
<213> ORGANISM: Artificial Sequence
<220> FEATURE:
<223> OTHER INFORMATION: Framework 2 in Light chain variable region of
      chimeric anti-CD66c antibody

<400> SEQUENCE: 38

Trp Tyr Gln Arg Lys Gln Gly Lys Ser Pro Gln Leu Leu Ile Tyr
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Framework 2 in Light chain variable region of
      humanized anti-CD66c antibody (8F5-human-VK5)

<400> SEQUENCE: 39

Trp Tyr Gln Arg Lys Pro Gly Lys Ala Pro Lys Leu Leu Ile Tyr
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Framework 2 in Light chain variable region of
      humanized anti-CD66c antibody (8F5-human-VK6)

<400> SEQUENCE: 40

Trp Tyr Gln Arg Lys Pro Gly Lys Ala Pro Lys Leu Leu Ile Tyr
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Framework 2 in Light chain variable region of
      humanized anti-CD66c antibody (8F5-human-VK8)

<400> SEQUENCE: 41

Trp Tyr Gln Arg Lys Pro Gly Lys Ala Pro Lys Leu Leu Ile Tyr
1               5                   10                  15

<210> SEQ ID NO 42
<211> LENGTH: 38
<212> TYPE: PRT
<213> ORGANISM: Artificial Sequence
<220> FEATURE:
<223> OTHER INFORMATION: Framework 3 in Heavy chain variable region of
      chimeric anti-CD66c antibody

<400> SEQUENCE: 42

Asn Gln Arg Phe Lys Val Lys Ala Thr Leu Thr Val Asp Val Ser Ser
1               5                   10                  15

Asn Thr Ala Tyr Met Glu Leu Leu Ser Leu Thr Ser Asp Asp Ser Ala
                20                  25                  30

Val Tyr Tyr Cys Val Arg
            35

```
<210> SEQ ID NO 43
<211> LENGTH: 38
<212> TYPE: PRT
<213> ORGANISM: Artificial Sequence
<220> FEATURE:
<223> OTHER INFORMATION: Framework 3 in Heavy chain variable region of
      humanized anti-CD66c antibody (8F5-human-VH5)

<400> SEQUENCE: 43

Asn Gln Arg Phe Lys Val Lys Ala Thr Leu Thr Val Asp Val Ser Thr
1               5                   10                  15

Asn Thr Ala Tyr Met Glu Leu Ser Arg Leu Arg Ser Asp Asp Thr Ala
            20                  25                  30

Val Tyr Tyr Cys Val Arg
        35

<210> SEQ ID NO 44
<211> LENGTH: 38
<212> TYPE: PRT
<213> ORGANISM: Artificial Sequence
<220> FEATURE:
<223> OTHER INFORMATION: Framework 3 in Heavy chain variable region of
      humanized anti-CD66c antibody (8F5-human-VH6)

<400> SEQUENCE: 44

Asn Gln Arg Phe Lys Val Lys Ala Thr Leu Thr Val Asp Val Ser Thr
1               5                   10                  15

Asn Thr Ala Tyr Met Glu Leu Ser Arg Leu Arg Ser Asp Asp Thr Ala
            20                  25                  30

Val Tyr Tyr Cys Val Arg
        35

<210> SEQ ID NO 45
<211> LENGTH: 38
<212> TYPE: PRT
<213> ORGANISM: Artificial Sequence
<220> FEATURE:
<223> OTHER INFORMATION: Framework 3 in Heavy chain variable region of
      humanized anti-CD66c antibody (8F5-human-VH7)

<400> SEQUENCE: 45

Asn Gln Arg Phe Lys Val Lys Ala Thr Leu Thr Val Asp Val Ser Thr
1               5                   10                  15

Asn Thr Ala Tyr Met Glu Leu Ser Arg Leu Arg Ser Asp Asp Thr Ala
            20                  25                  30

Val Tyr Tyr Cys Val Arg
        35

<210> SEQ ID NO 46
<211> LENGTH: 38
<212> TYPE: PRT
<213> ORGANISM: Artificial Sequence
<220> FEATURE:
<223> OTHER INFORMATION: Framework 3 in Heavy chain variable region of
      humanized anti-CD66c antibody (8F5-human-VH10)

<400> SEQUENCE: 46

Asn Gln Arg Phe Lys Val Lys Ala Thr Met Thr Val Asp Val Ser Thr
1               5                   10                  15

Asn Thr Ala Tyr Met Glu Leu Ser Arg Leu Arg Ser Asp Asp Thr Ala
            20                  25                  30

Val Tyr Tyr Cys Val Arg
        35
```

<210> SEQ ID NO 47
<211> LENGTH: 38
<212> TYPE: PRT
<213> ORGANISM: Artificial Sequence
<220> FEATURE:
<223> OTHER INFORMATION: Framework 3 in Heavy chain variable region of
      humanized anti-CD66c antibody (8F5-human-VH11)

<400> SEQUENCE: 47

Ala Gln Lys Phe Lys Gly Arg Val Thr Met Thr Arg Asp Thr Ser Thr
1               5                   10                  15

Asn Thr Ala Tyr Met Glu Leu Ser Arg Leu Arg Ser Asp Asp Thr Ala
            20                  25                  30

Val Tyr Tyr Cys Val Arg
        35

<210> SEQ ID NO 48
<211> LENGTH: 26
<212> TYPE: PRT
<213> ORGANISM: Artificial Sequence
<220> FEATURE:
<223> OTHER INFORMATION: Framework 3 in Light chain variable region of
      chimeric anti-CD66c antibody

<400> SEQUENCE: 48

Gly Met Ser Ser Arg Phe Ser Gly Ser Gly Ser Gly Arg Gln Tyr Ser
1               5                   10                  15

Leu Lys Ile Ser Ser Leu His Pro Asp Asp
            20                  25

<210> SEQ ID NO 49
<211> LENGTH: 26
<212> TYPE: PRT
<213> ORGANISM: Artificial Sequence
<220> FEATURE:
<223> OTHER INFORMATION: Framework 3 in Light chain variable region of
      humanized anti-CD66c antibody (8F5-human-VK5)

<400> SEQUENCE: 49

Gly Val Pro Ser Arg Phe Ser Gly Ser Gly Ser Gly Arg Gln Tyr Ser
1               5                   10                  15

Leu Lys Ile Ser Ser Leu His Pro Asp Asp
            20                  25

<210> SEQ ID NO 50
<211> LENGTH: 26
<212> TYPE: PRT
<213> ORGANISM: Artificial Sequence
<220> FEATURE:
<223> OTHER INFORMATION: Framework 3 in Light chain variable region of
      humanized anti-CD66c antibody (8F5-human-VK7)

<400> SEQUENCE: 50

Gly Val Pro Ser Arg Phe Ser Gly Ser Gly Ser Gly Thr Glu Tyr Thr
1               5                   10                  15

Leu Thr Ile Ser Ser Leu Gln Pro Asp Asp
            20                  25

<210> SEQ ID NO 51
<211> LENGTH: 26
<212> TYPE: PRT
<213> ORGANISM: Artificial Sequence
<220> FEATURE:
<223> OTHER INFORMATION: Framework 3 in Light chain variable region of humanized anti-CD66c antibody (8F5-human-VK8)

<400> SEQUENCE: 51

Gly Met Pro Ser Arg Phe Ser Gly Ser Gly Ser Gly Thr Glu Tyr Thr
1               5                   10                  15

Leu Thr Ile Ser Ser Leu Gln Pro Asp Asp
            20                  25

<210> SEQ ID NO 52
<211> LENGTH: 11
<212> TYPE: PRT
<213> ORGANISM: Artificial Sequence
<220> FEATURE:
<223> OTHER INFORMATION: Framework 4 in Light chain variable region of
      chimeric anti-CD66c antibody

<400> SEQUENCE: 52

Trp Gly Gln Gly Thr Ser Val Thr Val Ser Ser
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Framework 4 in Heavy chain variable region of
      humanzied anti-CD66c antibody (8F5-human-VH5)

<400> SEQUENCE: 53

Trp Gly Gln Gly Thr Leu Val Thr Val Ser Ser
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Framework 4 in Heavy chain variable region of
      humanzied anti-CD66c antibody (8F5-human-VH6)

<400> SEQUENCE: 54

Trp Gly Gln Gly Thr Leu Val Thr Val Ser Ser
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Framework 4 in Heavy chain variable region of
      humanzied anti-CD66c antibody (8F5-human-VH7)

<400> SEQUENCE: 55

Trp Gly Gln Gly Thr Leu Val Thr Val Ser Ser
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Framework 4 in Heavy chain variable region of
      humanzied anti-CD66c antibody (8F5-human-VH10)

<400> SEQUENCE: 56

Trp Gly Gln Gly Thr Leu Val Thr Val Ser Ser
1               5                   10

```
<210> SEQ ID NO 57
<211> LENGTH: 11
<212> TYPE: PRT
<213> ORGANISM: Artificial Sequence
<220> FEATURE:
<223> OTHER INFORMATION: Framework 4 in Heavy chain variable region of
      humanzied anti-CD66c antibody (8F5-human-VH11)

<400> SEQUENCE: 57

Trp Gly Gln Gly Thr Leu Val Thr Val Ser Ser
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Framework 4 in Light chain variable region of
      chimeric anti-CD66c antibody

<400> SEQUENCE: 58

Phe Gly Gly Gly Thr Lys Leu Glu Ile Ile
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Framework 4 in Light chain variable region of
      humanized anti-CD66c antibody (8F5-human-VK5)

<400> SEQUENCE: 59

Phe Gly Gly Gly Thr Lys Leu Glu Ile Lys
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Framework 4 in Light chain variable region of
      humanized anti-CD66c antibody (8F5-human-VK7)

<400> SEQUENCE: 60

Phe Gly Gly Gly Thr Lys Leu Glu Ile Lys
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Framework 4 in Light chain variable region of
      humanized anti-CD66c antibody (8F5-human-VK8)

<400> SEQUENCE: 61

Phe Gly Gly Gly Thr Lys Leu Glu Ile Lys
1               5                   10

<210> SEQ ID NO 62
<211> LENGTH: 363
<212> TYPE: DNA
<213> ORGANISM: Artificial Sequence
<220> FEATURE:
<223> OTHER INFORMATION: Polynucleotide encoding heavy chain variable
      region of chimeric anti-CD66c antibody
```

<400> SEQUENCE: 62

```
gaggtccagc tgcaacagtc tggacctgaa ctggtgaagc ctggagcttc aatgaagata      60
tcctgcaagg cttctggtta ctcattcact gactacacca tgaactgggt gaagcagagc     120 catgaaaga accttgagtg gattggactt attaatcctt ccatggtgg tactgtctcc       180 aaccagaggt tcaaggtcaa ggccacatta actgtagaca agtcatccaa cacagcctac     240
atggagctcc tcagtctgac atctgacgac tctgcggtct attactgtgt aagaggtgac     300
ccggtccgcc attactatgc tttggcctac tggggtcagg aacctcagt caccgtctcc      360 tca                                                                  363
```

<210> SEQ ID NO 63
<211> LENGTH: 217
<212> TYPE: DNA
<213> ORGANISM: Artificial Sequence
<220> FEATURE:
<223> OTHER INFORMATION: Polynucleotide encoding light chain variable
      region of chimeric anti-CD66c antibody

<400> SEQUENCE: 63

```
gacatccaga tgactcagtc tccagcttca ctgtctgcat ctgtgggaga aactgtcacc      60
atcacatgtg agcaagtga gaatgtttac ggtactttaa attggtatca gcggaaacag     120
ggaaaatctc ctcagctcct gatctatggt gcaaccaact ggcagatgg catgtcatcg     180 aggttcagtg gcagtggttc tggtagacag tattctc                             217
```

<210> SEQ ID NO 64
<211> LENGTH: 21
<212> TYPE: DNA
<213> ORGANISM: Artificial Sequence
<220> FEATURE:
<223> OTHER INFORMATION: 8F01 Primer of 1st frag forward

<400> SEQUENCE: 64

```
attactcgag gccaccatga a                                               21
```

<210> SEQ ID NO 65
<211> LENGTH: 23
<212> TYPE: DNA
<213> ORGANISM: Artificial Sequence
<220> FEATURE:
<223> OTHER INFORMATION: 8F02 Primer of 1st frag reverse

<400> SEQUENCE: 65

```
agttgaagcg ctgctcacag tca                                             23
```

<210> SEQ ID NO 66
<211> LENGTH: 23
<212> TYPE: DNA
<213> ORGANISM: Artificial Sequence
<220> FEATURE:
<223> OTHER INFORMATION: 8F03 Primer of 2nd frag forward

<400> SEQUENCE: 66

```
gtgagcagcg cttcaactaa ggg                                             23
```

<210> SEQ ID NO 67
<211> LENGTH: 26
<212> TYPE: DNA
<213> ORGANISM: Artificial Sequence
<220> FEATURE:
<223> OTHER INFORMATION: 3E04 Primer of 2nd frag reverse

```
<400> SEQUENCE: 67
agtcgaattc tcatttccca ggagag                                           26

<210> SEQ ID NO 68
<211> LENGTH: 23
<212> TYPE: DNA
<213> ORGANISM: Artificial Sequence
<220> FEATURE:
<223> OTHER INFORMATION: 8F04 Primer of 1st frag reverse

<400> SEQUENCE: 68
agttgaagca agacactg tca                                                23

<210> SEQ ID NO 69
<211> LENGTH: 23
<212> TYPE: DNA
<213> ORGANISM: Artificial Sequence
<220> FEATURE:
<223> OTHER INFORMATION: 8F05 Primer of 1st frag forward

<400> SEQUENCE: 69
gtgtcttctg cttcaactaa ggg                                              23

<210> SEQ ID NO 70
<211> LENGTH: 26
<212> TYPE: DNA
<213> ORGANISM: Artificial Sequence
<220> FEATURE:
<223> OTHER INFORMATION: 3E01 Primer of 1st frag forward

<400> SEQUENCE: 70
attactcgag gccaccatga agtggg                                           26

<210> SEQ ID NO 71
<211> LENGTH: 23
<212> TYPE: DNA
<213> ORGANISM: Artificial Sequence
<220> FEATURE:
<223> OTHER INFORMATION: 8F06 Primer of 1st frag reverse

<400> SEQUENCE: 71
aacagtccgc ttgatctcca gct                                              23

<210> SEQ ID NO 72
<211> LENGTH: 23
<212> TYPE: DNA
<213> ORGANISM: Artificial Sequence
<220> FEATURE:
<223> OTHER INFORMATION: 3EL02(2) Primer of 2nd frag forward

<400> SEQUENCE: 72
gagatcaagc ggactgttgc tgc                                              23

<210> SEQ ID NO 73
<211> LENGTH: 26
<212> TYPE: DNA
<213> ORGANISM: Artificial Sequence
<220> FEATURE:
<223> OTHER INFORMATION: 3E08 Primer of 2nd frag reverse

<400> SEQUENCE: 73
attagaattc tcagcactcg ccgcgg                                           26
```

ANTIBODY BINDING SPECIFICALLY TO CD66C AND USE THEREOF

TECHNICAL FIELD

The present invention relates to an anti-CD66c antibody and its use for treating cancer, and more particularly, it is possible to induce T-cell activation or humoral immune response using an antibody specifically recognizing CD66c. An antibody specifically recognizing CD66c or antigen-binding fragment thereof, a nucleic acid molecule encoding the antibody or antigen-binding fragment thereof, a vector comprising the nucleic acid molecule and a host cell are used for alleviation, prevention, treatment or diagnosis of CD66c-related disease, for example solid cancer.

RELATED ART

It is known that a 5-year survival rate of lung cancer exceeds 80% if the lung cancer was found early in IA stage (Mulshine, J. L. and Sullivan, D. C. Clinical practice. Lung cancer screening. *N. Engl. J. Med.* 2005; 352:2714-2720). It is therefore important to find good markers that enables early discovery of lung cancer in pursuit of specific biological markers. Especially, lung cancer is a representative heterogeneous tumor, and the response and the prognosis are different for a variety of treatments. Lung cancer can be divided into two major categories medically, small cell lung cancer and non-small cell lung cancers (NSCLC). Non-small cell lung cancers can be further divided into lung adenocarcinoma, squamous cell carcinoma and large cell carcinoma.

Meanwhile, CD66c is known as CEACAM6 (Carcinoembryonic antigen-related cell adhesion molecule 6) or NCA (non-specific cross-reacting glycoprotein antigen)-90 and has a higher concentration in the blood of lung cancer, pancreatic cancer, breast cancer, rectal cancer and hepatoma patients. The above CD66c is an important protein for cell adhesion and is involved in adhesion of endothelial cells activated by cytokine in case of neutrophils.

Also, normal cells destroy themselves if cell adhesion is prevented. This process is called anoikis. Tumor cells, however, are resistant to such anoikis and promote cancer outbreak and metastasis of cancer as a result. There is a report that the above CD66c prevents anoikis, and there also is a report that malignant phenotype changes in cancer cells by regulating the expression of CD66c. Also, when the protein expression is inhibited by silencing CD66c genes by using small interfering RNA, metastasis is inhibited by enhancement of anoikis in vivo. In conclusion, metastasis can be prevented by inhibiting the function of CD66c.

DISCLOSURE

Technical Problem

In accordance with an embodiment, the present invention provides an antibody binding to CD66c, and an antigen-binding fragment thereof.

Another embodiment of the present invention provides a nucleic acid molecule encoding the antibody or the antigen-binding fragment, a vector carrying the nucleic acid molecule, and a host cell including the nucleic acid molecule.

A further embodiment of the present invention provides a method or a kit for detecting or diagnosing a CD66c associated disease, comprising the antibody, the nucleic acid molecule, the vector, and/or the host cell.

Still a further embodiment of the present invention provides a composition for preventing, treating or alleviating CD66c associated disease, comprising the antibody, the nucleic acid molecule, the vector, and/or the host cell, or use of the antibody, the nucleic acid molecule, the vector, and/or the host cell in preventing, treating, or alleviating a carbonic anhydrase-associated disease.

Still another embodiment of the present invention provides a method for preventing, treating or alleviating a CD66c associated disease, comprising administering a composition comprising the antibody, the nucleic acid molecule, the vector, and/or the host cell to a subject with a carbonic anhydrase-associated disease.

Yet a further embodiment of the present invention provides a composition or a method for prevention or treatment of cancer or disease associated with cancer metastasis.

Technical Solution

The present invention relates to an antibody recognizing and binding to CD66c, a nucleic acid molecule coding for the antibody or an antigen-binding fragment, a vector carrying the nucleic acid molecule, a host cell including the nucleic acid molecule or the vector, and use of the antibody or an antigen-binding fragment thereof in the alleviation, prevention, treatment or diagnosis of CD66c-positive solid tumors.

Cluster of Differentiation 66c (CD66c) is a protein known as carcinoembryonic antigen-related cell adhesion molecule 6 (CEACAM 6) or non-specific cross-reacting glycoprotein antigen (NCA)-90 and as an important protein for cell adhesion. CD66c can be represented preferably, but not limited to, amino acid sequence of SEQ ID No: 1 (Genbank Protein No. AAH05008).

An embodiment provides an anti-CD66c antibody that specifically recognizes CD66c. The anti-CD66c antibodies according to the invention induce humoral and cell-mediated immune responses. The anti-CD66c antibody according to the present invention specifically recognizes the epitope of CD66c (Cluster of Differentiation 66c) and can effectively detect the CD66c antigen.

As used herein, the term, "antibody" means a substance produced by stimulation of an antigen in the immune system, and the kind thereof is not particularly limited. The antibody may be generated in a non-natural manner, for example, recombinantly or synthetically generated. The antibody may be an animal antibody (e. g., mouse antibody, etc.), a chimeric antibody, a humanized antibody or a human antibody. The antibody may be a monoclonal antibody or a polyclonal antibody.

In addition, herein, an antibody can be understood to include an antigen-binding fragment of an antibody having antigen-binding ability, unless otherwise specified. In the present specification, the term, "complementarity determining regions (CDR)" refers to a region of antibody that imparts the binding specificity of antibody to an antigen among variable regions of the antibody. The antigen-binding fragment of the antibody described above may be an antibody fragment comprising at least one of the complementarity determining regions.

An embodiment of the present invention provides an anti-CD66c antibody or antigen-binding fragment thereof that specifically recognizes or specifically binds to CD66c.

The anti-CD66c antibody according to the present invention specifically recognizes and/or binds to CD66c, and the antibody includes a mouse antibody, chimeric antibody or humanized antibody. The chimeric antibody in the present invention is an antibody that the sequence of the variable region is derived from one species and the sequence of the constant region is derived from other species, for example, that the variable region is derived from mouse and the constant region is derived from human. The humanized antibody in the present invention is an antibody which has a low immunogenicity in human and an activity of non-human antibody. For example, it can be prepared by keeping non-human CDR region and substituting the rest of the region with human counterparts. For example, the literature is referenced: Morrison et al, Proc. Natl. Acad. ScL USA, 81:6851-6855(1984); Morrison and Oi, Adv. Immunol., 44:65-92 (1988); Verhoeyen et al, Science, 239:1534-1536 (1988); Padlan, Molec. Immun, 28:489-498 (1991); Padlan, Molec. Immun, 31(3):169-217 (1994).

The antibody fragment in the present invention is not limited, as long as it recognizes specifically CD66c epitope and includes variable region of a light chain ($V_L$) and variable region of a heavy chain ($V_H$). It can be selected from a group consisting of Fab, Fab', F(ab')2, scFv, dsFv and CDR. Especially, scFv is an antibody fragment prepared as a single chain by connecting the variable region of a heavy chain ($V_H$) and variable region of a light chain ($V_L$) with a linker polypeptide.

An example of a mouse antibody or a chimeric antibody according to the present invention can be an antibody or antigen-binding fragment thereof including at least one selected from the group consisting of an amino acid sequence of VH CDR comprising the amino acid sequences of SEQ ID NOS: 1 to 3 and an amino acid sequence of VL CDR comprising amino acid sequences of SEQ ID NOs: 4 to 6. The CDRs and the variable regions of an example of the mouse antibody or chimeric antibody are summarized in Table 1 below.

Specifically, an example of the antibody of the present invention may include SEQ ID NO: 1 (CDR1), SEQ ID NO: 2 (CDR2) and SEQ ID NO: 3 (CDR3) as VH CDR and/or SEQ ID NO: 4 (CDR1), SEQ ID NO: 5 (CDR2), and SEQ ID NO: 6 (CDR3) as VL CDR.

The mouse antibody or chimeric antibody may comprise a VH region including the amino acid sequence of SEQ ID NO: 7 and a VL region including the amino acid sequence of SEQ ID NO: 8.

The present invention relates to a pharmaceutical composition, a kit or a method of prevention or treatment of a disease selected from cancer and cancer metastasis, comprising a mouse antibody or chimeric antibody as an active ingredient. The present invention also relates to a pharmaceutical composition for prevention or treatment of a disease selected from cancer and cancer metastasis, comprising a mouse antibody or chimeric antibody as an active ingredient, for example an anti-CD66c antibody or antigen-binding fragment thereof including CDR-H1, CDR-H2, CDR-H3, CDR-L1, CDR-L2, and CDR-L3 of the antibody produced by a hybridoma cell deposited as an accession number of KCLRF-BP-00230. The hybridoma cell was deposited with the Korean Cell Line Research Foundation (KCLRF) as '8F5' on Feb. 22, 2010 and received an accession number of KCLRF-BP-00230, which has been described in detail in KR 10-1214177.

The cancer may be CD66c-positive solid cancer, for example, CD66c-positive lung cancer, colon cancer, stomach cancer, liver cancer, breast cancer, or prostate cancer, preferably colon cancer, stomach cancer or liver cancer. The use of prevention, inhibition, or treatment for cancer and caner metastasis may, for example, reduce solid cancer or the cell size of solid cancer, or induce or promote tumor regression.

The present invention can prepare a humanized antibody by using the amino acid sequence of anti-CD66c antibody 8F5 in the mouse antibody or chimeric antibody and the framework sequences of human. From the candidates of recombinant humanized antibodies are selected on the basis of expression degree, aggregation, and degree of cell binding, where the expression occurs normally, the protein aggregation is very little due to the instability of the protein itself is small, and of similar binding ability to the target antigen-positive cell. Specifically, the cell binding profile is similar to that of the chimeric antibody and is obtained by multiplying positive rate of antibody positivity (% gated) with the average fluorescence (mean), then is compared with the chimeric antibody to select the candidate antibodies within the range of ±20% (Example 2). Therefore, when CDR region sequences of the mouse antibody are inserted into the framework region of human antibody at the time of preparing the humanized antibody, the binding ability of prepared antibody is rapidly decreased due to the change of the original protein structure. In consideration of the decrease of the binding ability of prepared antibody, the selected humanized antibodies of the present invention are very excellent antibody.

Preferably, five types of recombinant humanized antibodies exhibiting a high binding affinity based on the cell binding ability as compared to the chimeric antibody are selected and subjected to binding assay for CD66c antigen and similar antigen to CD66 antigen by ELISA.

In addition, the humanized antibody according to the present invention exhibits excellent stability compared to the chimeric antibody, for example, an antibody having stability which is reflected as ANS reactivity variation of less than 200%. The ANS reactivity variation of less than 200% is regarded as a very small variation and the higher variation value than 200% can be interpreted as observing ANS reactivity due to the significant structural change of protein. Accordingly, the humanized antibody according to the present invention has similar antigen binding activity and cell binding ability to the chimeric antibody, and the increased physical stability of the antibody protein itself, which can be very excellent in terms of a therapeutic agent of the therapeutic antibody.

The fluorescence variation of the antibody against the ANS reagent can be measured by dividing the difference between the fluorescence value measured at low temperature conditions (e.g, 4° C.) and the fluorescence value measured at high temperature conditions (e.g, 62° C.) with the fluorescence value measured at low temperature conditions.

Fluorescence variation=(fluorescence value measured at high temperature condition−fluorescence value measured at low temperature condition)/ (fluorescence value measured at low temperature condition)　　[Mathematic Equation]

As a method for obtaining a specific fluorescence variation of antibody, the The reactivity of ANS reagent was measured by a fluorescent reader after being left for 4 hours at a refrigeration condition (4° C.) and a temperature of 62° C., and expressed as a fluorescence value, and the fluorescence variation can be obtained using the equation.

Examples of the humanized antibody according to the present invention may include one or more amino acid sequences selected from the group consisting of amino acid sequences that determine the CDRs of the heavy chain variable region or light chain variable region comprising the amino acid sequences of SEQ ID NOs: 9 to 13. The examples of mouse antibody and the chimeric antibody ma include one or more amino acid sequences selected from the group consisting of amino acid sequences that determine the CDRs of the heavy chain variable region comprising the amino acid sequences of SEQ ID NOs: 1 to 3 or light chain variable region comprising the amino acid sequences of SEQ ID NOs: 4 to 6.

Specifically, an example of a humanized antibody includes an amino acid sequence determining the CDR1 of the VH region comprising the amino acid sequence of SEQ ID NO: 1 or 9, an amino acid sequence determining the CDR2 of the VH region comprising the amino acid sequence of SEQ ID NO: 2 or 10, and the CDR3 of the VH region comprising the amino acid sequence of SEQ ID NO: 3.

Examples of the humanized antibody include an amino acid sequence determining the CDR1 of the VL region including the amino acid sequence of SEQ ID NO: 4, 11 or 12, an amino acid sequence determining the CDR2 of the VL region including the amino acid sequence of SEQ ID NO: 5, and an amino acid sequence determining the CDR3 of the VL region comprising the amino acid sequence of SEQ ID NO: 6 or 13.

Examples of the humanized antibody include a heavy chain variable region selected from the group consisting of the amino acid sequence of SEQ ID NO: 7 and SEQ ID NOs: 14 to 18 and a light chain variable region selected from the group consisting of the amino acid sequence of SEQ ID NO: 8 and SEQ ID Nos: 19-21, but does not include the antibody comprising SEQ ID NO: 7 and SEQ ID NO: 8.

The CDR sequences and variable region sequences according to an example of the humanized antibody are summarized in Table 1 below.

TABLE 1

| Name | SEQUENCE | SEQ ID NO |
|---|---|---|
| 8F5-chimeric $V_H$-CDR1 | ASGYSFTDYTMN | 1 |
| 8F5-chimeric $V_H$-CDR2 | LINPFHGGTVSNQRFKV | 2 |
| 8F5-chimeric $V_H$-CDR3 | VRGDPVRHYYALAY | 3 |
| 8F5-chimeric $V_L$-CDR1 | GASENVYGTLN | 4 |
| 8F5-chimeric $V_L$-CDR2 | GATNLAD | 5 |
| 8F5-chimeric $V_L$-CDR3 | VATYYCQNVLSAPYT | 6 |
| 8F5-chimeric $V_H$ | EVQLQQSGPELVKPGASMKISCKASGYSFTDYTMNWVKQSH GKNLEWIGLINPFHGGTVSNQRFKVKATLTVDVSSNTAYME LLSLTSDDSAVYYCVRGDPVRHYYALAYWGQGTSVTVSS | 7 |
| 8F5-chimeric $V_L$ | DIQMTQSPASLSASVGETVTITCGASENVYGTLNWYQRKQG KSPQLLIYGATNLADGMSSRFSGSGSGRQYSLKISSLHPDD VATYYCQNVLSAPYTFGGGTKLEII | 8 |
| 8F5-human $V_H$-CDR1 | ASGYSFTDYTMN | 1 |
| 8F5-human $V_H$-CDR1 | ASGYSFTDYTMH | 9 |
| 8F5-human $V_H$-CDR2 | INPFHGGTVSNQRFKV | 2 |
| 8F5-human $V_H$-CDR2 | LINPFGGSTSYAQKFKG | 10 |
| 8F5-human $V_H$-CDR3 | VRGDPVRHYYALAY | 3 |
| 8F5-human $V_L$-CDR1 | GASENVYGTLN | 4 |
| 8F5-human $V_L$-CDR1 | GASENVYGTLA | 11 |
| 8F5-human $V_L$-CDR1 | RASENVYGTLN | 12 |
| 8F5-human $V_L$-CDR2 | GATNLAD | 5 |
| 8F5-human $V_L$-CDR3 | VATYYCQNVLSAPYT | 6 |
| 8F5-human $V_L$-CDR3 | FATYYCQNVLSAPYT | 13 |
| 8F5-human-VH5 | QVQLVQSGAEVKKPGASVKISCKASGYSFTDYTMNWVRQAH GQNLEWIGLINPFHGGTVSNQRFKVKATLTVDVSTNTAYME LSRLRSDDTAVYYCVRGDPVRHYYALAYWGQGTLVTVSS | 14 |
| 8F5-human-VH6 | QVQLVQSGAEVKKPGASMKISCKASGYSFTDYTMNWVKQAP GQNLEWIGLINPFHGGTVSNQRFKVKATLTVDVSTNTAYME LSRLRSDDTAVYYCVRGDPVRHYYALAYWGQGTLVTVSS | 15 |
| 8F5-human-VH7 | QVQLVQSGAEVKKPGASMKISCKASGYSFTDYTMNWVRQAP GQGLEWIGLINPFHGGTVSNQRFKVKATLTVDVSTNTAYME LSRLRSDDTAVYYCVRGDPVRHYYALAYWGQGTLVTVSS | 16 |

TABLE 1-continued

| Name | SEQUENCE | SEQ ID NO |
|---|---|---|
| 8F5-human-VH10 | QVQLVQSGAEVKKPGASVKVSCKASGYSFTDYTMNWVKQAP<br>GQNLEWIGLINPFHGGTVSNQRFKVKATMTVDVSTNTAYME<br>LSRLRSDDTAVYYCVRGDPVRHYYALAYWGQGTLVTVSS | 17 |
| 8F5-human-VH11 | QVQLVQSGAEVKKPGASVKISCKASGYSFTDYTMHWVKQAP<br>GQNLEWIGUNPFGGSTSYAQKFKGRVTMTRDTSTNTAYMEL<br>SRLRSDDTAVYYCVRGDPVRHYYALAYWGQGTLVTVSS | 18 |
| 8F5-human-VK5 | DIQMTQSPSTLSASVGDRVTITCGASENVYGTLAWYQRKPG<br>KAPKLLIYGATNLADGVPSRFSGSGSGREYTLTISSLQPDD<br>FATYYCQNVLSAPYTFGGGTKLEIK | 19 |
| 8F5-human-VK7 | DIQMTQSPSTLSASVGDRVTITCGASENVYGTLNWYQRKPG<br>KAPKLLIYGATNLADGVPSRFSGSGSGTEYTLTISSLQPDD<br>FATYYCQNVLSAPYTFGGGTKLEIK | 20 |
| 8F5-human-VK8 | DIQMTQSPSTLSASVGDRVTITCRASENVYGTLNWYQRKPG<br>KAPKLLIYGATNLADGMPSRFSGSGSGTEYTLTISSLQPDD<br>FATYYCQNVLSAPYTFGGGTKLEIK | 21 |

The framework sequences of one example of a humanized antibody according to the present invention are shown in Tables 3 and 4 below, wherein said antibody may include at least one selected from the group consisting of frameworks 1 to 4 of the heavy chain variable region and frameworks 1 to 4 of the light chain variable region And may be an antibody comprising one or more frameworks.

Specifically, the amino acid sequence of framework 1 of in the heavy chain variable region may comprise SEQ ID NOS: 23 to 27, the amino acid sequence of framework 2 may comprise SEQ ID NOS: 32 to 37, and the amino acid sequence of framework 3 43 to 47, and the amino acid sequence of Framework 4 may include SEQ ID NOS: 53 to 57.

In the light chain variable region, the amino acid sequence of Framework 1 may comprise SEQ ID Nos: 29 to 31, the amino acid sequence of Framework 2 may comprise SEQ ID NOs: 39 to 41, and the amino acid sequence of Framework 3 may correspond to the amino acid sequence of SEQ ID NOs: 49-51, and the amino acid sequence of Framework 4 may comprise SEQ ID NOs: 59 to 61. The framework sequences according to examples of the humanized antibody are shown in the following table.

TABLE 2

| Name | FR1 | SEQ ID NO | FR2 | SEQ ID NO |
|---|---|---|---|---|
| V<sub>H</sub>-Chimeric | EVQLQQSGPELVKPGASMKISCK | 22 | WVKQSHGKNLEWIG | 32 |
| VH5 | QVQLVQSGAEVKKPGASVKISCK | 23 | WVRQAHGQNLEWIG | 33 |
| VH6 | QVQLVQSGAEVKKPGASMKISCK | 24 | WVKQAPGQNLEWIG | 34 |
| VH7 | QVQLVQSGAEVKKPGASMKISCK | 25 | WVRQAPGQGLEWIG | 35 |
| VH10 | QVQLVQSGAEVKKPGASVKVSCK | 26 | WVKQAPGQNLEWIG | 36 |
| VH11 | QVQLVQSGAEVKKPGASVKISCK | 27 | WVKQAPGQNLEWIG | 37 |
| V<sub>L</sub>-Chimeric | DIQMTQSPASLSASVGETVTITC | 28 | WYQRKQGKSPQLLIY | 38 |
| VK5 | DIQMTQSPSTLSASVGDRVTITC | 29 | WYQRKPGKAPKLLIY | 39 |
| VK7 | DIQMTQSPSTLSASVGDRVTITC | 30 | WYQRKPGKAPKLLIY | 40 |
| VK8 | DIQMTQSPSTLSASVGDRVTITC | 31 | WYQRKPGKAPKLLIY | 41 |

TABLE 3

| name | FR3 | SEQ ID NO | FR4 | SEQ ID NO |
|---|---|---|---|---|
| V<sub>H</sub>-Chimeric | NQRFKVKATLTVDVSSNTAYME<br>LLSLTSDDSAVYYCVR | 42 | WGQGTSVTVSS | 52 |
| VH5 | NQRFKVKATLTVDVSTNTAYME<br>LSRLRSDDTAVYYCVR | 43 | WGQGTLVTVSS | 53 |
| VH6 | NQRFKVKATLTVDVSTNTAYME<br>LSRLRSDDTAVYYCVR | 44 | WGQGTLVTVSS | 54 |

TABLE 3-continued

| name | FR3 | SEQ ID NO | FR4 | SEQ ID NO |
|---|---|---|---|---|
| VH7 | NQRFKVKATLTVDVSTNTAYME LSRLRSDDTAVYYCVR | 45 | WGQGTLVTVSS | 55 |
| VH10 | NQRFKVKATMTVDVSTNTAYME LSRLRSDDTAVYYCVR | 46 | WGQGTLVTVSS | 56 |
| VH11 | AQKFGGRVTMTRDTSTNTAYME LSRLRSDDTAVYYCVR | 47 | WGQGTLVTVSS | 57 |
| V$_L$-Chimeric | GMSSRFSGSGSGRQYSLKISSL HPDD | 48 | FGGGTKLEII | 58 |
| VK5 | GVPSRFSGSGSGRQYSLKISSL HPDD | 49 | FGGGTKLEIK | 59 |
| VK7 | GVPSRFSGSGSGTEYTLTISSL QPDD | 50 | FGGGTKLEIK | 60 |
| VK8 | GMPSRFSGSGSGTEYTLTISSL QPDD | 51 | FGGGTKLEIK | 61 |

The humanized antibody may comprise a VH region selected from the group consisting of the amino acid sequences of SEQ ID NOs: 14 to 18 and a VL region selected from the group consisting of the amino acid sequences of SEQ ID NOs: 19 to 21. Specifically, the examples of the humanized antibody include an antibody (Vk8+VH6) comprising a VH region including the amino acid sequence of SEQ ID NO: 15 and a VL region comprising the amino acid sequence of SEQ ID NO: 21, an antibody (Vk8+VH11) comprising a VH region including an amino acid sequence of SEQ ID NO: 18 and a VL region comprising the amino acid sequence of SEQ ID NO: 21, an antibody (Vk5+VH7) comprising a VH region including the amino acid sequence of SEQ ID NO: 16, and a VL region comprising the amino acid sequence of SEQ ID NO: 19, an antibody (Vk7+VH6) comprising a VH region including the amino acid sequence of SEQ ID NO: 17 and a VL region comprising the amino acid sequence of SEQ ID NO: 20, an antibody (Vk7+VH10) comprising a VH region including the amino acid sequence of SEQ ID NO: 15, and a VL region comprising the amino acid sequence of SEQ ID NO: 20, an antibody (Vk7+VH7) comprising a VH region comprising the amino acid sequence of SEQ ID NO: 16 and a VL region comprising the amino acid sequence of SEQ ID NO: 20, an antibody (Vk7+VH5) comprising a VH region comprising the amino acid sequence of SEQ ID NO: 14 and a VL region comprising the amino acid sequence of SEQ ID NO: 20, and an antibody (Vk8+VH7) comprising a VH region comprising the amino acid sequence of SEQ ID NO: 16 and a VL region comprising the amino acid sequence of SEQ ID NO: 21. Specific combinations and amino acid sequences of the antibodies are shown in Table 6 below. The preferred examples of antibody include an antibody (Vk8+VH6) comprising a VH region including the amino acid sequence of SEQ ID NO: 15 and a VL region comprising the amino acid sequence of SEQ ID NO: 21, an antibody (Vk8+VH11) comprising a VH region including an amino acid sequence of SEQ ID NO: 18 and a VL region comprising the amino acid sequence of SEQ ID NO: 21, an antibody (Vk5+VH7) comprising a VH region including the amino acid sequence of SEQ ID NO: 16, and a VL region comprising the amino acid sequence of SEQ ID NO: 19, an antibody (Vk7+VH6) comprising a VH region including the amino acid sequence of SEQ ID NO: 17 and a VL region comprising the amino acid sequence of SEQ ID NO: 20, and an antibody (Vk7+VH10) comprising a VH region including the amino acid sequence of SEQ ID NO: 15, and a VL region comprising the amino acid sequence of SEQ ID NO: 20.

Unlike the mouse antibody or chimeric antibody, the humanized antibody showed 10 times higher stability than the chimeric 8F5 antibody as well as difference in reduced immunogenicity, when being administered to human body. Specifically, the antibody has high stability, which is supported by less than 200% of fluorescence variation caused by ANS binding at a high temperature, for example, at a temperature of 62° C.

In a specific strict condition, the chimeric 8F5 antibody showed a variation in ANS reactivity by 1,406%, while the humanized antibody showed a relatively small variation of about 114% and 133%, indicating that the humanized antibody was stabilized on the protein.

The chimeric 8F5 antibody and the humanized antibodies increase the activation of T cells by T cell activation factors and increase the activity of T cell, even under T cell activation conditions caused by mixing same kinds of dendritic cells and T cells derived from different human. Such induction of T cell activation induces the death of cancer cells, when T cell is co-cultured with cancer cells, and induces T cell activation under co-culturing conditions with various cancer cells.

The antibody or the antigen-binding fragment thereof in accordance with an embodiment of the present invention exhibits tumor regression activity and a direct inhibitory effect on tumor cell lines. As used herein, the term, "tumor regression" is intended to encompass the induction or the promotion of a decrease in tumor size, and/or inhibition, interruption, or reduction in tumor cell growth. The decrease of tumor size means that, when the antibody or a fragment thereof according to the present invention is administered, a tumor size decreases to, for example, 97% or less, 95% or less, 90% or less, 85% or less, 80% or less, or 75% or less of the tumor size before administration.

The antibody according to the present invention exhibits both antibody-dependent cell-mediated cytotoxicity (ADCC) and complement-dependent cytotoxicity (CDC).

The term "CDR (Complementarity Determining Region)" refers to an amino acid sequence of the hypervariable region of a heavy chain and a light chain of an immunoglobulin. The heavy chain and the light chain may each include three CDRs (CDRH1, CDRH2, CDRH3, and CDRL1, CDRL2, CDRL3). The CDRs of an antibody can provide an essential contact residue for binding to an antigen or an epitope.

Throughout the specification, the terms "specifically binding" or "specifically recognizing" has the same meaning, as it is generally known to a person of ordinary skill in the art, indicating that an antigen and an antibody specifically interact with each other and cause an immunological response.

The term "antigen-binding fragment," means a fragment of the full structure of an immunoglobulin, which is a partial polypeptide including a domain to which an antigen can bind. For example, it may be scFv, (scFv)$_2$, scFv-Fc, Fab, Fab', or F(ab')$_2$ but is not limited thereto.

The anti-CD66c antibody or fragment thereof may be coupled to various labeling agents, toxins, or anti-tumor drugs. It will be apparent to those skilled in the art that the antibody of the invention can be coupled to a labeling agent, a toxin, or an anti-tumor drug by a method well known in the art. Such coupling may be chemically conducted on the site of attachment after expression of the antibody or antigen. Alternatively, the coupling product may be engineered into the antibody or antigen of the invention at the DNA level. Subsequently, the DNA is then expressed in a suitable host system as described herein below, and the expressed proteins are collected and, if necessary, renatured. Coupling may be achieved via a linker, known in the art. In particular, different linkers that release a toxin or an anti-tumor drug under acidic or alkaline conditions or upon exposure to specific proteases may be employed with this technology. In some embodiments, it may be desirable for the labeling agent, toxin, or anti-tumor drug to be attached to spacer arms in various lengths to reduce potential steric hindrance.

The labeling agent may be selected from the group consisting of a radioisotope, a hapten, a fluorescent, a chromogen, and a dye. Particularly, the labeling agent may be selected from among FLAG, GFP, YFP, RFP, dTomato, cherry, Cy3, Cy5, Cy5.5., Cy7, DNP, AMCA, biotin, digoxigenin, Tamra, Texas Red, rhodamine, Alexa fluors, FITC and TRITC. Alternatively, the labeling agent may be a radioisotope such as, for example, 3H, 14C, 15N, 35S, 90Y, 99Tc, 111In, 125I, or 131I. Further examples of a suitable labeling agent include enzymatic groups (e.g. horseradish peroxidase, horseradish galactosidase, luciferase, alkaline phosphatase), chemiluminescent groups, biotinyl groups, or predetermined polypeptide epitopes recognized by a secondary reporter.

So long as it is toxic to cells or organisms, any toxin may be used in the present invention. For examples, a radioisotope, a small molecule, a peptide, or a protein may be used as a toxin. The antibody or fragment thereof may be coupled with a toxin to form a fusion protein. As a toxin protein, ricin, saporin, gelonin, momordin, diphtheria toxin, or *pseudomonas* toxin may be used. As for the radioisotope, its examples include 131I, 188Rh, and 90Y, but are not limited thereto.

As used herein, the term "anti-tumor agent" specifies a drug capable of either stopping or slowing down the abnormal growth of tissues. Thus, anti-tumor agents are particularly useful in treating cancer. An anti-tumor agent may be an angiogenesis inhibitor, a DNA intercalator or a DNA cross-linker, a DNA synthesis inhibitor, a DNA-RNA transcription regulator, an enzyme inhibitor, a gene regulator, a microtubule inhibitor, or other antitumor agents.

The present invention further relates to a nucleic acid molecule encoding the antibody of the present invention. The nucleic acid molecule of the present invention, encoding the antibody of the present invention, may be, for example, DNA, cDNA, RNA, a synthetically produced DNA or RNA, or a recombinantly-produced chimeric nucleic acid molecule comprising any of those nucleic acid molecules, either alone or in combination. The nucleic acid molecule may also be genomic DNA corresponding to an entire gene or a substantial portion thereof, or to a fragment or derivative thereof. The nucleotide sequence of the nucleic acid molecule may be a modified nucleotide sequence in which substitution, deletion or addition occurs on one or more nucleotide residues, and causes substitution or mutation of at least one amino acid residue of the amino acid sequence of the antibody. In a particular embodiment of the present invention, the nucleic acid molecule is a cDNA molecule.

One embodiment of the present invention also relates to a vector comprising the nucleic acid molecule in an expressible form. The vector of the present invention may be, for example, a phage, a plasmid, a viral vector, or a retroviral vector. Retroviral vectors may be replication-competent or replication-defective. In the latter case, viral propagation will generally occur in complementing host/cells.

The aforementioned nucleic acid molecule may be inserted into a vector such that translational fusion with another polynucleotide occurs. Generally, a vector may contain one or more origins of replication (ori) and inheritance systems for cloning or expression, one or more markers for selection in the host, e. g., antibiotic resistance, and one or more expression cassettes. Examples of a suitable origin of replication (ori) include the Col E1, the SV40 viral and the M 13 origins of replication.

In the present invention, the nucleic acid molecule may be designed for introduction into a host, either directly or via a liposome, a phage vector, or a viral vector (e.g. adenoviral vector, retroviral vector, etc.). Additionally, baculoviral systems, or systems based on vaccinia virus or semliki forest virus can be used as eukaryotic expression systems for the nucleic acid molecules of the present invention.

Another embodiment of the present invention pertains to a non-human host including the vector of the present invention. The host may be prokaryotic or eukaryotic. The polynucleotide or vector of the present invention, present in a host cell, may either be integrated into the genome of the host cell or may be maintained extra-chromosomally.

In addition, the present invention is concerned with a transgenic, non-human animal, available for the production of the antibody of the present invention, comprising one or more nucleic acid molecules of the present invention. Antibodies can be produced in and recovered from tissue or body fluids, such as milk, blood or urine, from goats, cows, horses, pigs, rats, mice, rabbits, hamsters or other mammals.

Moreover, the present invention provides a method for producing a substance selectively recognizing an antigen-determining region of CD66c, and a cell line producing an antibody selectively recognizing an antigen-determining region of CD66c. An antibody to an antigen-determining region of CD66c or a fragment thereof, may be produced using a typical method with a CD66c protein, an antigen-determining region of CD66c, a portion of CD66c containing an antigen-determining region of CD66c, or a cell expressing an antigen-determining region of CD66c serving as an antigen. For example, a method for producing an anti-CD66c antibody can be achieved through a method for producing a cell line producing an anti-CD66c antibody, comprising (a) injecting and immunizing an animal with a CD66c protein, an antigen-determining region of CD66c, a portion of CD66c containing an antigen-determining region of CD66c, or a cell expressing an antigen-determining region of CD66c, (b) obtaining splenocytes producing an antibody specific for CD66c, and (c) fusing the splenocytes with myeloma cells to give hybridoma cells and selecting a hybridoma cell producing an antibody to CD66c. The antibody can be isolated by culturing the cell line in vitro or by introducing the cell line in vivo. For example, the cell line may be intraperitoneally injected into mice, followed by isolating and purifying the antibody from the ascites. Isolation and purification of monoclonal antibodies may be achieved by subjecting the culture supernatant and ascites to ion exchange chromatography (DEAE or DE52) or affinity chromatography using an anti-immunoglobulin column or protein A column.

The antigen-determining region to which the antibody of the present invention binds exhibits solid tumor-specific expression. Hence, the anti-CD66c antibody can not only be effectively used to detect tumor cells, but can also exert cytotoxicity only on tumor cells when it carries a toxic substance.

A further embodiment of the present invention provides the use of CD66c, particularly an antigen-determining region located at a non-catalytic domain of CD66c, in detecting solid tumors. Also, a composition for detecting cancer stem cells of solid tumors, comprising a substance interacting with the antigen-determining region is provided. The interacting substance may be any substance that is able to interact with CD66c, particularly an antigen-determining region of CD66c located at a non-catalytic domain thereof. In particular, the interacting substance may be selected from the group consisting of a small molecular chemical, an antibody, an antigen-binding fragment of an antibody, an aptamer, or a combination thereof.

In another embodiment, the present invention relates to a diagnostic composition, comprising the antibody of the present invention, the nucleic acid molecule of the present invention, the vector of the present invention, or the host of the present invention. The term "diagnostic composition", as used herein, refers to a composition comprising at least one of the antibody, the nucleic acid molecule, the vector, and/or the host of the present invention.

The diagnostic composition of the present invention is useful in the detection of undesired expression or overexpression of CD66c in various cells, tissues or another suitable sample, by contacting a sample with an antibody of the present invention and determining the presence of a CD66c in the sample. Accordingly, the diagnostic composition of the invention may be available for assessing the onset or status of disease, as defined herein below. In particular, malignant cells, such as cancer cells being capable of expressing CD66c can be targeted with the antibody of the present invention, or a fragment or derivative thereof. The cells which have bound the antibody of the present invention might be attacked by immune system functions such as the complement system or by cell-mediated cytotoxicity, and thus reduces the number of or completely eradicating the cells showing undesired expression or over-expression of CD66c.

In another embodiment, the antibody of the present invention, or a fragment or derivative thereof is coupled to a labeling agent. Such antibodies are particularly suitable for diagnostic applications.

The diagnostic composition of the invention can be administered as an active agent alone or in combination with other agents.

A still further embodiment of the present invention relates to a method for detecting a tumor cell, which comprises (a) reacting the anti-CD66c antibody with a sample including a tumor cell, and (b) determining that the sample is a tumor if the sample is positive to the antibody. The sample may include, but is not limited to, lymphoid fluid, bone marrow, blood, and blood corpuscles. The tumor cell may preferably be a breast cancer cell, a lung cancer cell, a stomach cancer cell, a prostate cancer cell, or a liver cancer cell.

When used for screening a tumor cell, the anti-CD66c antibody may be conjugated with a label capable of indicating antigen-antibody reactivity. The label useful for this purpose may include a radioisotope, a fluorescent, a luminescent, a chromogen, and a dye.

Also, the anti-CD66c antibody of the present invention may be provided for a kit for diagnosing solid tumors.

The diagnostic kit may comprise a means for detecting an antigen-antibody reaction in addition to the anti-CD66c antibody. The detecting means may be an agent useful for performing a technique selected from the group consisting of flow cytometry, immunohistochemical staining, enzyme-linked immunosorbent assay (ELISA), radioimmunoassay (RIA), enzyme immunoassay (EIA), fluorescence immunoassay (FIA), and luminescence immunoassay (LIA). In this context, the label may be an enzyme such as HRP (horse radish peroxidase), a fluorescent such as FITC (fluorescein-thiocarbamyl ethylenediamine), a luminescent such as luminol, isoluminol, and lucigenin, or a radioisotope such as 125I, 3H, 14C, and 131I, but is not limited thereto. The conjugation with a label can be determined using a means for measuring an enzymatic reaction with a substrate, fluorescence, luminescence, or radiation. For example, the anti-CD66c antibody may be prepared for use in an ELISA kit or a strip kit.

In accordance with an embodiment thereof, the present invention addresses a pharmaceutical composition comprising the antibody, the nucleic acid molecule, the vector, or the host of the present invention. The antibody, the nucleic acid molecule, the vector, or the host of the present invention is used for treating or regressing solid cancer. The treatment or regression of solid tumors can be achieved by administering the nucleic acid molecule, the vector, or the host of the present invention at an effective dose to a subject in need thereof.

The term, "solid tumor", as used herein, defines an abnormal mass of tissue that usually does not contain cysts or liquid areas. The solid tumor may be benign (not cancer) or malignant (often referred to as cancer in the art). Examples of solid tumors to which the antibody according to the invention is applicable, include sarcoma, glioma, malignant neoplasm, mesothelioma, lymphoma, kidney cancer, lung cancer, breast cancer, cervical cancer, ovarian cancer, colorectal cancer, liver cancer, prostate cancer, pancreatic cancer, and head and neck cancer, and preferably breast cancer, lung cancer, colon cancer, stomach cancer, prostate cancer or liver cancer. The breast cancer may be a triple-negative breast cancer (TNBC), which can be detected as negative by using three diagnostic makers of HER2, estrogen receptor (ER), and progesterone receptor (PR), and thus is very difficult to be detected.

The therapeutic effect of solid tumors in accordance with the present invention includes suppressing effects on the migration, invasion, and metastasis of cancer cells (particularly, cancer stem cells) or tissues including cancer cells, and thus on alleviation of the malignancy of cancer as well as their growth inhibition (quantitative reduction) and apoptosis.

In order to maximize the effect of the antibody of the present invention in combination with an inhibitor blocking the binding loop of PD-1 or PD-L1, the induction of T-cell activation secretes cytokine and increases the PD-L1 protein level on the surface of cancer cells and immune cells, when the cancer cells and immune cells are co-cultured, in Example 7. This can be expected to provide a higher anti-cancer effect, when the PD-1 or PD-L1 binding inhibitor is used in combination with the antibody of the present invention. Antibody therapeutic agents for PD-1 and PD-L1 as immune checkpoint inhibitors have been approved and applied to clinical trial. The composition may further comprise a PD-I or PD-L1 binding inhibitor.

As used herein the term "subject" or "patient" refers to a mammal, including a primate such as a human, a monkey, etc., and a rodent such as a mouse, a rat, etc., that is afflicted with, or has the potential to be afflicted with a solid tumor or symptom and thus which is in need of alleviation, prevention, and/or treatment of the solid tumor.

The administration of the antibody or its fragment according to the present invention may be conducted in any acceptable manner. For example, a therapeutic agent including the anti-CD66c antibody as an active ingredient is administered orally or parenterally, and preferably parenterally, to a subject, e.g., a human or an animal that has tumor cells. The therapeutic agent may include a pharmaceutically acceptable excipient, and the dose of the therapeutic agent may vary depending on the condition of the patient, and may range from, for example, 3 mg to 6,000 mg per day. The therapeutic agent may take such forms as liquids, powders, emulsions, suspensions or injections, but is not limited thereto.

Further, the present invention provides a method for treating acute or chronic myelogenous or lymphocytic leukemia, using at least one selected from among an antibody to an antigen-determining region of CD66c, a fragment of the antibody (F(ab')$_2$, Fab, Fv, etc.), and a ligand to an antigen-determining region of CD66c.

An antibody or a fragment thereof may be monoclonal or polyclonal, and may be derived from humans or animals. The anti-CD66c antibody or its fragment may further comprise the toxin described above. The toxin may be fused, coupled, conjugated or linked to the antibody using a well-known technique.

The pharmaceutical composition of the present invention may be administered as a single active agent or in combination with any other agents that are preferable for the treatment of the disease of interest. In addition, the antibody of the present invention may be used in conjunction with other anticancer therapies, such as chemotherapy, radiotherapy, cell therapy, etc. Various, well-known anticancer agents may be used in chemotherapy or cell therapy.

Another embodiment of the present invention provides a method for screening a therapeutic agent or inhibitor of solid tumors, comprising contacting a candidate compound with CD66c, particularly an antigen-determining region located at a non-catalytic domain of CD66c, and classifying the candidate compound as a potential therapeutic agent for solid tumors if the candidate compound is determined to bind to the antigen-determining region. A further embodiment of the present invention provides a pharmaceutical composition for treating solid tumors, comprising the screened therapeutic agent for solid tumors as an active ingredient.

The candidate compound may be at least one selected from the group consisting of various synthetic or naturally occurring compounds, polypeptides, oligopeptides, peptides or protein constructs (e.g., antibodies, antigen-binding fragments, peptibodies, nanobodies, etc.), polynucleotides, oligonucleotides, antisense-RNA, shRNA (short hairpin RNA), siRNA (small interference RNA), aptamers, and extracts from natural products.

Binding between a candidate compound and an antigen-determining region can be determining by detecting the formation of a complex, which can be conducted using various methods known in the art. By way of example, typical enzyme reactions, fluorescence, luminescence and/or radiation may be detected to confirm the binding of the candidate compound to the antigen-binding region. In detail, techniques available for the detection of the complex include, but are not limited to, immunochromatography, immunohistochemistry, enzyme-linked immunosorbent assays (ELISA), radioimmunoassays (RIA), enzyme immunoassays (EIA), fluorescence immunoassays (FIA), luminescence immunoassays (LIA), and Western blotting.

Advantageous Effects

Provided are an antibody recognizing and binding to CD66c, a nucleic acid molecule encoding the antibody or an antigen-binding fragment of the antibody, a vector carrying the nucleic acid molecule, a host cell including the vector or the nucleic acid molecule, and use of the antibody or an antigen-binding fragment thereof in the alleviation, prevention or diagnosis of diseases related with CD66c such as solid tumors.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIG. 1 shows the result of cloning a gene of antibody from mouse 8F5 antibody and expressing it as a chimeric recombinant antibody and binding to the surface of CD66c antigen-positive A549 cells.

FIGS. 2a to 2c show the results of HPLC analysis of eight kinds of recombinant humanized antibodies selected first among 96 kinds of recombinant humanized antibodies. The results are shown as left measured at OD 220 nm and right measured at OD 280 nm for each antibody. The result represent whether the aggregation of antibodies and the impurities derived from antibody such as fragments are or not.

FIGS. 3a to 3e show similar degree of cell surface binding of recombinant humanized antibodies as compared to chimeric antibodies, as a result of confirming CD66c antigen positive cell surface binding of eight recombinant humanized antibodies firstly selected among 96 recombinant humanized antibodies FIGS. 4a and 4b show results of ELISA analysis for the binding ability of the five recombinant humanized antibodies selected from 96 recombinant humanized antibodies to the CD66c antigen. FIG. 4a shows the results for the CECACAM6 (CD66c) as an antigen and FIG. 4b shows the result for the CEACAM1 (CD66a) antigen.

FIGS. 5a and 5b show results of confirming antibody stability at a severe temperature condition for five recombinant humanized antibodies selected from among 96 recombinant humanized antibodies.

FIGS. 6a to 6d show the cell surface binding of CD66c antigen positive cell A549 of recombinant humanized antibody expressed in CHO cell.

FIG. 7a shows the results of secretion of IFN-gamma and perforin by activation of CD8+ T cells when the chimeric 8F5 antibody was treated under conditions of co-culture of human colorectal cancer LS174T cells and human CD8+ T cells, and FIG. 7b shows the increased cell death of colorectal cancer cell LS174T, when treated with the chimeric 8F5 antibody on the same condition as FIG. 7a.

FIG. 8 shows selective increase of IFN-gamma secretion only when chimeric 8F5 antibody is treated in the co-culture condition of CD8 T+ cells and various cancer cells, and shows the result of stomach cancer cell NCI-N87 cell and SNU-719 cell and liver cancer PLC/PRF/5 cell.

FIGS. 9a to 9C show that the CD66c antigen can inhibit T cell activity. FIG. 9a shows the results of measuring the intracellular level of IFN-gamma as a factor for T cell activity with a flow cytometer, and FIG. 9c is the result of measurement of secretion of IFN-gamma by ELISPOT. In the case of FIGS. 9b and 9c, when CD66c antigens are provide by different source, T cell activity was inhibited similarly.

FIGS. 10a and 10b are results showing that the chimeric 8F5 antibody increases activation of T cell and increases various activated cell surface marker proteins such as CD69, CD107, and CD25 under conditions of T cell activation caused by the attached OKT3 antibody.

FIGS. 11a and 11b show that chimeric 8F5 antibody activates CD4 and CD8-positive cells under MLR (Mixed Lymphocyte Reaction) conditions in which dendritic cells and PBMCs are mixed with each other.

FIG. 12a shows the result of ELISPOT analysis in which the IFN-gamma secretion is increased, when chimeric 8F5 antibody is treated when human stomach cancer cells isolated from ascites of stomach cancer patients are co-cultured with human PBMCs. FIGS. 12b and 12c show the similar results by performing additional ELISPOT experiments on three patients with CD66c antigen-positive stomach cancer.

FIGS. 13a and 13b show that the expression of PD-L1 antigen is increased on the surface of each of PBMC and A549 cancer cells by co-culturing with human PBMC and A549 non-small cell lung cancer cells and treating chimeric 8F5 antibody.

FIGS. 14a and 14b show that recombinant humanized antibodies have similar degrees of antibody function by increasing IFN-gamma secretion in co-culture of human PBMC with A549 cancer cells in a pattern similar to chimeric 8F5 antibody.

FIGS. 15a and 15b are results showing that the humanized 8F5 antibody has a cancer cell death function, when LS-174-T colorectal cancer cells or A549 non-small cell lung cancer cells are co-cultured with human PBMC.

FIGS. 16a to 16g show results of in vivo anti-cancer efficacy using an animal model of NOD/SCID mouse with chimeric 8F5 antibody. FIG. 16c shows the in vivo anti-cancer efficacy using an animal model of NOD/SCID mouse with humanized 8F5 antibody. FIGS. 16d and 16e to 16g show results of in vivo anti-cancer efficacy of the humanized 8F5 antibody by using different human PBMCs as the effector cells in the NSG immune-deficient mouse.

MODE FOR INVENTION

A better understanding of the present invention may be obtained through the following examples which are set forth to illustrate, but are not to be construed as limiting the present invention.

Example 1: Preparation of Anti-CD66c Chimeric Antibody 1.1. Gene Sequence Cloning of Anti-CD66c Antibody The 8F5 antibody gene was cloned using Mouse Ig-Primer Set (Millipore, Cat. #: 69831). The RNA isolated from the 8F5 hybridoma was PCR using the mouse Ig-primer set, inserted into a pGem-T vector (Promega, Cat. #: A3600), sequenced to confirm the DNA sequence, and the mouse antibody gene was identified through the IMGT site (www.imgt.org). The heavy chain variable region sequences and light chain variable region sequences of the analyzed 8F5 antibody are as follows.

TABLE 4

| Name | sequence | SEQ ID NO |
|---|---|---|
| 8F5-chimeric $V_H$-CDR1 | ASGYSFTDYTMN | 1 |
| 8F5-chimeric $V_H$-CDR2 | LINPFHGGTVSNQRFKV | 2 |
| 8F5-chimeric $V_H$-CDR3 | VRGDPVRHYYALAY | 3 |
| 8F5-chimeric $V_L$-CDR1 | GASENVYGTLN | 4 |
| 8F5-chimeric $V_L$-CDR2 | GATNLAD | 5 |
| 8F5-chimeric $V_L$-CDR3 | VATYYCQNVLSAPYT | 6 |
| 8F5-chimeric $V_H$ | EVQLQQSGPELVKPGASMKISCKASGYSFTDYTMNWVKQS HGKNLEWIGLINPFHGGTVSNQRFKVKATLTVDVSSNTAY MELLSLTSDDSAVYYCVRGDPVRHYYALAYWGQGTSVTVS S | 7 |
| 8F5-chimeric $V_L$ | DIQMTQSPASLSASVGETVTITCGASENVYGTLNWYQRKQ GKSPQLLIYGATNLADGMSSRFSGSGSGRQYSLKISSLHP DDVATYYCQNVLSAPYTFGGGTKLEII | 8 |
| 8F5-chimeric $V_H$ | Gaggtccagctgcaacagtctggacctgaactggtgaagc ctggagcttcaatgaagatatcctgcaaggcttctggtta ctcattcactgactacaccatgaactgggtgaagcagagc catggaaagaaccttgagtggattggacttattaatcctt tccatggtggtactgtctccaaccagaggttcaaggtcaa | 62 |

TABLE 4-continued

| Name | sequence | SEQ ID NO |
|---|---|---|
|  | ggccacattaactgtagacaagtcatccaacacagcctac<br>atggagctcctcagtctgacatctgacgactctgcggtct<br>attactgtgtaagaggtgacccggtccgccattactatgc<br>tttggcctactggggtcagggaacctcagtcaccgtctcc<br>tca |  |
| 8F5-chimeric $V_L$ | gacatccagatgactcagtctccagcttcactgtctgcat<br>ctgtgggagaaactgtcaccatcacatgtggagcaagtga<br>gaatgtttacggtactttaaattggtatcagcggaaacag<br>ggaaaatctcctcagctcctgatctatggtgcaaccaact<br>tggcagatggcatgtcatcgaggttcagtggcagtggttc<br>tggtagacagtattctc | 63 |

1-2. Production of Chimeric Antibody

Based on the amino acid sequence of the constructed anti-CD66c mouse antibody 8F5, an anti-CD66c chimeric antibody was prepared.

1-2-1. Plasmid Production

For expressing the anti-CD66c chimeric antibody, a plasmid for heavy chain and a light chain expression plasmid were respectively prepared. POptiVEC (Invitrogen) vector was used as the light chain expression plasmid, and pcDNA3.3 (Invitrogen) vector was used as the heavy chain expression plasmid.

In order to express the variable region coding cDNA and the constant region coding cDNA of each antibody as a continuous amino acid sequence without additional amino acid insertion, the coding sequence of the cloned variable region and the known human IgG1 constant region (heavy chain) and the kappa constant region (light chain) coding sequences were synthesized (Bioneer). The synthesized heavy gene and light chain gene were cut with restriction enzymes Xho I and Sal I and the light chain gene fragment was ligated to the pOptiVec vector and the heavy chain gene fragment was ligated to the pcDNA3.3 vector, respectively, to construct a complete antibody expression plasmid (pcDNA3.3-anti-CD66c heavy chain expression plasmid and pOptiVEC-anti-CD66c light chain expression plasmid).

1-2-2. Transfection

The prepared pcDNA3.3-anti-CD66c heavy chain expression plasmid and pOptiVEC-anti-CD66c light chain expression plasmid were transfected into CHO cell-derived DG44 cells (Invitrogen).

Three days prior to transfection, DG44 cells in suspension were adapted to MEMS medium containing 5% FBS to convert them into adherent cells and to improve transfection efficiency. Transfection was performed on a 6-well plate using the ViaFect transfection regent (Promega, Cat. #: E4981). On the day before the transfection, DG44 cells adapted to the adhered state were prepared by subculturing at a concentration of $1 \times 10^5$ cells/well. The both pcDNA3.3 of anti-CD66c heavy chain expression plasmid and pOptiVEC of anti-CD66c light chain expression plasmids were used 2.0 ug and 1.5 ug, respectively, at a ratio of 1.0:0.75 for transfection.

Transfection was carried out for 48 hours. Flow cytometry was used to analyze the transfected cell population. As shown in FIG. 1, the expression of chimeric antibody was confirmed by A549 non-small cell lung cancer cell line. FIG. 1 shows the result of cloning an antibody gene from mouse 8F5 antibody and expressing it as a recombinant chimeric antibody and binding to the surface of CD66c antigen-positive A549 cells.

Example 2: Preparation of Humanized Anti-CD66c Monoclonal Antibody 2.1 Selection of Recombinant Antibody Sequence by in Silico Humanization CDRs (CDRH1: ASGYSFTDYTMN) SEQ ID NO: 1, CDRH2: SEQ ID NO: 2 (LINPFHGGTVSNQRFKV); CDRH3: SEQ ID NO: 3 (VRGDPVRHYYALAY); CDRL1: SEQ ID NO: 4 (GASENVYGTL); CDRL2: SEQ ID NO: 5 (GATNLAD); If CDR3: SEQ ID NO: 6 (VATYYCQNVLSAPYT) of the heavy chain of the mouse anti-CD66c antibody, 8F5 (heavy chain amino acid sequence: SEQ ID NO: 7, heavy chain encoding DNA: SEQ ID NO: 62; light chain amino acid sequence: SEQ ID NO: 8; light chain encoding DNA: SEQ ID NO: 63) were maintained as close to the antigen binding affinity as possible, or if the antigen binding affinity is equal or superior, the recombinant humanized antibody sequences based on the sequence of the framework region based on the germline sequence encoding the human antibody gene in silico method. The germline gene of human antibody used as a backbone of the recombinant humanized antibody sequence is most similar to the heavy chain and light chain of the mouse CD66c antibody 8F5, respectively, as shown in Table 5. The amino acid sequence and the nucleic acid sequence of the heavy chain variable region and the light chain variable region of the mouse CD66c antibody and the CDR sequences of the heavy chain variable region and the light chain variable region are shown in Table 6.

TABLE 5

| Human Ab Germline | |
|---|---|
| Heavy chain | Light chain |
| IGHV1-69-2*01 | IGKV1-27*01 |
| IGHV1-2*02 | IGKV1-5*01 Homo sapiens |
| IGHV1-46*01 | IGKV1-39*01 Homo sapiens |

12 heavy chain variable regions and 8 light chain variable regions were selected as the humanized 8F5 antibody sequence selected using the human antibody germline gene sequence, as shown in Table 3. The amino acid sequences of the heavy chain variable region and the light chain variable region, CDR sequences, and the framework sequences of the selected humanized antibody are shown in Tables 6 to 8. The heavy chain variable region and the light chain variable region of the chimeric antibody and the humanized antibody are shown in Table 1. It is preferable that the mouse antibody and the humanized antibody have the same amino acid sequences of heavy chain CDR3 and light chain CDR2. The bold and underlined parts in Table 6 are the CDR sequences of antibody. The bold and underlined parts in Table 7 indicate the modified amino acid.

TABLE 6

| Antibody number | combination | name | Amino acid sequence |
|---|---|---|---|
| 3043 | Vk8 + VH6 | VH6 | QVQLVQSGAEVKKPGASMKISCKASGYSFTDYTMNWVKQAPGQNLEWIGLINPFHGGTVSNQRFKVKATLTVDVSTNTAYMELSRLRSDDTAVYYCVRGDPVRHYYALAYWGQGLTVTVSS |
|  |  | Vk8 | DIQMTQSPSTLSASVGDRVTITCRASENVYGTLNWYQRKPGKAPKLLIYGATNLADGMPSRFSGSGSGTEYTLTISSLQPDDFATYYCQNVLSAPYTFGGGTKLEIK |
| 3058 | Vk8 + VH11 | VH11 | QVQLVQSGAEVEKKPGASVKISCKASGYSFTDYTMHWVKQAPGQNLEWIGLINPFGGSTSYAQKFKGRVTMTRDTSTNTAYMELSRLRSDDTAVYYCVRGDPVRHYYALAYWGQGTLVTVSS |
|  |  | Vk8 | DIQMTQSPSTLSASVGDRVTITCRASENVYGTLNWYQRKPGKAPKLLIYGATNLADGMPSRFSGSGSGTEYTLTISSLQPDDFATYYCQNVLSAPYTFGGGTKLEIK |
| 2938 | Vk5 + VH7 | VH7 | QVQLVQSGAEVKKPGASMKISCKASGYSFTDYTMNWVRQAPGQGLEWIGLINPFHGGTVSNQRFKVKATLTVDVSTNTAYMELSRLRSDDTAVYYCVRGDPVRHYYALAYWGQGLTVTVSS |
|  |  | Vk5 | DIQMTQSPSTLSASVGDRVTITCGASENVYGTLAWYQRKPGKAPKLLIYGATNLADGVPSRFSGSGSGREYTLTISSLQPDDFATYYCQNVLSAPYTFGGGTKLEIK |
| 3007 | Vk7 + VH6 | VH6 | QVQLVQSGAEVKKPGASMKISCKASGYSFTDYTMNWVKQAPGQNLEWIGLINPFHGGTVSNQRFKVKATLTVDVSTNTAYMELSRLRSDDTAVYYCVRGDPVRHYYALAYWGQGTLVTVSS |
|  |  | Vk7 | DIQMTQSPSTLSASVGDRVTITCGASENVYGTLNWYQRKPGKAPKLLIYGATNLADGVPSRFSGSGSGTEYLTLTISSLQPDDFATYYCQNVLSAPYTFGGGTKLEIK |
| 3019 | Vk7 + VH10 | VH10 | QVQLVQSGAEVKKPGASVKVSCKASGYSFTDYTMNWVKQAPGQNLEWIGLINPFHGGTVSNQRFKVKATMTVDVSTNTAYMELSRLRSDDTAVYYCVRGDPVRHYYALAYWGQGTLVTVSS |
|  |  | Vk7 | DIQMTQSPSTLSASVGDRVTITCGASENVYGTLNWYQRKPGKAPKLLIYGATNLADGVPSRFSGSGSGTEYTLTISSLQPDDFATYYCQNVLSAPYTFGGGTKLEIK |
| 3010 | Vk7 + VH7 | VH7 | QVQLVQSGAEVKKPGASMKISCKASGYSFTDYTMNWVRQAPGQGLEWIGLINPFHGGTVSNQRFKVKATLTVDVSTNTAYMELSRLRSDDTAVYYCVRGDPVRHYYALAYWGQGTLVTVSS |
|  |  | Vk7 | DIQMTQSPSTLSASVGDRVTITCGASENVYGTLNWYQRKPGKAPKLLIYGATNLADGVPSRFSGSGSGTEYTLTISSLQPDDFATYYCQNVLSAPYTFGGGTKLEIK |
| 3004 | Vk7 + VH5 | VH5 | QVQLVQSGAEVKKPGASVKISCKASGYSFTDYTMNWVRQAHGQNLEWIGLINPFHGGTVSNQRFKVKATLTVDVSTNTAYMELSRLRSDDTAVYYCVRGDPVRHYYALAYWGQGTLVTVSS |
|  |  | Vk7 | DIQMTQSPSTLSASVGDRVTITCGASENVYGTLNWYQRKPGKAPKLLIYGATNLADGVPSRFSGSGSGTEYTLTISSLQPDDFATYYCQNVLSAPYTFGGGTKLEIK |
| 3046 | Vk8 + VH7 | VH7 | QVQLVQSGAEVKKPGASMKISCKASGYSFTDYTMNWVRQAPGQGLEWIGLINPFHGGTVSNQRFKVKATLTVDVSTNTAYMELSRLRSDDTAVYYCVRGDPVRHYYALAYWGQGTLVTVSS |
|  |  | Vk8 | DIQMTQSPSTLSASVGDRVTITCRASENVYGTLNWYQRKPGKAPKLLIYGATNLADGMPSRFSGSGSGTYETLTISSLQPDDFATYYCQNVLSAPYTFGGGTKLEIK |

TABLE 7

| Name | CDR1 | SEQ ID NO | CDR2 | SEQ ID NO | CDR3 | SEQ ID NO |
|---|---|---|---|---|---|---|
| $V_H$-Chimeric | ASGYSFTDYTMN | 1 | LINPFHGGTVSNQRFKV | 2 | GDPVRHYYALAY | 3 |
| VH5, 6, 7, 10 | ASGYSFTDYTMN | 1 | LINPFHGGTVSNQRFKV | 2 | GDPVRHYYALAY | 3 |
| VH11 | ASGYSFTDYTMH | 9 | LINPFGGSTSYAQKFKG | 10 | GDPVRHYYALAY | 3 |

TABLE 7-continued

| Name | CDR1 | SEQ ID NO | CDR2 | SEQ ID NO | CDR3 | SEQ ID NO |
|---|---|---|---|---|---|---|
| V_L-Chimeric | GASENVYGTLN | 4 | GATNLAD | 5 | VATYYCQNVLLAPYT | 6 |
| VK5 | GASENVYGTLA | 11 | GATNLAD | 5 | FATYYCQNVLSAPTY | 13 |
| VK7 | GASENVYGTLN | 4 | GATNLAD | 5 | FATYYCQNVLLAPYT | 13 |
| VK8 | RASENVYGTLN | 12 | GATNLAD | 5 | FATYYCQNVLSAPYT | 13 |

TABLE 8

| Name | FR1 | SEQ ID NO | FR2 | SEQ ID NO | FR3 | SEQ ID NO | FR4 | SEQ ID NO |
|---|---|---|---|---|---|---|---|---|
| V_H-Chimeric | EVQLQQSGPELVKPGASMKISCK | 22 | WVKQSHGKNLEWIG | 32 | NQRFKVKATLTVDVSSNTAYMELLSLTSDDSAVYYCVR | 42 | WGQGTSVTVSS | 52 |
| VH5 | QVQLVQSGAEVKKPGASVKISCK | 23 | WVRQAHGQNLEWIG | 33 | NQRFKVKATLTVDVSTNTAYMELSRLRSDDTAVYYCVR | 43 | WGQGTLVTVSS | 53 |
| VH6 | QVQLVQSGAEVKKPGASMKISCK | 24 | WVKQAPGQNLEWIG | 34 | NQRFKVKATLTVDVSTNTAYMELSRLRSDDTAVYYCVR | 44 | WGQGTLVTVSS | 54 |
| VH7 | QVQLVQSGAEVKKPGASMKISCK | 25 | WVRQAPGQGLEWIG | 35 | NQRFKVKATLTVDVSTNTAYMELSRLRSDDTAVYYCVR | 45 | WGQGTLVTVSS | 55 |
| VH10 | QVQLVQSGAEVKKPGASVKVSCK | 26 | WVKQAPGQNLEWIG | 36 | NQRFKVKATMTVDVSTNTAYMELSRLRSDDTAVYYCVR | 46 | WGQGTLVTVSS | 56 |
| VH11 | QVQLVQSGAEVKKPGASVKISCK | 27 | WVKQAPGQNLEWIG | 37 | AQKFKGRVTMTRDTSTNTAYMELSRLRSDDTAVYYCVR | 47 | WGQGTLVTVSS | 57 |
| V_L-Chimeric | DIQMTQSPASLSASVGETVTITC | 28 | WYQRKQGKSPQLLIY | 38 | GMSSRFSGSGSGRQYSLKISSLHPDD | 48 | FGGGTKLEH | 58 |
| VK5 | DIQMTQSPSTLSASVGDRVTITC | 29 | WYQRKPGKAPKLLIY | 39 | GVPSRFSGSGSGRQYSLKISSLHPDD | 49 | FGGGTKLEIK | 59 |
| VK7 | DIQMTQSPSTLSASVGDRVTITC | 30 | WYQRKPGKAPKLLIY | 40 | GVPSRFSGSGSGTEYTLTISSLQPDD | 50 | FGGGTKLEIK | 60 |
| VK8 | DIQMTQSPSTLSASVGDRVTITC | 31 | WYQRKPGKAPKLLIY | 41 | GMPSRFSGSGSGTEYTLTISSLQPDD | 51 | FGGGTKLEIK | 61 |

2.2 Expression and Analysis of Recombinant Humanized Antibodies

The sequences of selected antibody were expressed in 293 cells in the form of human IgG1 by connecting the human IgG1 heavy chain constant region and the kappa light chain constant region, respectively. Seven days after the transfection, the recombinant humanized antibody was purified using KanCap A resin (Kaneca).

The purified antibody was quantitated by measuring at OD 280 nm and SDS-PAGE was performed. The purity and the aggregation of the antibody were analyzed by analyzing with 280 nm and 220 nm by HPLC using Sepax Zenix-C SEC-300 size exclusion column (Sepax Technologies) (FIGS. 2A to 2C)

2.3 Cell Binding and Antigen Binding Analysis of Recombinant Humanized Antibodies 2-3-1 Cell Binding Assay Each expressed 96 recombinant humanized antibody was poured and reacted in a test tube containing the same amount (1 ug) of CD66c-positive A549 non-small-cell lung cancer cell line at 4° C. for 30 minutes, washed with PBS, and treated with FITC-conjugated goat anti-Human IgG (Di-Nona Inc, Korea) was added and incubated at 4° C. for 15 minutes. After washing with PBS, the cells were analyzed with a flow cytometer (Stratedigm, S1000EXi) and the results are shown below.

Among the 96 recombinant humanized antibody candidates, eight were firstly selected based on the degree of expression, the presence of aggregation, and the degree of cell binding (Table 9 and Table 10, FIGS. 3A to 3E). Tables 9 and 10 are the results of analysis of primary selected anti-CD66c humanized antibody and chimeric 8F5, and Table 10 shows the results of flow cytometer analysis.

similar binding affinity to the target antigen-positive cells to the chimeric antibody were firstly selected from 96 humanized candidate antibodies As shown in FIG. 3, the actual cell binding profile was similar to that of chimeric antibody, and 8 kinds of humanized antibodies were determined by multiplying the antibody positivity (% gated) with the mean fluorescence (mean), and by the selecting the humanized antibodies within 20% compared with the chimeric antibody. In general, when the mouse antibody CDR region sequence is inserted into the framework region of the humanized antibody at the time of the production of the humanized antibody, the antibody binding affinity is sharply decreased due to the change of the original protein structure. In considering the general property of humanized antibody, very good humanized antibodies were be selected in the present invention.

2-3-2 Antigen Binding Assay

Among the eight selected recombinant humanized antibodies, five kinds of recombinant humanized antibodies exhibiting a high binding affinity as compared to that of the chimeric antibody were selected and analyzed for their binding affinity to CD66c antigen and similar CD66 antigens by ELISA, respectively.

TABLE 9

| | No. | | | | | | | |
|---|---|---|---|---|---|---|---|---|
| | #71 | #86 | #93 | #43 | #51 | #45 | #41 | #74 |
| | | | | Protein ID | | | | |
| | 3043 | 3058 | 2938 | 3007 | 3019 | 3010 | 3004 | 3046 |
| H & L combination | Vk8 + VH6 | Vk8 + VH11 | Vk5 + VH7 | Vk7 + VH6 | Vk7 + VH10 | Vk7 + VH7 | Vk7 + VH5 | Vk8 + VH7 |
| Well | F11 | H2 | H9 | D7 | E3 | D9 | D5 | G2 |
| OD 280 nm | 3.54 | 3.86 | 3.32 | 4.01 | 4.03 | 3.5 | 3.56 | 3.54 |
| Volume (ml) | 0.25 | 0.25 | 0.25 | 0.25 | 0.25 | 0.25 | 0.25 | 0.25 |
| Conc. (mg/ml) | 2.52 | 2.71 | 2.36 | 2.85 | 2.86 | 2.49 | 2.53 | 2.52 |
| Yield (mg) | 0.66 | 0.71 | 0.61 | 0.74 | 0.74 | 0.65 | 0.66 | 0.66 |
| extinction coefficient | 102190 | 103680 | 102190 | 102190 | 102190 | 102190 | 102190 | 102190 |
| MW (Da) | 72750 | 72691 | 72616 | 72633 | 72521 | 72604 | 72669 | 7272 |

TABLE 10

| No. | Protein ID | H & L combination | % gated | Mean | % (% gated × mean) |
|---|---|---|---|---|---|
| Chimeric antibody | ** | ** | 73 | 619 | 100.0 |
| #71 | 3043 | Vk8 + VH6 | 69 | 686 | 104.8 |
| #86 | 3058 | Vk8 + VH11 | 72 | 645 | 102.8 |
| #93 | 2938 | Vk5 + VH7 | 71 | 611 | 96.0 |
| #43 | 3007 | Vk7 + VH6 | 71 | 565 | 88.8 |
| #51 | 3019 | Vk7 + VH10 | 70 | 561 | 86.9 |
| #45 | 3010 | Vk7 + VH7 | 70 | 554 | 85.8 |
| #41 | 3004 | Vk7 + VH5 | 71 | 541 | 85.0 |
| #74 | 3046 | Vk8 + VH7 | 71 | 523 | 82.2 |

TABLE 11

| Protein ID | HC & LC combination |
|---|---|
| 3043 | Vk8 + VH6 |
| 3058 | Vk8 + VH11 |
| 2938 | Vk5 + VH7 |
| 3007 | Vk7 + VH6 |
| 3019 | Vk7 + VH10 |

Table 9 shows the degree of expression, the presence or absence of aggregation, and the degree of cell binding of 8 selected antibodies. Specifically, the expression levels and the molecular weights of the 8 selected antibodies were summarized. In addition, according to the results of flow cytometry in Table 10, it was confirmed that the eight recombinant humanized antibodies exhibited cell binding strengths of ±20% which showed very similar cell binding strength to chimeric antibodies. As a result, the 8 antibody being normally expressed and having few aggregations formed due to the instability of the protein itself, and the Antigen CD66c (CEACAM6; Sino Biological, Inc.) and CEACAM1 antigen (Sino Biological, Inc.) were coated on a 96-well plate at 100 ng per well and then blocked. The primary antibody was diluted serially three fold from 10 ug/ml at initial concentration and was bound at 37° C. for 1 hour, and goat anti-Human Ig-HRP conjugate (Jackson ImmunoResearch) as a secondary antibody was diluted 1:10,000 and incubated at 37° C. for 30 minutes. The washing was carried out at three times between each step, and the TMB reaction was performed, stopped with 1N $H_2SO_4$ solution at the same amount of TMB solution (100 ul) and then OD value was measured at 450 nm.

As a result of the experiment, the binding affinities to CD66c antigen of the five kinds of recombinant humanized antibodies selected from among 96 kinds of recombinant humanized antibodies are shown in FIG. 4a, Table 12, FIG. 4b and Table 13. FIG. 4a and Table 12 show the binding capacity of the antibodies to CECACAM6 CD66c) antigen, and FIG. 4b and Table 13 are the results for the CEACAM1 (CD66a) antigen.

From the binding affinity of antibodies to the antigen in FIG. 4a, Table 12, FIG. 4b and Table 13, all antibodies to CECACAM6 showed a similar binding profile to the chimeric antibody to CEACAM6 and were divided into the groups that did not bind or bound weakly CEACAM1.

TABLE 12

| Antibody concentration (ng/ml) | chi 8F5 | hu 3043 | hu 3058 | hu 2938 | hu 3007 | hu 3019 |
|---|---|---|---|---|---|---|
| 10000.00 | 3.17 | 2.73 | 2.87 | 3.43 | 3.37 | 3.13 |
| 3333.33 | 3.41 | 2.95 | 3.18 | 3.27 | 3.24 | 3.26 |
| 1111.11 | 3.30 | 2.74 | 3.19 | 3.16 | 3.23 | 3.34 |
| 370.37 | 3.30 | 2.92 | 2.80 | 3.08 | 3.16 | 3.23 |
| 123.46 | 2.83 | 2.29 | 2.22 | 2.56 | 2.90 | 3.04 |
| 41.15 | 2.02 | 1.73 | 1.38 | 1.72 | 2.17 | 2.45 |
| 13.72 | 1.15 | 1.37 | 1.06 | 1.15 | 1.64 | 1.77 |
| 4.57 | 0.80 | 0.91 | 0.74 | 0.65 | 1.02 | 1.32 |
| 1.52 | 0.53 | 0.70 | 0.53 | 0.48 | 0.79 | 0.95 |
| 0.51 | 0.41 | 0.49 | 0.38 | 0.36 | 0.64 | 0.80 |
| 0.17 | 0.40 | 0.41 | 0.37 | 0.30 | 0.53 | 0.68 |

TABLE 13

| Antibody concentration (ng/ml) | chi 8F5 | hu 3043 | hu 3058 | hu 2938 | hu 3007 | hu 3019 |
|---|---|---|---|---|---|---|
| 10000.00 | 1.21 | 0.91 | 0.42 | 0.32 | 1.01 | 0.99 |
| 3333.33 | 1.24 | 1.22 | 0.31 | 0.27 | 1.15 | 1.07 |
| 1111.11 | 1.21 | 1.17 | 0.19 | 0.21 | 1.06 | 1.02 |
| 370.37 | 1.13 | 0.80 | 0.12 | 0.14 | 0.92 | 0.89 |
| 123.46 | 0.95 | 0.70 | 0.07 | 0.10 | 0.82 | 0.79 |
| 41.15 | 0.82 | 0.61 | 0.07 | 0.07 | 0.66 | 0.58 |
| 13.72 | 0.51 | 0.43 | 0.05 | 0.06 | 0.46 | 0.41 |
| 4.57 | 0.28 | 0.27 | 0.05 | 0.05 | 0.27 | 0.24 |
| 1.52 | 0.16 | 0.16 | 0.05 | 0.05 | 0.18 | 0.16 |
| 0.51 | 0.10 | 0.10 | 0.04 | 0.05 | 0.11 | 0.11 |
| 0.17 | 0.08 | 0.08 | 0.04 | 0.04 | 0.09 | 0.08 |

2.4 Stability Analysis of Recombinant Humanized Antibodies

The experiments were conducted to determine the stability of the antibodies by leaving the five recombinant humanized antibodies of Example 3.3 selected by the binding profile to antigen and cell under high temperature conditions.

The stability was determined by performing the binding experiments using 8-anilino-1-naphthalenesulfonic acid (ANS, Sigma). ANS is a compound that can detect the denaturation of proteins by measuring the change in fluorescence wavelength between the binding to and not binding to hydrophobic sites exposed when protein is denatured.

The recombinant humanized antibody was adjusted to a concentration of 0.2 mg/ml using PBS (phosphate buffered saline), and left at 50° C. for 4 hours under severe conditions. 0.2 μg/ml of ANS solution was mixed at 20 μl with 500 μl of the diluted solution of antibody to be analyzed dilution to be measured, and analyzed after 5 minutes later with a fluorescent reader at 360 nm excitation and 460 nm emission conditions. In addition, the ANS reagent reaction was also measured at a temperature of 70° C. for additional 30 minutes.

FIGS. 5a and 5b show the results of confirming the antibody stability of the five recombinant humanized antibodies shown in Table 11 under severe temperature conditions. That is, the reactivity of the ANS reagent was measured by fluorescence after leaving the antibody at 50° C. for 4 hours under the sever condition, and further left at 70° C. for 30 minutes. As shown in the results of the experiment of FIG. 5a, most 5 kinds antibodies showed little ANS response when the antibodies were left at the temperature of 50° C. for 4 hours, but the greatly increased fluorescence value of the antibodies when the antibodies were additional left at 70° C. for 30 minutes. Among them, the recombinant antibody having protein ID: 3058 exhibited the smallest increased fluorescence value, and thus showed the most stable property in the temperature change among the five recombinant humanized antibodies.

In order to measure the change rate of ANS reagent reactivity, ANS reagent reactivity was analyzed with a fluorescent reader in the same manner as above after leaving the antibodies for 4 hours at a refrigeration condition (4±2° C.) and a temperature of 62° C. The fluorescence value variability of the antibody against the ANS reagent can be determined by obtaining the difference between the fluorescence value measured at low temperature conditions (e.g., 4° C.) and the fluorescence value measured at high temperature conditions (e.g., 62° C.) and dividing with the fluorescence value measured at low temperature conditions.

Fluorescence value variability=(fluorescence value measured at high temperature condition−fluorescence value measured at low temperature condition)/(fluorescence value measured at low temperature condition)         [Mathematical Equation]

As shown in FIG. 5b, the reaction was allowed for 4 hours at a temperature of 62° C. which was somewhat increased from temperature (50° C.), and then the ANS reagent reactivity was confirmed. Five recombinant humanized antibodies and the chimeric antibodies showed little ANS response under refrigerated conditions, but increased with increasing temperature. However, Chimeric 8F5 antibody showed the reactivity of ANS reagent increased to 1,406% by keeping the temperature condition at 62° C. but the precipitates occurred to be unstable. However, the five humanized antibodies showed significantly lower variability of ANS reagent reactivity than chimeric antibodies, and no precipitates were produced. In particular, the humanized antibodies Protein ID 3019 and Protein ID 3058 had variability of ANS reagent reactivity of 114% and 133%, respectively, and thus were considered as most stable antibodies. The meaning of increased ANS reagent reactivity refers to the increased exposure of the hydrophobic amino acid placed inside the protein structure, which is responsible for the denaturation of the protein structure and the resulting protein aggregate, i.e., precipitate formation. The humanized antibody according to the present invention is considered to be stable antibody having the ANS reactivity variation of less than 200%. The ANS reactivity variation of less a change of less than 200% is considered to be very low, and over the value, a more significant change in protein structure is considered to be the observation of ANS reactivity. Accordingly, the humanized antibody according to the present invention has similar antigen binding and cell binding ability to chimeric antibody, and the increased physical stability of the antibody protein itself, such facts are a very excellent feature in the drugability for the therapeutic antibody.

2.5 CHO Cell Expression and Analysis of Recombinant Humanized Antibody

The five recombinant humanized antibodies selected in Example 2.3 were expressed in CHO cells used for expressing most therapeutic antibodies and analyzed. The light chain variable region DNA sequence and heavy chain variable region DNA sequence to construct the selected five recombinant humanized antibodies were performed by the codon optimization, synthesized, and ligated with the human IgG1 constant region gene by overlay PCR method. The product was cut with XhoI and EcoRI and ligated into the pcDNA3.4 vector (Life Technology). Table 11 shows the light chain and heavy chain combinations of humanized antibodies selected for CHO cell expression.

The DNA primer sequences used for PCR on the variable region and constant region gene are shown in Table 14 below.

Enrichment Kit (Ebioscience, cat. #: 8804-6812-74). $1\times10^6$ cells of CD8+ T cells and $2\times10^5$ cells of LS174T colorectal cancer cell were put into each well of a 6-well plate and a 10% FBS/RPMI medium were added to each well to be final volume of to 2 ml in each well and cultured. At this time, chimeric 8F5 antibody was treated to be 20 ug/ml. At 3rd and 5th days after the culture, 100 µl of each culture supernatant was taken and the amount of IFN-gamma and perform secretion of the culture supernatant were measured using a Human CD8 T+–Cell Magnetic Bead Panel (Millipore, Cat. #: HCD8MAG-15K) kit. After 7 days of incubation, the colorectal cancer cells LS174T were isolated and

TABLE 14

| Primer name | use | Target gene | sequences | SEQ ID NO |
|---|---|---|---|---|
| 8F01 | $1^{st}$ frag forward | VH6, VH7, VH10, VH11 | ATTACTCGAGGCCA CCATGAA | 64 |
| 8F02 | $1^{st}$ frag reverse | VH6, VH10, VH11 | AGTTGAAGCGCTGC TCACAGTCA | 65 |
| 8F03 | $2^{nd}$ frag forward | VH6, VH10, VH11 | GTGAGCAGCGCTTC AACTAAGGG | 66 |
| 3E04 | $2^{nd}$ frag reverse | VH6, VH7, VH10, VH11 | AGTCGAATTCTCAT TTCCCAGGAGAG | 67 |
| 8F04 | $1^{st}$ frag reverse | VH7 | AGTTGAAGCAGAAG ACACTGTCA | 68 |
| 8F05 | $2^{nd}$ frag forward | VH7 | GTGTCTTCTGCTTC AACTAAGGG | 69 |
| 3E01 | $1^{st}$ frag forward | Vk5, Vk7, Vk8 | ATTACTCGAGGCCA CCATGAAGTGGG | 70 |
| 8F06 | $1^{st}$ frag reverse | Vk5, Vk7, Vk8 | AACAGTCCGCTTGA TCTCCAGCT | 71 |
| 3EL02(2) | $2^{nd}$ frag forward | Vk5, Vk7, Vk8 | GAGATCAAGCGGAC TGTTGCTGC | 72 |
| 3E08 | $2^{nd}$ frag reverse | Vk5, Vk7, Vk8 | ATTAGAATTCTCAG CACTCGCCGCGG | 73 |

The five (5) recombinant humanized antibodies were transiently transfected using the ExpiCHO (trademark) Expression System Kit (ThermoFisher, Cat. No. A29133), and the expressed antibodies were incubated with CD66c-positive A549 non-small lung cancer cell line and analyzed by flow cytometer, as shown in FIGS. 6a to 6c. All five recombinant humanized antibodies showed similar binding affinities to chimeric antibodies. The measured fluorescence value of the flow cytometer was divided by the antibody expression amount of the CHO culture medium to obtain the relative the binding affinity of antibody to the antibody expression amount, as shown in FIG. 6d. Therefore, it was confirmed that the recombinant humanized antibody was properly expressed in CHO cells. The binding affinity of the antibody to the cell surface was determined as 100%, and the relative change was shown in FIG. 6d.

Example 3: T Cell Activity and Cancer Cell Death by Chimeric 8F5 Antibody 3.1. T Cell Active Cytokine Analysis and Cancer Cell Viability Analysis Following Co-Culture of CD8+ T Cells and Cancer Cells LS174T CD8+ T cells were isolated from human blood cells using a MagniSort (registered trademark) Human CD8+ T cell stained with 7-AAD and the cell viability was measured by flow cytometer. FIG. 7a shows the results of secretion of IFN-gamma and perform by activated CD8+ T cells, when the chimeric 8F5 antibody was treated under the condition that LS174T cells and human CD8+ T cells were co-cultured. In the same condition of FIG. 7a, FIG. 7b showed the increased cell death of the colorectal cancer cell LS174T upon treatment with chimeric 8F5 antibody.

As shown in the graph of FIG. 7a, the secretion of IFN-gamma and perforin increased by activated CD8+ T cells and the cell death of LS174T increased, when the chimeric 8F5 antibody was treated under the condition that LS174T cells and human CD8+ T cells were co-cultured 3.2. Analysis of T Cell Activity Following Co-Culture of CD8+ T Cells and Various Cancer Cells CD8+ T cells were isolated as in Example 3.1, and T cell activity by chimeric 8F5 antibody was confirmed by ELISPOT method under co-culture conditions with various cancer cells. The IFN-gamma was analyzed with Human IFN gamma ELISPOT Ready-SET-Go! (Ebioscience; Cat. #: 88-7386-21). Volume of 100 µl per well containing $2.5\times10^4$ of CD8+ T cells and $5\times10^3$ cells of cancer cells, respectively were added to each well and the cells were incubated for 3 days, and then cell spots expressing IFN gamma were detected according to the method described in the kit.

FIG. 8 shows that IFN-gamma secretion has been selectively increased only when chimeric 8F5 antibody is treated in the co-culture condition of CD8+ T cells and various cancer cells such as NCI-N87, SNU-719 or PLC/PRF/5 cell.

As shown in FIG. 8, IFN-gamma secretion was selectively increased only when chimeric 8F5 antibody was treated in the co-culture condition of CD8+ T cells and various cancer cells.

Example 4: Inhibition of T Cell Activity by CD66c Antigen

To confirm whether T cell activity by 8F5 antibody was due to CD66c antigen, which is an antigen of 8F5 antibody, when human CD8+ T cell and the cancer cells were co-cultured, we examined whether human PBMC activation was inhibited by CD66c antigen.

Specifically, intracellular IFN-gamma (intracytosolic staining) staining and ELISPOT assay were used to measure T cell activation status.

OKT3 antibody was treated at 1 ug/ml and CD66c antigen was used at 10 ug/ml.

In order to stain IFN-gamma inside T-cells, Brefeldin A solution (1000×) (EBioscience, Cat. #: 00-4506-51) was diluted at 1× and pretreated 3 hours before staining, and was stained with Anti-Human IFN gamma PE (EBioscience, Cat. #: 12-7319-41) and FITC Mouse Anti-Human TCR-α/13 (BD Biosciences; Cat. #: 347773), and analyzed with flow cytometry.

FIGS. 9a to 9c show that the CD66c antigen can inhibit the T cell activity. FIG. 9a shows the results of measuring the intracellular level of IFN-gamma as a factor for T cell activity with a flow cytometer, and FIG. 9c is the result of measurement of secretion of IFN-gamma by ELISPOT. In FIGS. 9b and 9c, the T cell activity was inhibited similarly, when CD66c antigen of different source was used.

As shown in FIG. 9a, IFN-gamma positive T cells decreased from 15.55% to 8.87% when the CD66c antigen was co-treated, thereby suppressing the activity of T cells by the CD66 antigen.

The increase or inhibition of IFN-gamma production in human PBMCs was further confirmed by ELISPOT according the same method of Example 3.2, and two CD66c antigens which were produced internally by DINONA Inc. and purchased externally (Sino Biological Inc., Cat. #10823-H08H-50) were administered at 10 ug/ml. In both experiments, both cases treated with CD66c antigens showed a significant decrease in the number of IFN-gamma positive spots (FIG. 9b, 9c).

Example 5: Induction of T Cell Activation by Chimeric 8F5 Antibody 5.1. Increased T Cell Activation To determine the effect of the chimeric 8F5 antibody on the activation of T cells by the OKT3 antibody, $2 \times 10^6$ cells of human PBMC were placed in a 35-mm dish under the condition of an OKT3 antibody were fixed at a concentration of 0.3 mg/ml and cultured for 3 days. At this time, the chimeric 8F5 antibody was treated to be 20 ug/ml of concentration. After 3 days, the CD4+ T cells and CD8+ T cells were stained with Anti-Human CD69 PE (Ebioscience, Cat. #: 12-0699-41), Anti-Human CD107a (LAMP-1) PE (Ebioscience, Cat. #: 12-1079-41) and Anti-Human CD25 APC (Ebioscience, Cat. #: 17-0259-41). Anti-CD4-APC and Anti-CD8-FITC were stained with a reagent manufactured by DINONA INC (Korea). and each CD4 and CD8-positive group was gated on a flow cytometer. FIGS. 10a and 10b are results showing that the chimeric 8F5 antibody increases the T cell activation and increases various activated cell surface marker proteins such as CD69, CD107, CD25 and the like, under the conditions of T cell activation by the attached OKT3 antibody.

As shown in FIG. 10a, when the chimeric 8F5 antibody was administered to both CD4 and CD8-positive cells, the positive rate of CD69 marker of T cell activation was increased. As shown in FIG. 10b, the positive rates of CD107 and CD 25 marker of T cell activation were increased in the CD8-positive cells. The results of increased T cell activation caused by the chimeric 8F5 antibody in these T cell activation conditions indicate that the results of Example 3 were reflected as a result of the activation of the T cell itself. As described in Example 4, The T cell activity inhibition caused by CD66c antigen could be recovered by an anti-CD66c antibody, thereby maintaining or enhancing T cell activity to be cancer cell death.

5.2. Increased T Cell Activation in MLR

MLR (Mixed Lymphocyte Reaction) experiments were performed to further confirm T cell activation by the treatment of chimeric 8F5 antibody. Firstly, human PBMC was isolated and only the attached PBMC was treated with IL-4 ($5 \times 10^3$ units/ml, JWCreagene) and GM-CSF ($5 \times 10^3$ units/ml, JWCreagene) at two times for 3 days interval to differentiate to dendritic cells. Then, DC was mixed with PBMC of other human at mixing ratio of PBMC; DC of 5:1, and cultured for 5 days. The number of PBMC cells was $1.4 \times 10^6$ cells per each well in case of 12 well plates. After 5 days, the cells were separated and stained with CD4-FITC/CD107-PE/CD25-APC or CD8-FITC/CD107-PE/CD25-APC and analyzed by flow cytometer. FIGS. 11a and 11b show that chimeric 8F5 antibody activates CD4 and CD8-positive cells under MLR (Mixed Lymphocyte Reaction) conditions in which dendritic cells and PBMCs derived from the different source are mixed.

As shown in FIGS. 11a and 11b, the positive rates of CD107 and CD 25 in CD4 and CD8-positive cells was significantly increased by administration of chimeric 8F5 antibody even under MLR condition.

As a result, it is shown that chimeric 8F5 antibody can increase T cell activation itself, in both cases of T cell activation by OKT3 and T cell activation by allogeneic immune cells, thereby for chimeric 8F5 antibody to cause T cells' killing cancer cells.

Example 6: PBMC Activation in Patients with Stomach Cancer by Chimeric 8F5 Antibody To evaluate PBMC activation by chimeric 8F5 antibody in co-culture of PBMC with stomach cancer cell, the cancer cells were isolated from the ascites of actual patients with stomach cancer, but were not the cancer cell lines cultured in the laboratory, and immune cell activation was tested, when the chimeric 8F5 antibody was administered. The ascites samples of the patients with stomach cancer were obtained from Asan Medical Center, Seoul, Korea, and PBMCs were separated from the blood of the same patient having the stomach cancer cells of the samples in which CD66c positivity was confirmed from the ascites samples, and then were tested with ELISPOT as the method in Example 3.2.

FIG. 12a shows the result of ELISPOT analysis in which IFN-gamma secretion is increased, when the chimeric 8F5 antibody is treated on the co-culture condition that human stomach cancer cells isolated from ascites of patients with stomach cancer were co-cultured with human PBMCs. FIGS. 12b and 12c show similar results by performing additional ELISPOT experiments on CD66c antigen-positive stomach cancer patients.

When the chimeric 8F5 antibody was administered, the IFN-gamma positive spots were increased similarly to the level of OKT antibody administered as a positive control for T cell activation antibody (FIG. 12a). This result indicates that treatment of chimeric 8F5 antibody has induced the activation of autoimmune cells.

CD66c positive stomach cancer cells were additionally isolated from the ascites of different stomach cancer patients, mixed with PBMC isolated from normal human blood, and subjected to ELISPOT test in the same manner as in Example 3.2. As shown in FIG. 12b, IFN-gamma positivity was increased upon treatment with chimeric 8F5 antibody although there was somewhat different degree.

Example 7: Increase of PD-L1 Expression Level by Chimeric 8F5 Antibody

Cancer cells and PBMCs were co-cultured to evaluate the increase of PD-L1 expression by chimeric 8F5.

In order to analyze the change in immune checkpoint related protein by chimeric 8F5 antibody in co-culture of PBMC with LS-174-T (colorectal cancer cell line), NCI-N87 (stomach cancer cell line) or A549 (non-small cell lung cancer cell line), PD-L1 on the cell surface was observed. The each cancer cell and PBMC were mixed at a ratio of 1:3 ($0.5 \times 10^6$ cells: $1.5 \times 10^6$ cells per each well) in a 6-well plate and incubated for 24 hours with treatment of 20 μg/ml of antibody. PD-L1 on the surface of cancer cells and PBMC cells was stained with anti-Human CD274 (PD-L1, B7-H1) and PE (Ebioscience, Cat. #: 12-5983-41), and stained simultaneously with CD45-FITC (DINONA INC) to differentiate the cancer cells from PBMC cells.

FIG. 13a describes a result of the increased PD-L1 antigen on each cell surface of PBMC and A549 cancer cell, when human PBMC and A549 non-small lung cancer cells were co-cultured. FIG. 13b describes the increased expression of PD-L1 antigen on the surface of A549, NCI-N87 and LS-174-T cell lines.

As shown in FIGS. 13a and 13b, PD-L1 cell surface levels were increased in both cancer cells and PBMC by administration of chimeric 8F5 antibody. This indirectly demonstrates the activation of immune cells by the chimeric 8F5 antibody, indicating that it is possible to co-treat with inhibitors of PD-1/PD-L1 in future.

Example 8: PBMC Activation by Humanized 8F5 Antibody

The PBMC activation by humanized 8F5 antibody in co-culture of cancer cells and PBMCs was tested. Namely, five kinds of humanized 8F5 antibodies determined as shown in Table 11 were selected and an ELISPOT test was carried out as in Example 3.2. A549 non-small lung cancer cell line (lung adenocarcinoma cell line) was used for the co-cultured cancer cells, and the concentration of the administered antibody was 20 ug/ml. After three days later, IFN-gamma positive spots were identified and it was found that all five humanized 8F5 antibodies tested as in FIG. 14 increased the IFN-gamma-positive spots to the same level as the chimeric 8F5 antibody. Thus, it was confirmed that the humanized 8F5 antibodies are very similar functions to chimeric 8F5 antibodies.

FIGS. 14a and 14b show that recombinant humanized antibodies have similar degrees of antibody function by increasing IFN-gamma secretion in co-culture of human PBMC with A549 cancer cells in a pattern similar to chimeric 8F5 antibody.

Example 9: Cancer Cell Death by Humanized 8F5 Antibody 9-1: Co-Culture of Cancer Cells and CD3+ T Cells The apoptosis of cancer cells by humanized 8F5 antibody in co-culture with cancer cells and CD3+ T cells was evaluated. It was confirmed in vitro whether the cancer cells were killed by the activated T cells when the cells were co-cultured with LS-174-T cells, a colon cancer cell line, and human CD3-positive T cells. Specifically, cancer cells and T cells (or PBMC) were co-cultured in a volume of 100 μl per well at a ratio of $1 \times 10^4$ cells: $1 \times 10^5$ cells in a 96-well plate and treated with 10 μg/ml of antibody. After 3 days, the cell death degree of cancer cell was measured by Ez-Cytox (Daeil Biotech, EZ-1000) assay kit. The used antibodies were humanized 8F5 antibody (protein ID: 3019 (Table 11, E3), PD-1 (pembrolizumab same sequence antibody), PD-L1 (atezolizumab same sequence antibody), CEACAM6 (antibody having the same sequence of Bayer's anti-CEACAM6 antibody), respectively. FIG. 15a is a result of the cell death experiment, and the humanized 8F5 antibody according to the present invention showed the highest effect of cancer cell death.

9-2: Co-Culture of Cancer Cells and PBMC

The apoptosis of cancer cells by humanized 8F5 (protein ID: 3019) antibody in co-culture of cancer cells and PBMCs was evaluated.

Specifically, the evaluation was carried out in substantially the same manner as in Example 9-1, except that instead of the conditions for co-culturing LS-174-T cells of a colon cancer cell line, and human CD3-positive T cells, the A549 (lung adenocarcinoma cell line) cell line and two different PBMCs (Donor 1, Donor 2) were used. As shown in the experimental results of FIG. 15b, the cancer cells in wells treated with humanized 8F5 antibody (protein ID: 3019; E3, IgG1) showed the highest effect of cancer cell death in both types of PBMC conditions (FIG. 15b).

Example 10: Evaluation of Anticancer Efficacy Using Mouse Animal Model 10-1: Evaluation of Anticancer Efficacy of Chimeric 8F5 Antibody Using NOD/SCID Mouse Model In order to confirm the in vivo anticancer effect of chimeric 8F5 antibody, immunodeficient mouse NOD/SCID mouse was used. In the patents (US 10-1214177; US: 8404812), the anti-cancer effect was evaluated by using nude mouse. However, in the animal test set using the nude mouse, the immune cells showing anti-cancer effect was mouse immune cell as an effector cell, but not human immune cells. Thus, there is a limitation in proving that a candidate antibody can exhibit therapeutic efficacy in an actual human. Therefore, in order to evaluate the anti-cancer effect of the antibody against the cancer cell death in the animal test by the substantial human immune cells, the NOD/SCID mouse lacking the immune cells including mouse T cells was used for the animal experiment.

Asialo GM1 antibody was administered to deplete mouse natural killer (NK) cells one day before the administration of cancer cells and human PBMC. The next day, the cancer cells and PBMC were injected into mice. LS-174-T cells of colon cancer cells were injected subcutaneously at 5×10⁶ cells per mouse, and PBMC were injected intraperitoneally at 1×10⁷ cells. Four days after the injection of the cells, the antibody was intravenously injected at a dose of 10 mg/kg, and then the tumor mass of the subcutaneous injection cancer cells was observed and measured.

FIG. 16a used LS-174-T cells as colon cancer cells and FIG. 16b used A549 cells as non-small cell lung cancer cells for NOD-SCID mouse transplantation model and chimeric 8F5 antibody.

FIG. 16a shows the results of in vivo anti-cancer efficacy using a mouse animal model under humanization conditions in which human PBMCs were injected with chimeric 8F5 antibody. The chimeric 8F5 antibody-treated group showed the highest tumor growth inhibition (TGI) without an individual difference for PBMC donors.

In the first experimental set, the anti-cancer effect was 40%. The second experimental set showed an anticancer effect of 46%. FIG. 16a shows the transplantation model with the LS-174-T cells of colon cancer cells, and FIG. 16b shows the transplantation model with the non-small cell lung cancer cells, A549 cells. In both cases, chimeric 8F5 antibody treated group showed the highest anticancer effect. The group administered by the PD-1 antibody (the antibody having the same sequence of Nivolumab) had little or no anticancer effect, indicating that PD-L1 antigen expression on the cancer cell surface was very weak and thus could not respond.

As a result, it was confirmed that 8F5 chimeric antibody can induce anti-cancer effects in vivo human-immune cell engrafted colorectal cancer and lung cancer animal models.

10-2: Evaluation of Anticancer Efficacy of Humanized 8F5 Antibody Using NOD/SCID Mouse LS-174-T Model The anticancer efficacy was evaluated using an animal model in substantially the same manner as in Example 10-1, except that NOD-SCID mouse transplantation model using LS-174-T cells as colon cancer cells and humanized 8F5 antibody (protein ID: 3019, Table 11) was used. The experimental results are shown in FIG. 16c.

The same type of anticancer effect was also confirmed in the experimental set in which the humanized 8F5 antibody (protein ID: 3019) was administered to the same NOD-SCID mouse in the LS-174-T cell line transplantation model of colon cancer cells (FIG. 16c.)

10-3: Evaluation of Anticancer Efficacy of Humanized 8F5 Antibody Using NSG Mouse LS-174-T Model The animal experiments were conducted using NSG mouse with more severe immune deficiency than the NOD/SCID mice used in Examples 10-1 and 10-2. The NSG mouse is a mouse in which the activity of NK cells remained NOD/SCID mouse is completely removed by inducing a mutation in the IL2 receptor gamma (IL2Ry) gene in NOD/SCID mouse, to completely remove the effect of mouse immune cells being slightly remained and to evaluate the effects of only human-derived immune cells.

NSG mouse transplantation model using LS-174-T cells of colon cancer cells, humanized 8F5 antibody (protein ID: 3019, Table 11), Bayer's CEACAM6 antibody and Merck's CEACAM1 antibody were used. FIGS. 16d and 16g show in vivo anticancer efficacy of the humanized 8F5 antibody by using different human PBMCs as the effector cells in the NSG immune-deficient mouse.

The antibodies administered to the NSG mouse LS-174-T model were humanized 8F5 antibody (protein ID: 3019), Bayer's CEACAM6 antibody, and Merck's CEACAM1 antibody and their anti-cancer effects were compared. When compared to other antibodies having similar targets to that of humanized 8F5 antibody, humanized 8F5 antibody showed the most excellent anti-cancer effect.

FIG. 16d shows the average value of experimental results in which five different human PBMCs were used as effector cells. The group administered by humanized 8F5 antibody (protein ID: 3019) showed the highest inhibitory effect on the tumor growth, compared with the comparative group. FIGS. 16e to 16g are the graphs showing the anti-cancer effect of each antibody by one person, when injected with PBMC derived from three different persons (3 persons) in the experiment. The group administered by humanized 8F5 antibody (protein ID: 3019; P E3) showed the highest anti-cancer effects were confirmed in three different PBMC-treated groups and similar results were confirmed in the other two experimental sets.

The invention claimed is:

1. An anti-CD66c (Cluster of Differentiation 66c) antibody or an antigen-binding fragment thereof, comprising the following complementarity determining regions (CDRs):
   CDR-H1 comprising an amino acid sequence of SEQ ID NO: 1 or 9,
   CDR-H2 comprising an amino acid sequence of SEQ ID NO: 2 or 10,
   CDR-H3 comprising an amino acid sequence of SEQ ID NO: 3,
   CDR-L1 comprising an amino acid sequence of SEQ ID NO: 4, 11 or 12,
   CDR-L2 comprising an amino acid sequence of SEQ ID NO: 5 and
   CDR-L3 comprising an amino acid sequence of SEQ ID NO: 6 or 13,
   on the proviso that the antibody comprising CDRs consisting of amino acid sequences of SEQ ID NOs: 1, 2, 3, 4, 5, and 6 is not included.

2. The anti-CD66c antibody or an antigen-binding fragment thereof according to claim 1, wherein the heavy chain variable region of the antibody comprises at least one selected from the group consisting of framework sequence (V-FR1) including the amino acid sequence of SEQ ID NO: 23, 24, 25, 26 or 27, framework sequence (V-FR2) including the amino acid sequence of SEQ ID NO: 33, 34, 35, 36 or 37, framework sequence (V-FR3) including the amino acid sequence of SEQ ID NO: 43, 44, 45, 46 or 47, and framework sequence (V-FR4) including the amino acid sequence of SEQ ID NO: 53, 54, 55, 56 or 57.

3. The anti-CD66c antibody or an antigen-binding fragment thereof according to claim 1, wherein the light chain variable region of the antibody comprises at least one selected from the group consisting of framework sequence (L-FR1) including the amino acid sequence of SEQ ID NO: 29, 30 or 31, framework sequence (L-FR2) including the amino acid sequence of SEQ ID NO: 39, 40 or 41, framework sequence (L-FR3) including the amino acid sequence of SEQ ID NO: 49, 50, or 51, and framework sequence (L-FR4) including the amino acid sequence of SEQ ID NO: 59, 60 or 61.

4. The anti-CD66c antibody or an antigen-binding fragment thereof according to claim 1, comprising a heavy chain variable region including the amino acid sequence of SEQ ID NO: 14, 15, 16, 17 or 18, and a light chain variable region including the amino acid sequence of SEQ ID NO: 19, 20, or 21.

5. The anti-CD66c antibody or an antigen-binding fragment thereof according to claim 1, wherein the fluorescence variability of the antibody against ANS reagent is less than 200% at 62° C.

6. The anti-CD66c antibody or an antigen-binding fragment thereof according to claim 1, wherein the antigen-binding fragment is scFv, (scFv)2, Fab, Fab' or F(ab')$_2$ of anti-CD66c antibody.

7. A method of treating a disease selected from cancer and cancer metastasis, comprising administering the anti-CD66c antibody or the antigen-binding fragment thereof according to claim 1 to a subject having cancer or cancer metastasis.

8. The method according to claim 7, wherein the cancer is CD66c-positive solid cancer.

9. The method according to claim 8, wherein the solid cancer is lung cancer, colon cancer, stomach cancer, liver cancer, breast cancer, or prostate cancer which are CD66c-positive.

10. The method according to claim 7, further comprising administering an inhibitor of PD-1 or PD-L1 binding to the subject having cancer or cancer metastasis.

11. A nucleic acid molecule encoding the amino acid sequence of the heavy chain variable region selected from SEQ ID NOs:14, 15, 16, 17, and 18; encoding the amino acid sequence of the light chain variable region selected from SEQ ID NOs:19, 20, and 21; or encoding one of said heavy chain variable regions and one of said light chain variable regions.

12. A recombinant vector comprising the nucleic acid molecule according to claim 11.

13. A recombinant cell comprising the recombinant vector according to claim 12.

* * * * *